US012694986B2

(12) United States Patent
Bhar et al.

(10) Patent No.: US 12,694,986 B2
(45) Date of Patent: Jul. 28, 2026

(54) METHOD AND SYSTEM FOR RISK ASSESSMENT OF POLYCYSTIC OVARIAN SYNDROME (PCOS)

(71) Applicant: Tata Consultancy Services Limited, Mumbai (IN)

(72) Inventors: Subhrajit Bhar, Pune (IN); Rashmi Singh, Pune (IN); Mohammed Monzoorul Haque, Pune (IN); Sharmila Shekhar Mande, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 13 days.

(21) Appl. No.: 18/601,951

(22) Filed: Mar. 11, 2024

(65) Prior Publication Data

US 2024/0371525 A1     Nov. 7, 2024

(30) Foreign Application Priority Data

Apr. 19, 2023     (IN) .............................. 202321028611

(51) Int. Cl.
    *G16H 50/30*        (2018.01)
    *G16H 10/40*        (2018.01)
(52) U.S. Cl.
    CPC ............. *G16H 50/30* (2018.01); *G16H 10/40* (2018.01)
(58) Field of Classification Search
    CPC ............................... G16H 50/30; G16H 10/40
    See application file for complete search history.

(56) References Cited

FOREIGN PATENT DOCUMENTS

CN        112229937 A        1/2021

OTHER PUBLICATIONS

Zhao, Xiaoxuan et al., "How to Screen and Prevent Metabolic Syndrome in Patients of PCOS Early: Implications from Metabolomics", Title of the item: Frontiers in Endocrinology, Date: Jun. 2021, vol. 12, Publisher: PubMed, Link: https://pubmed.ncbi.nlm.nih.gov/34149613/.
Belkova, Natalia et al., "Metagenome datasets from women with polycystic ovary syndrome from Irkutsk, Eastern Siberia, Russia", Title of the item: Data in Brief, Date: Oct. 2020, vol. 32, Publisher: Science Direct, Link: https://www.sciencedirect.com/science/article/pii/S2352340920310313?via%3Dihub.

*Primary Examiner* — Steven G. S. Sanghera
(74) *Attorney, Agent, or Firm* — Finnegan, Henderson, Farabow, Garrett & Dunner, LLP

(57)        ABSTRACT
This disclosure relates generally to and, more particularly, to assessment of PCOS. Polycystic ovarian syndrome (PCOS) is a hormonal disorder common among women of reproductive age that causes infertility and affects overall health of the woman. As PCOS is common and curable cause of infertility, an efficient early screening to assess a potential risk of PCOS can ensure early treatment. The current state-of-the-art techniques include diagnostic, screening solutions, imaging techniques which are invasive, complex, expensive. The disclosure is a supervised machine learning algorithm on the samples of individuals to arrive at a panel of biological features/indicators/markers/signatures that can accurately stratify/classify/group individuals into 'PCOS' and 'healthy' based upon the differences in the composition of the gut/oral microbial communities.

12 Claims, 8 Drawing Sheets

Specification includes a Sequence Listing.

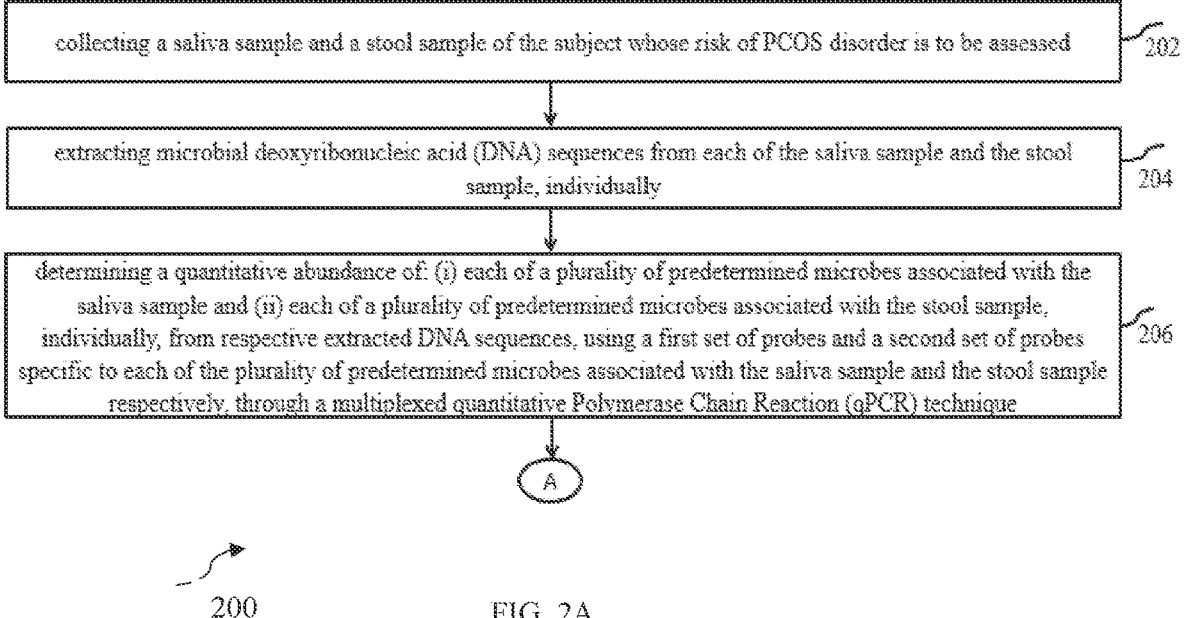

collecting a saliva sample and a stool sample of the subject whose risk of PCOS disorder is to be assessed ⌐202 extracting microbial deoxyribonucleic acid (DNA) sequences from each of the saliva sample and the stool sample, individually ⌐204 determining a quantitative abundance of: (i) each of a plurality of predetermined microbes associated with the saliva sample and (ii) each of a plurality of predetermined microbes associated with the stool sample, individually, from respective extracted DNA sequences, using a first set of probes and a second set of probes specific to each of the plurality of predetermined microbes associated with the saliva sample and the stool sample respectively, through a multiplexed quantitative Polymerase Chain Reaction (qPCR) technique ⌐206

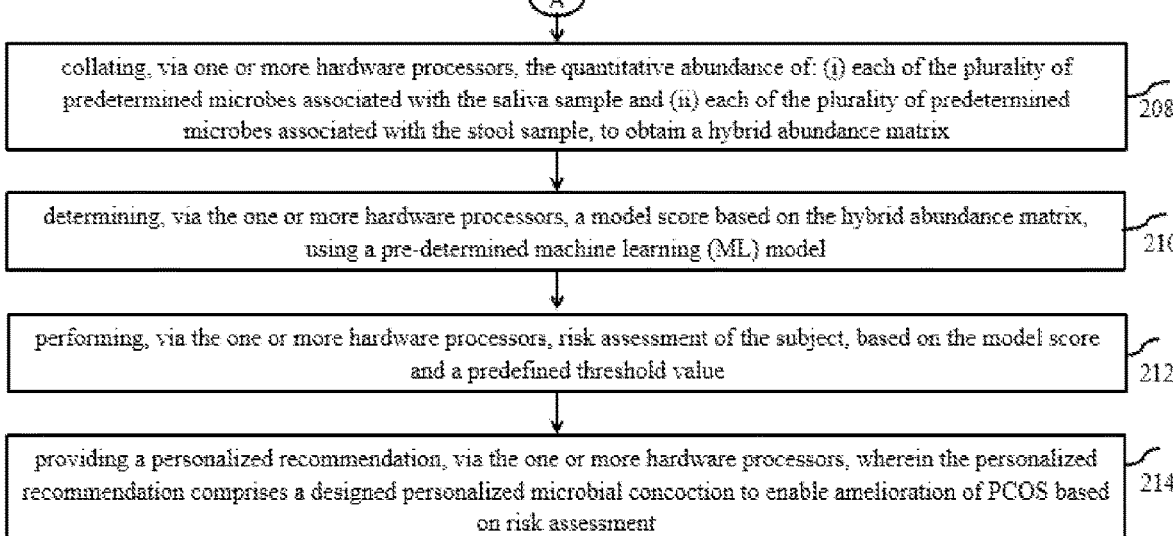

collating, via one or more hardware processors, the quantitative abundance of: (i) each of the plurality of predetermined microbes associated with the saliva sample and (ii) each of the plurality of predetermined microbes associated with the stool sample, to obtain a hybrid abundance matrix ⟶ 208 determining, via the one or more hardware processors, a model score based on the hybrid abundance matrix, using a pre-determined machine learning (ML) model ⟶ 210 performing, via the one or more hardware processors, risk assessment of the subject, based on the model score and a predefined threshold value ⟶ 212 providing a personalized recommendation, via the one or more hardware processors, wherein the personalized recommendation comprises a designed personalized microbial concoction to enable amelioration of PCOS based on risk assessment ⟶ 214

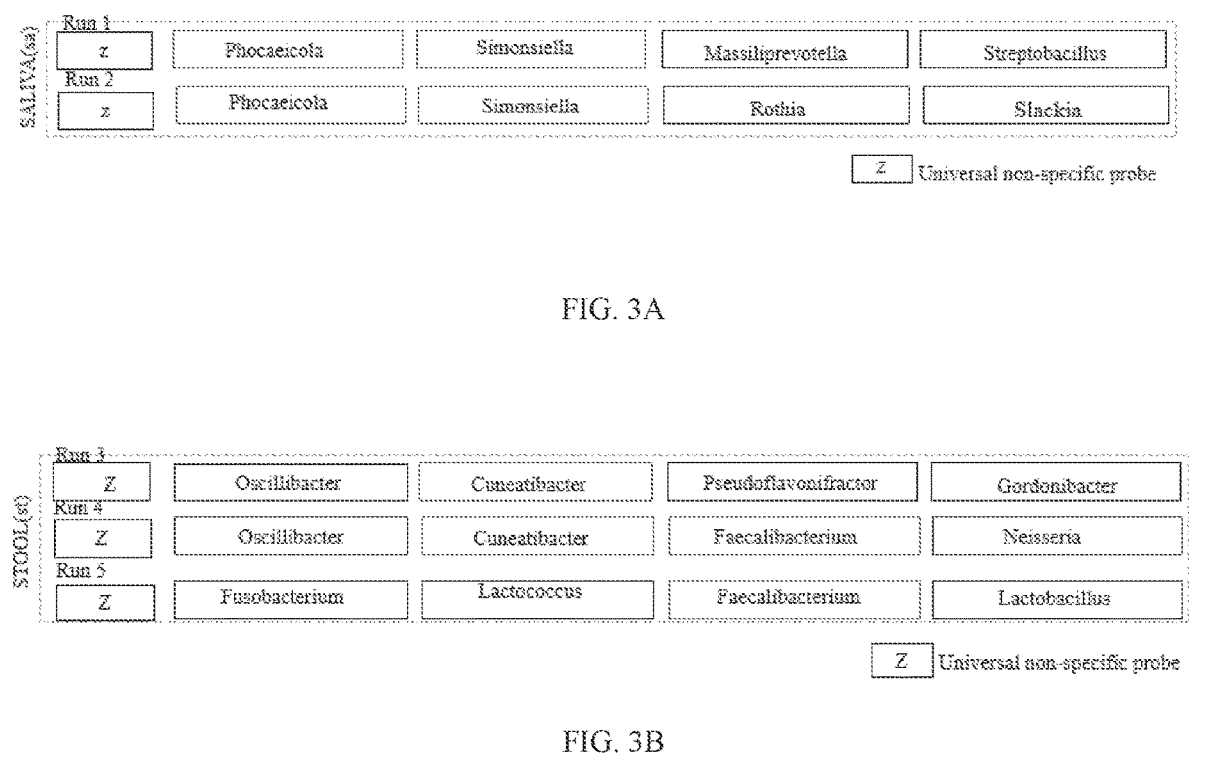

| SALIVA(sa) | Run 1 | | | | |
|---|---|---|---|---|---|
| | z | Phocaeicola | Simonsiella | Massiliprevotella | Streptobacillus |
| | Run 2 | | | | |
| | z | Phocaeicola | Simonsiella | Rothia | Slackia |

| z | Universal non-specific probe |
|---|---|

FIG. 3A

| STOOL(st) | Run 3 | | | | |
|---|---|---|---|---|---|
| | Z | Oscillibacter | Cuneatibacter | Pseudoflavonifractor | Gordonibacter |
| | Run 4 | | | | |
| | Z | Oscillibacter | Cuneatibacter | Faecalibacterium | Neisseria |
| | Run 5 | | | | |
| | Z | Fusobacterium | Lactococcus | Faecalibacterium | Lactobacillus |

| Z | Universal non-specific probe |
|---|---|

FIG. 3B

Assign one of a healthy class tag or an unhealthy class tag to each of the samples in the collected plurality of training biological samples 402

Generate training data comprising of a plurality of microbial abundance profiles corresponding to each of the plurality of training biological samples, wherein each microbial abundance profile corresponding to a training biological sample comprises of one or a plurality of features and respective abundance values of the features, and wherein each feature in the microbial abundance profile corresponds to one of a plurality of microbial taxonomic groups present in the training biological sample 404

Partition the training data into an internal training set and an internal test set 406

Randomly select a predefined number of subsets out of the internal training set, wherein each subset comprises of a randomly selected plurality of microbial abundance profiles corresponding to the training biological samples in the randomly selected subset, and wherein each subset comprises a proportionate part of samples belonging to the healthy class and the remaining samples belonging to the unhealthy class 408

Note for each selected subset, a distribution of the abundance values of each of the features across the plurality of training biological samples in the selected subset, and the distribution of the abundance values of each of the features across the training biological samples belonging to the healthy class in the selected subset and the training biological samples belonging to the unhealthy class in the selected subset 410

Calculate from the noted distributions of each selected subset, a first quartile value (Q1) and a third quartile value (Q3) of the distribution of each of the features across each of the plurality of training biological samples in the selected subset 412

B

Calculate for each selected subset, a second quartile value of the distribution of each of the features across the training biological samples belonging to the healthy class (Q2_A) ) in the selected subset and the training biological samples belonging to the unhealthy class (Q2_B) in the selected subset 414

Calculate Q1, Q3 Q2_A Q2_B for each of a predefined number of subsets (M) 416

Calculate median value for all calculated Q1, median value for all calculated Q3, median value for all calculated Q2_A and median value for all calculated Q2_B 418

Perform a Mann-Whitney test to test if a value of the feature is significantly different between the samples belonging to the healthy class and the samples belonging to the unhealthy class 420

Shortlist the features based on a first predefined criteria utilizing calculated median values and the Mann-Whitney test 422

Generate a set of features using the shortlisted features using a second predefined criteria, wherein the set of features are less than or equal to 15 424

Create a plurality of combinations of the features present in the set of features to generate corresponding plurality of candidate feature sets, wherein the plurality of combinations of features comprises a minimum of two and a maximum of 15 features 426

FIG. 4B

400

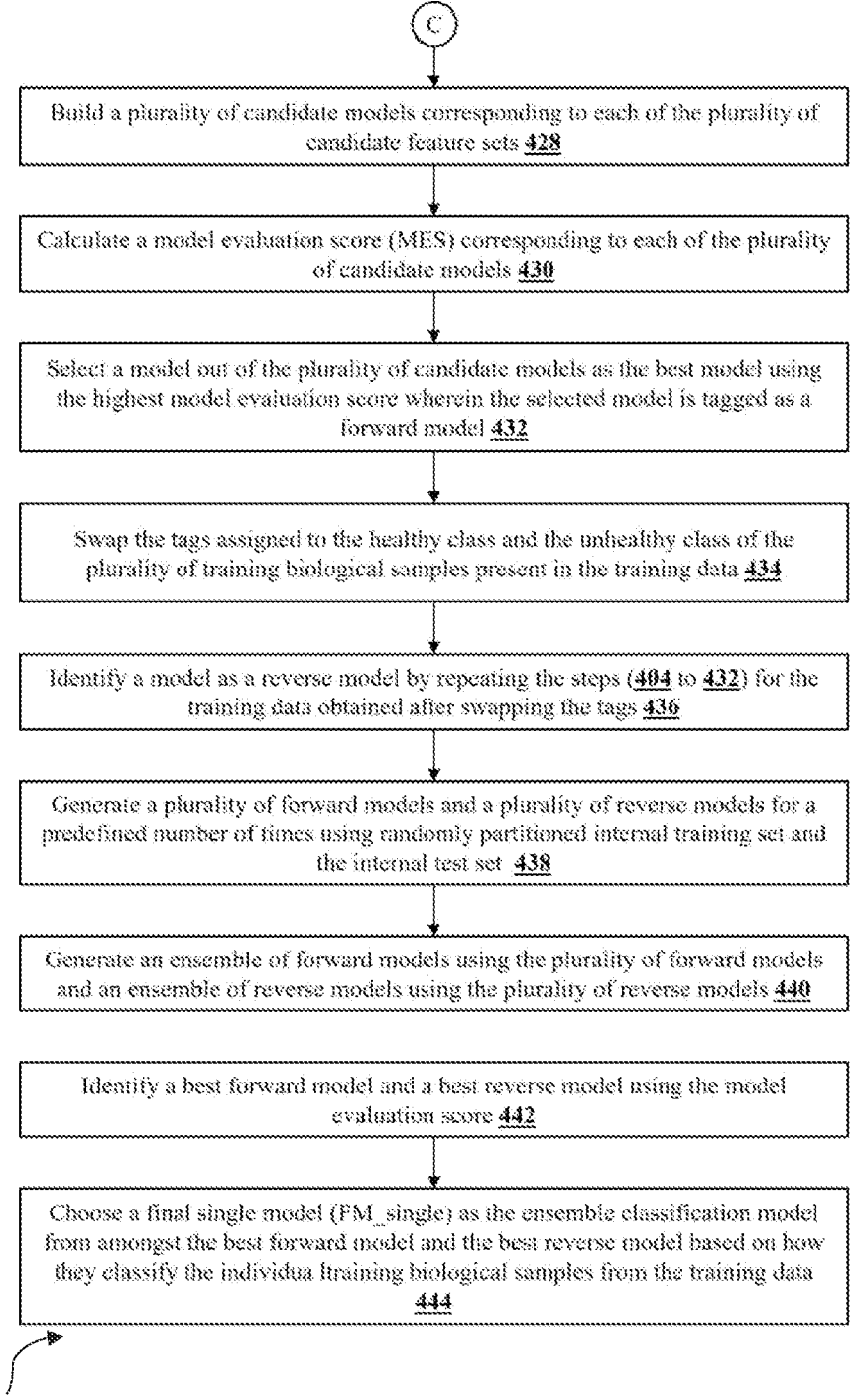

C

Build a plurality of candidate models corresponding to each of the plurality of candidate feature sets 428

Calculate a model evaluation score (MES) corresponding to each of the plurality of candidate models 430

Select a model out of the plurality of candidate models as the best model using the highest model evaluation score wherein the selected model is tagged as a forward model 432

Swap the tags assigned to the healthy class and the unhealthy class of the plurality of training biological samples present in the training data 434

Identify a model as a reverse model by repeating the steps (404 to 432) for the training data obtained after swapping the tags 436

Generate a plurality of forward models and a plurality of reverse models for a predefined number of times using randomly partitioned internal training set and the internal test set 438

Generate an ensemble of forward models using the plurality of forward models and an ensemble of reverse models using the plurality of reverse models 440

Identify a best forward model and a best reverse model using the model evaluation score 442

Choose a final single model (FM_single) as the ensemble classification model from amongst the best forward model and the best reverse model based on how they classify the individual training biological samples from the training data 444

METHOD AND SYSTEM FOR RISK ASSESSMENT OF POLYCYSTIC OVARIAN SYNDROME (PCOS)

PRIORITY CLAIM

This U.S. patent application claims priority under 35 U.S.C. § 119 to: Indian Patent Application No. 202321028611, filed on Apr. 19, 2023. The entire contents of the aforementioned application are incorporated herein by reference.

REFERENCE TO SEQUENCE LISTING SUBMITTED ELECTRONICALLY

An official copy of the sequence listing is submitted electronically via EFS-WEB as an ST.26 XML formatted sequence listing with a file named PCOS RISK ASSESS-MENT.xml, created on May 25, 2026, having a size of 36804 bytes. The sequence listing contained in this ST.26 XML formatted document is part of the specification and is herein incorporated by reference in its entirety.

TECHNICAL FIELD

The disclosure herein generally relates to risk assessment of diseases and, more particularly, to risk assessment for Polycystic Ovarian Syndrome (PCOS).

SEQUENCE LISTING

This application contains a Sequence Listing which has been submitted in ST. 26 format via EFS-Web and is hereby incorporated by reference in its entirety. The ST. 26 copy, created on Jan. 12, 2024, is named Sequence_listing(Method and system for risk assessment for poly-cystic ovarian syndrome (PCOS))_US.txt and is 36,883 bytes in size.

BACKGROUND

Polycystic Ovarian Syndrome (PCOS) is a hormonal disorder common among women of reproductive age, wherein the ovaries may develop numerous small collections of fluid (follicles) and fail to regularly release eggs thus causing infrequent or prolonged menstrual periods or excess excretion of male hormone (androgen) levels in affected females. PCOS causes infertility and affects overall health of the woman. However, PCOS is a common and curable cause of infertility. Hence an efficient early screening technique to assess a potential (presence) risk of PCOS or predisposition to the same, can ensure early management/treatment and help in reducing/obviating/ameliorating PCOS and PCOS associated symptoms thereby addressing the related health implications. The phrase 'risk assessment of PCOS' also referred to as 'risk of PCOS' means/indicates/includes the methods for screening/diagnosis/detection/assessment of PCOS and PCOS related symptoms in a subject or methods for screening the subject for predisposition to PCOS.

The current state-of-the-art for PCOS screening/diagnosis/detection/assessment techniques include Rotterdam criterion, Hormone tests, Blood tests and Ultrasound tests. The current state-of-the-art for PCOS criteria/tests lack precision and pose challenges/limitations in a clinical context due to dependency on clinical symptoms that either may be absent or are minimally expressed or are not fully expressed such as to escape diagnosis in the affected individual or these symptoms may be common to other diseases. Successful diagnosis of PCOS requires several differential diagnostic techniques that is expensive for the patient. Although existing (advanced) imaging techniques including transvaginal ultrasonography reduce the chance of false negatives for diagnosis of PCOS, the technique is an expensive and invasive procedure and also requires (or necessitates) technical expertise for handling requisite medical equipment. Further some existing PCOS detection/screening techniques use protein biomarkers and follicular fluid biomarkers for differentiating between healthy and PCOS affected individuals, however, these techniques are not commercially available due to uncertainty of accuracy of assessment for most of these methods as they are based on changes in level of expression of certain serum proteins or specific proteins in follicular fluid respectively. Hence there is a requirement for a non-invasive, simple, less expensive technique for risk assessment of poly-cystic ovarian syndrome (PCOS).

SUMMARY

Embodiments of the present disclosure present technological improvements as solutions to one or more of the above-mentioned technical problems recognized by the inventors in conventional systems. For example, in one embodiment, a method and a system for risk assessment of PCOS is provided. The risk assessment for PCOS includes one of screening/diagnosis/detection/assessment of PCOS in an individual or a subject.

In another aspect, a method for risk assessment of PCOS is provided. The method includes collecting a saliva sample and a stool sample of a subject whose risk of PCOS disorder is to be assessed; extracting microbial deoxyribonucleic acid (DNA) sequences from each of the saliva sample and the stool sample, individually; determining a quantitative abundance of: (i) each of a plurality of predetermined microbes associated with the saliva sample and (ii) each of a plurality of predetermined microbes associated with the stool sample, individually, from respective extracted DNA sequences, using a first set of probes and a second set of probes specific to each of the plurality of predetermined microbes associated with the saliva sample and the stool sample respectively, through a multiplex quantitative Polymerase Chain Reaction (qPCR) technique; collating, via one or more hardware processors, the quantitative abundance of: (i) each of the plurality of predetermined microbes associated with the saliva sample and (ii) each of the plurality of predetermined microbes associated with the stool sample, to obtain a hybrid abundance matrix; determining, via the one or more hardware processors, a model score based on the hybrid abundance matrix, using a pre-determined machine learning (ML) model; and performing, via the one or more hardware processors, PCOS risk assessment of the subject, based on the model score and a predefined threshold value. The risk assessment for PCOS includes one of screening/diagnosis/detection/assessment of PCOS in an individual or a subject.

In yet another aspect, a kit for risk assessment of PCOS in a subject is provided. The kit comprising: an input module for receiving a saliva sample and a stool sample of the subject whose risk of PCOS is to be assessed; one or more hardware processors configured to analyze the saliva sample and the stool sample; and an output module for displaying the risk assessment of PCOS of the subject, based on the analysis by the one or more hardware processors.

In an embodiment, the plurality of predetermined microbes associated with the saliva sample are: *Phocaeicola, Simonsiella, Massiliprevotella, Streptobacillus, Rothia,* and *Slackia*; and the plurality of predetermined microbes associated with the stool sample are: *Oscillibacter, Cuneatibacter, Faecalibacterium, Pseudoflavonifractor, Gordonibacter, Neisseria, Fusobacterium, Lactococcus,* and *Lactobacillus.*

In an embodiment, the first set of probes specific to each of the plurality of predetermined microbes associated with the saliva sample are utilized in a first multiplex qPCR run, and a second multiplex qPCR run, to determine the quantitative abundance of each of the plurality of predetermined microbes associated with the saliva sample, and wherein:

(i) the plurality of predetermined microbes, the quantitative abundance of which are being determined through the first multiplex qPCR run are: *Phocaeicola, Simonsiella, Massiliprevotella* and *Streptobacillus*; and (ii) the plurality of predetermined microbes, the quantitative abundance of which are being determined through the second multiplex qPCR run are: *Phocaeicola, Simonsiella, Rothia,* and *Slackia.*

In an embodiment, the second set of probes specific to each of the plurality of predetermined microbes associated with the stool sample are utilized in a third multiplex qPCR run, fourth multiplex qPCR run, and a fifth multiplex qPCR run, to determine the quantitative abundance of each of the plurality of predetermined microbes associated with the stool sample, and wherein:

(i) the plurality of predetermined microbes, the quantitative abundance of which are being determined through the third multiplex qPCR run are: *Oscillibacter, Cuneatibacter, Pseudoflavonifractor,* and *Gordonibacter,* and (ii) the plurality of predetermined microbes, the quantitative abundance of which are being determined through the fourth multiplex qPCR run are: *Oscillibacter, Cuneatibacter, Faecalibacterium* and *Neisseria*; and (iii) the plurality of predetermined microbes, the quantitative abundance of which are being determined through the fifth multiplex qPCR run are: *Fusobacterium, Lactococcus, Faecalibacterium,* and *Lactobacilus.*

In an embodiment, the pre-determined machine learning (ML) model is an ensemble ML model that is built using a microbial abundance data corresponding to a plurality of training saliva samples and a plurality of training stool samples.

In an embodiment, the plurality of predetermined microbes associated with the saliva sample and the plurality of predetermined microbes associated with the stool sample are features of the pre-determined machine learning (ML) model.

In an embodiment, the one or more predetermined microbes out of the plurality of predetermined microbes associated with the saliva sample that are common to the plurality of predetermined microbes, the quantitative abundance of which are being determined through the first multiplex qPCR run, wherein the plurality of predetermined microbes determined through the first multiplex qPCR run include *Phocaeicola, Simonsiella, Massiliprevotella* and *Streptobacillus* and the plurality of predetermined microbes, the quantitative abundance of which are being determined through the second multiplex qPCR run, wherein the plurality of predetermined microbes determined through the second multiplex qPCR run include *Phocaeicola, Simonsiella, Rothia,* and *Slackia* which are determined based on (i) a median abundance of each of the plurality of predetermined microbes obtained from the plurality of training saliva samples, (ii) a frequency of occurrence of each of the plurality of predetermined microbes constituting the ensemble ML model.

In an embodiment, the one or more predetermined microbes out of the plurality of predetermined microbes associated with the stool sample that are common to the plurality of predetermined microbes, the quantitative abundance of which are being determined through the third multiplex qPCR run, wherein the plurality of predetermined microbes determined through the third multiplex qPCR run include *Oscillibacter, Cuneatibacter, Pseudoflavonifractor,* and *Gordonibacter*) and the plurality of predetermined microbes, the quantitative abundance of which are being determined through the fourth multiplex qPCR run, wherein the plurality of predetermined microbes determined through the fourth multiplex qPCR run include *Oscillibacter, Cuneatibacter, Faecalibacterium* and *Neisseria*) and the plurality of predetermined microbes, the quantitative abundance of which are being determined through the fifth multiplex qPCR run, wherein the plurality of predetermined microbes determined through the fifth multiplex qPCR run include *Fusobacterium, Lactococcus, Faecalibacterium,* and *Lactobacilus* which are determined based on (i) a median abundance of each of the plurality of predetermined microbes obtained from the plurality of training stool samples, (ii) a frequency of occurrence of each of the plurality of predetermined microbes constituting the ensemble ML model.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 2A and FIG. 2B is a flow diagram illustrating a method (200) for risk assessment of PCOS in accordance with some embodiments of the present disclosure.

FIG. 3A is an exemplary probe and multiplexed qPCR based design for detecting and determining the quantitative abundance of each of a plurality of predetermined microbes for a saliva sample and FIG. 3B is an exemplary probe and multiplexed qPCR based design for detecting and determining the quantitative abundance of each of a plurality of predetermined microbes for a stool sample for risk assessment of PCOS in accordance with some embodiments of the present disclosure.

FIGS. 4A, 4B and 4C are flowcharts illustrating steps involved in building a pre-determined machine learning model according to some embodiments of the present disclosure.

DETAILED DESCRIPTION

Figure 1:
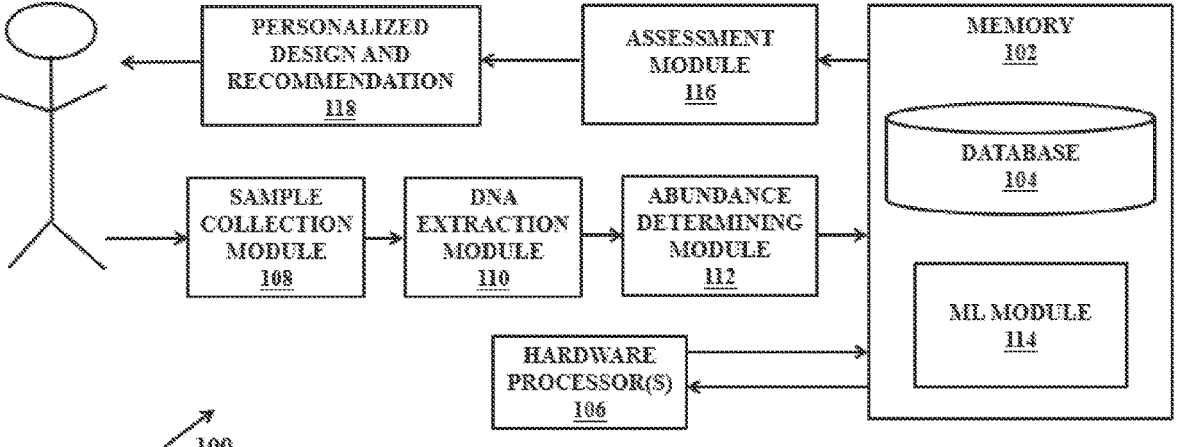
FIG. 1 illustrates a functional block diagram for risk assessment of PCOS according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

DEFINITION OF KEY TERMS

Microbiota: The collection of microorganisms, such as bacteria, archaea, protists, fungi, and viruses, that inhabit a particular ecological niche or geographical site.

Microbiome: The collection of genetic material of microorganisms that reside in a particular geographical niche.

Probiotics: A micro-organism or a collection of microorganisms introduced into the body for its beneficial qualities.

Prebiotics: A non-digestible food or food component that promotes the growth of beneficial micro-organisms in the gut.

Synbiotics: Synbiotics refer to foods or food components/ ingredients/supplements that combine probiotics and prebiotics so that the beneficial effect of both is exerted in a form of synergism, hence synbiotics.

Metabiotics: Metabiotics are the structural components of probiotic microorganisms alone or in combination with their metabolites/signaling molecules that are capable of exerting beneficial effects on host.

Biotherapeutics: Biotherapeutics are products used as drugs/personalized recommendation to candidates with active component extracted or produced by biological source.

Nutraceuticals: Nutraceuticals are food components that have a potentially positive effect on health beyond basic nutrition by promoting optimal health and by reducing the risk of disease.

'PCOS': The term "PCOS" refers to an individual/patient/ subject who has poly-cystic ovarian syndrome 'healthy': The term 'healthy' refers to an individual/ subject who does not have PCOS Polycystic ovarian syndrome (PCOS) is a hormonal disorder common among women of reproductive age. The ovaries may develop numerous small collections of fluid (follicles) and fail to regularly release eggs thus causing infrequent or prolonged menstrual periods or excess male hormone (androgen) levels in affected females. One of the existing state-of-art assessment of PCOS is based on the "Rotterdam criterion" wherein, the Rotterdam criterion includes (a) Oligo-ovulation and/or anovulation, (b) Hyper androgen activity and (c) Poly-cystic ovaries (by gynecologic ultrasound) and PCOS to be present if any 2 out of 3 criteria are met. However, the "Rotterdam criterion" symptoms may as well be absent/late in PCOS individuals thus falling short to satisfy the requirements of the Rotterdam criterion which limits its assessment accuracy in screening of PCOS.

Further many diseases such as Cushing's syndrome, Congenital Adrenal Hyperplasia, Hyperprolactinemia, Hyperthyroidism or ovarian or an adrenal tumor etc., mimic closely the PCOS related clinical symptoms and hence PCOS diagnosis requires differential diagnostics to rule out any other similar medical condition. The differential diagnostics increase the overall diagnostic costs but still suffer from lack of specificity.

Further techniques such as Ultra-sound imaging of ovarian cysts also suffer from erroneous risk assessment and lack of screening efficacy since most medical practitioners consider occurrence of polycystic ovaries as the final confirmation for PCOS, however, around 12-25 undeveloped follicles are present in the ovary (in all women irrespective of presence/absence of PCOS) during the follicular phase of the menstrual cycle that lasts for 14 days. Hence if the ovulation fails to occur due to any other factor, the follicles remain undeveloped even in the luteal phase, but if tested again after a few months, the follicles will not be present in the luteal phase and the ovaries will appear normal in ultrasound even if the woman has PCOS. The above challenges are met through an additional set of criteria for more accurate diagnosis [Jonard, Sophie, et al. 2003, Ultrasound examination of polycystic ovaries: is it worth counting the follicles?] i.e., presence of $\geq 12$ follicles measuring 2-9 mm in diameter and increased ovarian area (>5.5 cm2) or volume (>11 mL). This, however, requires a transvaginal ultrasonography for assessment, which is an invasive procedure.

To overcome the above challenges present in the existing state of art, the disclosure proposes a supervised machine learning algorithm on the biological samples of individuals to arrive at a panel of biological features/indicators/markers/ signatures that can accurately predict/stratify/classify/group individuals into 'PCOS' and 'healthy' based upon the differences in the composition of the gut and/or oral microbial communities.

The disclosure can reliably predict the health status of an individual as PCOS or healthy by examining the composition and/or function of the microbes present in a stool and/or saliva sample obtained from an individual, thus making the disclosed method and system for risk assessment of PCOS relatively simple, non-invasive, cost-efficient, geography agnostic and independent of any post experimental follow up studies. Further, the disclosure also describes a method for design of personalized recommendable compositions for applications towards amelioration of PCOS in individuals assessed to be having PCOS or assessed to be at risk of getting affected by PCOS.

Referring now to the drawings, and more particularly to FIG. 1 through FIG. 5, where similar reference characters denote corresponding features consistently throughout the figures, there are shown preferred embodiments and these embodiments are described in the context of the following exemplary system and/or method.

FIG. 1 is an exemplary block diagram of a system 100 for risk assessment of PCOS in accordance with some embodiments of the present disclosure.

In an embodiment, the system 100 includes a memory 102, a database 104, a one or more hardware processors 106, a sample collection module 108, a DNA extraction module 110, an abundance determining module 112, a ML module 114 stored in the memory 106, an assessment module 116, and a personalized design and recommendation module 118.

In an embodiment, the system 100 includes a hardware processor(s) 106, one or more data storage devices or a memory 102 operatively coupled to the hardware processor(s) 106. The system 100 with one or more hardware processors is configured to execute functions of one or more functional blocks of the system 100.

Referring to the components of the system 100, in an embodiment, the processor(s) 106, can be one or more hardware processors 106. In an embodiment, the one or more hardware processors 106 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 106 is configured to fetch and execute computer-readable instructions stored in the memory 102. In an embodiment, the system 100 can be implemented in a variety of computing systems including laptop computers, notebooks, hand-held devices such as mobile phones, workstations, mainframe computers, servers, a network cloud and the like.

The memory 102 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes.

Further, the memory 102 may include a database 104 configured to include information regarding risk assessment for PCOS. The memory 102 may comprise information pertaining to input(s)/output(s) of each step performed by the processor(s) 106 of the system 100 and methods of the present disclosure. In an embodiment, the database 104 may be external (not shown) to the system 100 and coupled to the system via the I/O interface 106.

The Sample collection module 108 configured to collect a saliva sample and a stool sample of the subject whose risk of PCOS disorder is to be assessed.

The system 100 further comprises the DNA extraction module configured to extract microbial deoxyribonucleic acid (DNA) sequences from each of the saliva sample and the stool sample, individually.

The system 100 further comprises the abundance determining module 112 configured to determine a quantitative abundance of:

(i) each of a plurality of predetermined microbes associated with the saliva sample and (ii) each of a plurality of predetermined microbes associated with the stool sample, individually, from respective extracted DNA sequences, The abundance determining module 112 is configured to determine a quantitative abundance using a first set of probes and a second set of probes specific to each of the plurality of predetermined microbes associated with the saliva sample and the stool sample respectively, through a multiplex quantitative Polymerase Chain Reaction (qPCR) technique. The abundance determining module 112 is also configured to collate, the quantitative abundance of:

(i) each of the plurality of predetermined microbes associated with the saliva sample and (ii) each of the plurality of predetermined microbes associated with the stool sample, to obtain a hybrid abundance matrix;

The system 100 further comprises the ML Module 114 configured to determine a model score based on the hybrid abundance matrix, using a pre-determined machine learning (ML) model. The system 100 further comprises the assessment module 116 configured to perform, risk assessment of the subject, based on the model score and a predefined threshold value.

The memory 102 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. Functions of the components of system 100 are explained in conjunction with flow diagrams depicted in FIGS. 2A and 2B for risk assessment for PCOS.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

In an embodiment, the memory 102 comprises one or more data storage devices operatively coupled to the processor(s) 106 and is configured to store instructions for execution of steps of the method depicted in FIGS. 2A and 2B by the processors 106 The steps of the method of the present disclosure will now be explained with reference to the components or blocks of the system 100 as depicted in FIG. 1 and the steps of flow diagrams as depicted in FIGS. 2A-2B and FIG. 3A-3B. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

At step 202 of the method 200, a saliva sample and a stool sample of the subject is collected at the sample collection module 108. The subject is a woman (a female viviparous mammal) whose risk of PCOS disorder is to be assessed.

In an embodiment, the sample collection module 108 can be modified to collect the microbiome sample from a body site/location other than the gut/oral e.g., vaginal/cervical sample etc. Microbiome samples from healthy or diseased subjects, belonging to any ecological niche or geographical location or from any other female mammalian organism are covered in the scope of this invention. In another embodiment, any other disease that targets/modifies the gut/oral microbiome or vice-versa is under the scope of the invention.

In an example scenario, both the saliva sample and the stool sample are oral microbial and gut microbial site-specific samples and are non-invasive. In an embodiment, the saliva sample may refer to extracted salivary swabs or naturally out-flown saliva or voluntarily spitted saliva which is obtained in a non-stimulatory environment (where stimulations refer to behavioral or digestive triggers). In general, the saliva sample is extracted from the mouth site of the subject. The stool samples refer to the stool obtained from the subject.

At step 204 of the method 200, microbial deoxyribonucleic acid (DNA) sequences are extracted from each of the saliva sample and the stool sample, individually at the DNA extraction module 110.

In an embodiment, the extraction of microbial DNA sequences from the collected gut/oral (represented by fecal/saliva samples, respectively) biological sample is performed using standard protocols and kits known in the art, and thereafter 16S rRNA marker genes (either full-length or specific variable regions of the gene) are amplified using PCR (polymerase chain reaction) and the amplified DNA fragments are sequenced using a next-generation sequencing (NGS) platform. In another embodiment, the NGS technology can include any one of whole genome sequencing, CPN60 gene-based amplicon sequencing, other phylogenetically conserved genetic region-based amplicon sequencing, sequencing using approaches which involve either a fragment library or a mate-pair library or a paired-end library or a combination of the same. Further, in another embodiment, the DNA extraction module 110 includes taxonomic classification of the sequenced reads at genus level using RDP, and latest version of any other taxonomic classification database such as Greengenes or Silva databases, or algorithms such as dada2 are covered in the scope of this invention In an example scenario for the above stated embodiment (in previous paragraph), the extraction of microbial DNA from the collected gut/oral is performed using standard protocols and kits for DNA extraction and the sequencing is performed following the 16S amplicon sequencing and read classification carried out using RDP classifier.

At step 206 of the method 200, a quantitative abundance is determined at the abundance determining module 112. The quantitative abundance of:

(i) each of a plurality of predetermined microbes associated with the saliva sample and (ii) each of a plurality of predetermined microbes associated with the stool sample, The quantitative abundance is determined individually, from respective extracted DNA sequences, using a first set of probes and a second set of probes specific to each of the plurality of predetermined microbes associated with the saliva sample and the stool sample respectively, through a multiplex quantitative Polymerase Chain Reaction (qPCR) technique.

In an embodiment, abundance determination involves creating abundance/feature table and generation of the raw abundance/feature table or percent normalized abundance/feature table having percent normalized abundance values of taxa or microbial taxa (i.e., features) in each sample. In another embodiment, Multicolour Combinatorial Probe Coding (MCPC) qPCR/real-time PCR based measurement of abundance of the microbial taxonomic groups can also be considered for quantification of the abundance of a predefined set of taxa. Alternatively, any other pre-processing methods or data normalization techniques known in the state of art can be used for normalization and feature selection from the main feature table.

In an embodiment, as illustrated in FIG. 3A, the plurality of predetermined microbes associated with the saliva sample are: *Phocaeicola, Simonsiella, Massiliprevotella, Streptobacillus, Rothia*, and *Slackia*.

In an embodiment, as illustrated in FIG. 3B, the plurality of predetermined microbes associated with the stool sample are: *Oscillibacter, Cuneatibacter, Faecalibacterium, Pseudoflavonifractor, Gordonibacter, Neisseria, Fusobacterium, Lactococcus*, and *Lactobacillus*.

In an embodiment, one or more predetermined microbes out of the plurality of predetermined microbes associated with the saliva sample, is/are common to the first multiplex qPCR run and the second multiplex qPCR run for determining the quantitative abundance, and wherein the one or more predetermined microbes that are common to the first multiplex qPCR run and the second multiplex qPCR run are determined based on (i) a median abundance of each of the plurality of predetermined microbes obtained from the plurality of training saliva samples, (ii) a frequency of occurrence of each of the plurality of predetermined microbes constituting the ensemble ML model. The one or more predetermined microbes (from amongst the set of predetermined microbes) that has/have the highest (or relatively higher) median abundance or frequency of occurrence (as compared to the median abundance(s) or the frequency of occurrence of each microbe in the remaining set of predetermined microbes) across the plurality of training saliva samples is/are common to the first multiplex qPCR run and the second multiplex qPCR run.

In an embodiment, one or more predetermined microbes out of the plurality of predetermined microbes associated with the stool sample are common to the third multiplex qPCR run and the fourth multiplex qPCR run for determining the quantitative abundance, and wherein the one or more predetermined microbes that are common to the third multiplex qPCR run and the fourth multiplex qPCR run are determined based on (i) a median abundance of each of the plurality of predetermined microbes obtained from the plurality of training stool samples, (ii) a frequency of occurrence of each of the plurality of predetermined microbes constituting the ensemble ML model. The one or more predetermined microbes (from amongst the set of predetermined microbes) that has/have the highest (or relatively higher) median abundance or frequency of occurrence (as compared to the median abundance(s) or the frequency of occurrence of each microbe in the remaining set of predetermined microbes) across the plurality of training stool samples is/are common to the third multiplex qPCR run and the fourth multiplex qPCR run.

In an embodiment, one or more predetermined microbes out of the plurality of predetermined microbes associated with the stool sample are common to the fourth multiplex qPCR run and the fifth multiplex qPCR run for determining the quantitative abundance, and wherein the one or more predetermined microbes that are common to the fourth multiplex qPCR run and the fifth multiplex qPCR run are determined based on (i) a median abundance of each of the plurality of predetermined microbes obtained from the plurality of training stool samples, (ii) a frequency of occurrence of each of the plurality of predetermined microbes constituting the ensemble ML model. In an embodiment, the one or more predetermined microbes (from amongst the set of predetermined microbes) that has/have the highest (or relatively higher) median abundance or frequency of occurrence (as compared to the median abundance(s) or the frequency of occurrence of each microbe in the remaining set of predetermined microbes) across the plurality of training stool samples is/are common to the fourth multiplex qPCR run and the fifth multiplex qPCR run.

Also, the taxonomic nomenclature or names of one or more of the microbes (comprising the list of predetermined microbes) mentioned above may change, because of reasons like change in the version of the classification database, change in name of the microbe and any alternate names of the same set of microbes. The microbes affected by this change in nomenclature are well within the scope of the invention. Further the described methodology can be adopted for other datasets to arrive at additional region/age or other metadata specific models and recommendations.

Sharing below the representative sequences corresponding to the list of predetermined microbes. In case of change in the taxonomic nomenclature corresponding to the set of predetermined microbes, these sequences can be used as representative sequences for identifying the set of predetermined microbes and use them for designing appropriate probes for performing the multiplex qPCR runs. Although a representative sequence corresponds to a strain belonging to a genus from the set of predetermined microbes, analogous sequences corresponding to all other strains belonging to the same genus are also under the scope of this disclosure and can be used as representative sequences for the said genus.

The representative sequences corresponding to the list of predetermined microbes associated with the saliva samples are shared below:

Representative strain and its 16S ribosomal RNA sequence for the predetermined microbe *Phocaeicola* (other strains/species belonging to the same genus are also considered within scope of this disclosure)

>NR_175548.1 *Phocaeicola faecicola*
strain AGMB03916 16S ribosomal RNA,
complete sequence
ACAATGAAGAGTTTGATCCTGGCTCAGGATGAACGCTAGCTACAGGCTTA

ACACATGCAAGTCGAGGGGCAGCGGGATTGAAGCTTGCTTCAATTGCCGG

CGACCGGCGCACGGGTGAGTAACACGTATCCAACCTTCCGTTTACTCGGG

GATAGCCTTTCGAAAGAAAGATTAATACCCGATAGTATGGTGAGATTGCA

TGATAGCACCATTAAAGATTCATCGGTAAACGATGGGGATGCGTTCCATT

AGGTAGTAGGCGGGGTAACGGCCCACCTAGCCTGCGATGGATAGGGGTTC

TGAGAGGAAGGTCCCCCACATTGGAACTGAGACACGGTCCAAACTCCTAC

GGGAGGCAGCAGTGAGGAATATTGGTCAATGGGCGAGAGCCTGAACCAGC

CAAGTAGCGTGAAGGATGAAGGTCCTACGGATTGTAAACTTCTTTTATAA

GGGAATAAAACGCTCCACGTGTGGAGCCTTGTATGTACCTTATGAATAAG

CATCGGCTAACTCCGTGCCAGCAGCCGCGGTAATACGGAGGATGCGAGCG

TTATCCGGATTTATTGGGTTTAAAGGGAGCGCAGACGGGATGTTAAGTCA

GCTGTGAAAGTTTGCGGCTCAACCGTAAAATTGCAGTTGATACTGGCGTT

CTTGAGTGCAGTTGAGGTGTGCGGAATTCGTGGTGTAGCGGTGAAATGCT

TAGATATCACGAAGAACTCCGATTGCGAAGGCAGCTCACTAAACTGTAAC

TGACGTTCATGCTCGAAAGTGTGGGTATCAAACAGGATTAGATACCCTGG

TAGTCCACACGGTAAACGATGGATACTCGCTGTTGGCGATATACGGTCAG

CGGCCAAGCGAAAGCGTTAAGTATCCCACCTGGGGAGTACGCCGGCAACG

GTGAAACTCAAAGGAATTGACGGGGGCCCGCACAAGCGGAGGAACATGTG

GTTTAATTCGATGATACGCGAGGAACCTTACCCGGGCTTAAATTGCAGAG

GAATGATCTGGAAACAGGTCAGTCTTCGGACTTCTGTGAAGGTGCTGCAT

GGTTGTCGTCAGCTCGTGCCGTGAGGTGTCGGCTTAAGTGCCATAACGAG

CGCAACCCTTGTGGTCAGTTACTAACAGGTAATGCTGAGGACTCTGGCCA

GACTGCCATCGTAAGATGTGAGGAAGGCGGGGATGACGTCAAATCAGCAC

GGCCCTTACGTCCGGGGCTACACACGTGTTACAATGGGAGGTACAGAAGG

CTGCGACCCGGCGACGGGCAGCTAATCCCAAAAGCCTCTCTCAGTTCGGA

CTGGAGTCTGCAACCCGACTCCACGAAGCTGGATTCGCTAGTAATCGCGC

ATCAGCCACGGCGCGGTGAATACGTTCCCGGGCCTTGTACACACCGCCCG

TCAAGCCATGAAAGCCGGGGGTACCTGAAGTGCGTAACCGCAAGGAGCGT

CCTAGGGTAAAACCGGTAATTGGGGCTAAGTCGTAACAAGGTAGCCGTAC

CGGAAGGTGCGGCTGGAACACCTCCTTT

Representative strain and is 16S ribosomal RNA sequence for the predetermined microbe *Simonsiella* (other strains/ species belonging to the same genus are also considered within scope of this disclosure)

>NR_025144.1 *Simonsiella muelleri*
ATCC 29453 16S ribosomal RNA,
partial sequence
ATTGAACGCTGGCGGCATGCTTTACACATGCAAGTCGGACGGCAGCGGGG

TAGTGCTTGCATTACTGCCGGCGAGTGGCGAACGGGTGAGTATAATATTG

GAACGTACCGAGTAATGGGGGATAACTATCCGAAAGGATGGCTAATACCG

CATACGTCCTGAGGGAGAAAGCGGGGGACAGGCAACTGCCTCGCGTTATT

TGAGCGGCCAATATCGGATTAGCTAGTTGGTGGGGTAAAGGCTTACCAAG

GCGACGATCCGTAGCGGGTCTGAGAGGATGATCCGCCACACTGGGACTGA

GACACGGCCCAGACTCCTACGGGAGGCAGCAGTGGGGAATTTTGGACAAT

GGGGGGAACCCTGATCCAGCCATGTCGCGTGTATGAAGAAGGCCTTAGGG

TTGTAAAGTACTTTTGTTAGGGAAGAAAAGGCATTTGCTAATATCAGATG

CTGATGACGGTACCTAAAGAATAAGCACCGGCTAACTACGTGCCAGCAGC

CGCGGTAATACGTAGGGTGCGAGCGTTAATCGGAATTACTGGGCGTAAAG

CGAGCGCAGACGGTTACTTAAGCAAGATGTGAAATCCCCGAGCTCAACTT

GGGAACTGCGTTTTGAACTGGGTAGCTAGAGTGTGTCAGAGGGGGGTAGA

ATTCCACGTGTAGCAGTGAAATGCGTAGAGATGTGGAGGAATACCGATGG

CGAAGGCAGCCCCCTGGGATAGCACTGACGTTCATGCTCGAAAGCGTGGG

TAGCAAACAGGATTAGATACCCTGGTAGTCCACGCCCTAAACGATGTCAA

TTAGCTGTTGGGGCACTAGATGCCTTAGTAGCGAAGCTAACGCGTGAAAT

TGACCGCCTGGGGAGTACGGTCGCAAGATTAAAACTCAAAGGAATTGACG

GGGACCCGCACAAGCGGTGGATGATGTGGATTAATTCGATGCAACGCGAA

GAACCTTACCTGGTCTTGACATGTACGGAATCTCTCAGAGACGGGAGAGT

GCCTTCGGGAGCCGTAACACAGGTGCTGCATGGCTGTCGTCAGCTCGTGT

CGTGAGATGTTGGGTTAAGTCCCGCAACGAGCGCAACCCTTGTCATTAGT

TGCCATCATTTGGTTGGGCACTCTAATGAGACTGCCGGTGACAAACCGGA

GGAAGGTGGGGATGACGTCAAGTCCTCATGGCCCTTATGACCAGGGCTTC

ACACGTCATACAATGGTCGGTACAGAGGGTAGCCAAGCCGCGAGGTGGAG

CCAATCCCAAAAAACCGATCGTAGTCCGGATTGCACTCTGCAACTCGAGT

GCATGAAGTCGGAATCGCTAGTAATCGCAGGTCAGCATACTGCGGTGAAT

ACGTTCCCGGGTCTTGTACACACCGCCCGTCACACCATGGGAGTGGGGGA

TACCAGAAGTAGGTAGAATAACCGCGAGGAGTTCGCTTACCACGGTATGC

TTCATGACTGGGGTG

Representative strain and its 16S ribosomal RNA sequence for the predetermined microbe *Massiliprevotella* (other strains/species belonging to the same genus are also considered within scope of this disclosure)

>NR_147404.1 *Massiliprevotella massiliensis*
strain Marseille-P2439 16S ribosomal RNA,
partial sequence
AGAGTTTGATCCTGGCTCAGGATGAACGCTAGCTACAGGCTTAACACATG

CAAGTCGAGGGGAAACGATAGGGAAAGCTTGCTTTYCYTAGGCGTCGACC

-continued

GGCGCACGGGTGAGTAACGCGTATCCAACCTGCCCATGTCTGGGGAATAA

CCCGTCGAAAGGCGGACTAACTCCCCATGGTCTCCGATGAGGACATCTGA

ATTGGAGTAAAGCTTCGCGGACATGGATGGGGATGCGTCTGATTAGGTAG

TAGGCGGGGTAACGGCCCACCTAGCCTACGATCAGTAGGGGTTCTGAGAG

GAAGGTCCCCCACATTGGAACTGAGACACGGTCCAAACTCCTACGGGAGG

CAGCAGTGAGGAATATTGGTCAATGGACGAGAGTCTGAACCAGCCAAGTA

GCGTGCAGGATGACGGCCCTATGGGTTGTAAACTGCTTTTGCGCGGGGAT

AACACCCTCCACGTGCTGGAGGTCTGCAGGTACCGCGCGAATAAGGACCG

GCTAATTCCGTGCCAGCAGCCGCGGTAATACGGAAGGTCCGGGCGTTATC

CGGATTTATTGGGTTTAAAGGGAGCGTAGGCCGTGAGGTAAGCGTGTTGT

GAAATGTAGGCGCCCAACGTCTGCACTGCAGCGCGAACTGCCCCACTTGA

GTGCGCGCAACGCCGGCGGAACTCGTCGTGTAGCGGTGAAATGCTTAGAT

ATGACGAAGAACCCCGATTGCGAAGGCAGCTGGGGGGAGCGTAACTGACG

CTGAAGCTCGAAAGCGCGGGTATCGAACAGGATTAGATACCCTGGTAGTC

CGCGCGGTAAACGATGGATGCCCGCTGTGGCGCGCCTGGCGTGCCGCGGC

TAAGCGAAAGCATTAAGCATCCCACCTGGGGAGTACGCCGGCAACGGTGA

AACTCAAAGGAATTGACGGGGGCCCGCACAAGCGGAGGAACATGTGGTTT

AATTCGATGATACGCGAGGAACCTTACCCGGGCTTGAACTGCAGGAGAAC

GATTCAGAGATGATGAGGTCCTTCGGGACTCCTGTGGAGGTGCTGCATGG

TTGTCGTCAGCTCGTGCCGTGAGGTGTCGGCTTAAGTGCCATAACGAGCG

CAACCCCTCTCCGTAGTTGCCATCGGGTAATGCCGGGCACTCTGCGGACA

CTGCCACCGTAAGGTGTGAGGAAGGTGGGGATGACGTCAAATCAGCACGG

CCCTTACGTCCGGGGCCACACACGTGTTACAATGGCCGTCACAGAGGGGA

GCCGGGCGACCGGCTCATGATCCTTAAAAACGGTCTCAGTTCGGACTGGG

GTCTGCAACCCGACCCCACGAAGCTGGATTCGCTAGTAATCGCGCATCAG

CCATGGCGCGGTGAATACGTTCCCGGGCCTTGTACACACCGCCCGTCAAG

CCATGAAAGCCGGGGGCGCCTGAAGTCCGTGACCGCAAGGATCGGCCTAG

GGCGAAACTGGTGATTGGGGCTAAGTCGTAACAAGGTAGCCGT

Representative strain and its 16S ribosomal RNA sequence for the predetermined microbe *Streptobacillus* (other strains/species belonging to the same genus are also considered within scope of this disclosure)

>NR_145915.1 *Streptobacillus notomytis*
strain AHL 370-1 16S ribosomal RNA,
partial sequence
AGAGTTTGATCCTGGCTCAGGATGAACGCTGACAGAATGCTTAACACATG

CAAATCTATGTTAATTATGTAAGCTTGCTTAGATAAGAGACATGGTGGAC

TGGTGAGTAACGTGTAAAGAACTTACCTCTTAGACTGGGATAACCATTAG

AAATGATGGATAATACTAGATATTATTAGAAGTGGGCATCTACTTTTAAT

GAAAGGAGAGATTGCTAAGAGAGAGCTTTGCATCCTATTAGCTAGTTGGT

GGGGTAAAGGCCTACCAAGGCGATGATAGGTAGCCGGCCCGAGAGGGTGA

ACGGCCACAAGGGGACTGAGATACGGCCCTTACTCCTACGGGAGGCAGCA

GTGGGGAATATTGGACAATGGAGGAAACTCTGATCCAGCAATTCTGTGTG

-continued

CACGAAGAAGGTTTTCGGATTGTAAAGTGCTTTCAGTAGGGAAGAAGAAA

GTGACGGTACCTACAGAAGAAGCGACGGCTAAATACGTGCCAGCAGCCGC

GGTAATACGTATGTCGCAAGCGTTATCCGGAATTATTGGGCTTAAAGGGC

ATCTAGGCGGTCTAACAAGTTGAAGGTGAAAAGCTGTGGCTCAACCATAG

TCTTGCCTACAAAACTGTCGACTAGAGTACTGGAAAGGTGGGTGGAACT

ACACGAGTAGAGGTGAAATTCGTAGATATGTGTAGGAATGCCGATGATGA

AGATAACTCACTGGACAGAAACTGACGCTGAAGTGCGAAAGCTAGGGGAG

CAAACAGGATTAGATACCCTGGTAGTCCTAGCTGTAAACGATGATCACTG

GGTGTGGGGGTATAAGCCTCTGTGCCGAAGCAAAAGCGATAAGTGATCCG

CCTGGGGAGTACGTACGCAAGTATGAAACTCAAAGGAATTGACGGGGACC

CGCACAAGTGGTGGAGCATGTGGTTTAATTCGACGCAACGCGAGGAACCT

TACCAGATCTTGACATACTCGGAATAAGATGGAAGCATCTTAGTGCCTTC

GGGAACCGAGATACAGGTGGTGCATGGCTGTCGACAGCTCGTGTCGTGAG

ATGTTGGGTTAAGTCCCGCAACGAGCGAAACCCCTATCATTAGTTGCCAT

CATTAAGTTGGGGACTCTAATGAAACTGCCCGCGACGAGCGGGAGGAAGG

TGGGGATGACGTCAAGTCATCATGCCCCTTATGATCTGGGCTACACACGT

GCTACAATGGGTAGTACAAAGAGGAGCTAAGCAGTGATGTGGAGCAAATC

TTAAAAGCTACTCTCAGTTCGGATTGAAGTCTGCAACTCGACTTCATGAA

GTTGGAATCACTAGTAATCGCAAATCAGCAATGTTGCGGTGAATACGTTC

TCGGGTCTTGTACACACCGCCCGTCACACCACGAGAGTTAGTTGCACCTG

AAGTTACTGGCCTAACCGTAAGGAGGGAAGTACCTAAGGTGTGATTAGTG

ATTGGGGTGAAGTCGTAACAAGGTA

Representative strain and its 16S ribosomal RNA sequence for the predetermined microbe *Rothia* (other strains/species belonging to the same genus are also considered within scope of this disclosure)

>NR_044025.1 *Rothia halotolerans* strain YIM
90716 16S ribosomal RNA, complete sequence
AGAGATTAGAGTTTGATCCTGGCTCAGGACGAACGCTGGCGGCGTGCTTA

ACACATGCAAGTCGAACGCTGAAGCACCCAGCTTGCTGGGTGTGGATGAG

TGGCGAACGGGTGAGTAATACGTGAGTGACCTTCCCTTGACTCTGGGATA

AGCCCGGGAAACTGGGTCTAATACCGGATATGCACTATCACCTGCCTGGG

TGGTGGTGGAAAGGGTTTTGTACTGGTCTTGGATGGGCTCACGGCCTATC

AGCTAGTTGGTGAGGTAATGGCTTACCAAGGCGACGACGGGTAGCCGGCC

TGAGAGGGTGACCGGCCACACTGGGACTGAGACACGGCCCAGACTCCTAC

GGGAGGCAGCAGTGGGGAATATTGCACAATGGGCGCAAGCCTGATGCAGC

GACGCCGCGTGAGGGATGACGGCCTTCGGGTTGTAAACCTCTTTCAGCAG

GGAAGAAGCGAAAGTGACGGTACCTGCAGAAGAAGCGCCGGCTAACTACG

TGCCAGCAGCCGCGGTAATACGTAGGGCGCAAGCGTTGTCCGGAATTATT

GGGCGTAAAGAGCTCGTAGGCGGCTTGTCGCGTCTGCTGTGAAAGCCCGG

GGCTTAACCCCGTGGTGTGCAGTGGGTACGGGCAGGCTAGAGTGCAGTAG

GGGAGACTGGAATTCCTGGTGTAGCGGTGAAATGCGCAGATATCAGGAGG

-continued

AACACCGATGGCGAAGGCAGGTCTCTGGGCTGTTACTGACGCTGAGGAGC

GAAAGCATGGGGAGCGGACAGGATTAGATACCCTGGTAGTCCATGCCGTA

AACGTTGGGCACTAGGTGTGGGGGACATTCCACGTTTTCCGCGCCGTAGC

TAACGCATTAAGTGCCCCGCCTGGGGAGTACGGCCGCAAGGCTAAAACTC

AAAGGAATTGACGGGGGCCCGCACAAGCGGCGGAGCATGCGGATTAATTC

GATGCAACGCGAAGAACCTTACCAAGGCTTGACATACACTGGATCGCAGC

AGAGATGTTGTTTCCTCTTTGAGGCTGGTGTACAGGTGGTGCATGGTTGT

CGTCAGCTCGTGTCGTGAGATGTTGGGTTAAGTCCCGCAACGAGCGCAAC

CCTCGTTCTATGTTGCCAGCACGTGATGGTGGGGACTCATAGGAGACTGC

CGGGGTCAACTCGGAGGAAGGTGGGGATGACGTCAAATCATCATGCCCCT

TATGTCTTGGGCTTCACGCATGCTACAATGGCCGGTACAATGGGTTGCGA

TACTGTGAGGTGGAGCTAATCCCAAAAAGCCGGTCTCAGTTCGGATTGGG

GTCTGCAACTCGACCCCATGAAGTCGGAGTCGCTAGTAATCGCAGATCAG

CAACGCTGCGGTGAATACGTTCCCGGGCCTTGTACACACCGCCCGTCAAG

TCACGAAAGTTGGTAACACCCGAAGCCGATGGCCTAACCCTTGTGGAGGG

AGTCGTCGAAGGTGGGACTGGCGATTGGGACTAAGTCGTAACAAGGTAGC

CGTACCGGAAGGTGCGGCTGGATCACCTCCTAA

Representative strain and its 16S ribosomal RNA sequence for the predetermined microbe *Slackia* (other strains/species belonging to the same genus are also considered within scope of this disclosure)

>NR_112898.1 *Slackia piriformis* YIT 12062
16S ribosomal RNA, partial sequence
GATGAACGCTGGCGGCGTGCCTAACACATGCAAGTCGAACGGTTAAGGCG

CCTTCGGGCGCGCATAGAGTGGCGAACGGGTGAGTAACACGTGACCAACC

TGCCCCCTCCTCCGGGACAACCTCGGGAAACCGAGGCTAATACCGGATGG

TCCCGCCGGGCCGCATGGCCGGGGGGGGAAAGCCCAGGCGGGAGGGGATG

GGGTCGCGGCCCATCAGGTAGTAGGCGGGGTGACGGCCCACCTAGCTGAC

GACGGGTAGCCGCGCTGAGAGGCGGACCGGCCACATTGGGACTGAGACAC

GGCCCAGACTCCTACGGGAGGCAGCAGTGGGGAATTTTGCGCAATGGGGG

AAACCCTGACGCAGCAACGCCGCGTGCGGGACGAAGGCCTTCGGGTCGTA

AACCGCTTTCAGCAGGGAAGAAGAATGACGGTACCTGCAGAAGAAGCCCC

GGCTAACTACGTGCCAGCAGCCGCGGTAATACGTAGGGGGCGAGCGTTAT

CCGGATTCATTGGGCGTAAAGCGCGCGTAGGCGTCCCTTCAAGCGGCACC

GTCGAAGCCGGGGGCTCAACCCCCGGAAGCGGGCCGAACTGGGGGGATCG

AGTGCGGTAGGGGAAGGCGGAATTCCCGGTGTAGCGGTGAAATGCGCAGA

TATCGGGAAGAACACCGACGGCGAAGGCAGCCTTCTGGGCCGCCACTGAC

GCTGAGGCGCGAAAGCTGGGGGAGCGAACAGGATTAGATACCCTGGTAGT

CCCAGCCGTAAACGATGGGCGCTAGGTGTGGGGGGAGATGTCCCTCCGTG

CCGCAGCCAACGCATTAAGCGCCCCGCCTGGGGAGTACGGCCGCAAGGCT

AAAACTCAAAGGAATTGACGGGGGCCCGCACAAGCAGCGGAGCATGTGGC

TTAATTCGAAGCAACGCGAAGAACCTTACCAGGGCTTGACATCACCGTGA

-continued

GCCGCCGGAGACGGGGGGGCCGAAAGGAGCGGTGACAGGTGGTGCATGGC

TGTCGTCAGCTCGTGTCGTGAGATGTTGGGTTAAGTCCCGCAACGAGCGC

AACCCCCGCCGCGTGTTGCCAGCATTGAGTTGGGCACTCGCGCGGGACTG

CCGGCGTCAAGCCGGAGGAAGGTGGGGACGACGTCAAGTCATCATGCCCC

TCATGCCCTGGGCTGCACACGTGCTACAATGGCCGGTACAGCGGGCTGCG

ACGCCGCGAGGCGGAGCGAATCCCACAAAGCCGGCCCCAGTTCGGACCGC

AGGCTGCAACCCGCCTGCGCGAAGCCGGAGTTGCTAGTAATCGCGGATCA

GCATGCCGCGGTGAATACGTTCCCGGGCCTTGTACACACCGCCCGTCACA

CCACCCGAGTCGTCTGCACCCGAAGCCGCCGGCCGAACCCGCAAGGGGCG

GAGGCGTCGAAGGTGTGGAGGGTGAGGGGGGTGAAGTCGTAACAAGGTAG

CCGTACCGGAAGG

The representative sequences corresponding to the list of predetermined microbes associated with the stool samples are shared below:

Representative strain and its 16S ribosomal RNA sequence for the predetermined microbe *Oscillibacter* (other strains/species belonging to the same genus are also considered within scope of this disclosure)

>NR_074793.2 *Oscillibacter valericigenes* strain
Sjm18-20 16S ribosomal RNA, complete sequence
TTTATAGAGAGTTTGATCCTGGCTCAGGACGAACGCTGGCGGCGTGCTT

AACACATGCAAGTCGAACGGA

GCACCCTTGATTGAGGTTTCGGCCAAATGAGAGGAATGCTTAGTGGCGG

ACTGGTGAGTAACGCGTGAGG

AACCTGCCTTTCAGAGGGGGACAACAGTTGGAAACGACTGCTAATACCG

CATGATACATTTGGGCGACAT

CGCTTGAATGTCAAAGATTTATCGCTGAAAGATGGCCTCGCGTCTGATT

AGATAGTTGGTGAGGTAACGG

CCCACCAAGTCGACGATCAGTAGCCGGACTGAGAGGTTGACCGGCCACA

TTGGGACTGAGATACGGCCCA

GACTCCTACGGGAGGCAGCAGTGGGGAATATTGGGCAATGGACGCAAGT

CTGACCCAGCAACGCCGCGTG

AAGGAAGAAGGCTTTCGGGTTGTAAACTTCTTTTAAGGGGGAAGAGTAG

AAGACGGTACCCCTTGAATAA

GCCACGGCTAACTACGTGCCAGCAGCCGCGGTAATACGTAGGTGGCAAG

CGTTGTCCGGATTTACTGGGT

GTAAAGGGCGTGTAGCCGGGAAGGTAAGTCAGATGTGAAATCTGGGGGC

TCAACCTCCAAACTGCATTTG

AAACTACTTTTCTTGAGTATCGGAGAGGTAATCGGAATTCCTTGTGTAG

CGGTGAAATGCGTAGATATAA

GGAAGAACACCAGTGGCGAAGGCGGATTACTGGACGACAACTGACGGTG

AGGCGCGAAAGCGTGGGGAGC

AAACAGGATTAGATACCCTGGTAGTCCACGCTGTAAACGATCAATACTA

-continued

GGTGTGCGGGGACTGACCCCC

TGCGTGCCGCAGTTAACACAATAAGTATTGCACCTGGGGAGTACGATCG

CAAGGTTGAAACTCAAAGGAA

TTGACGGGGGCCCGCACAAGCGGTGGATTATGTGGTTTAATTCGAAGCA

ACGCGAAGAACCTTACCAGGA

CTTGACATCCTACTAACGAGGTAGAGATACGTCAGGTGCCCTTCGGGGA

AAGTAGAGACAGGTGGTGCAT

GGTTGTCGTCAGCTCGTGTCGTGAGATGTTGGGTTAAGTCCCGCAACGA

GCGCAACCCCTATTGTTAGTT

GCTACGCAAGAGCACTCTAGCGAGACTGCCGTTGACAAAACGGAGGAAG

GTGGGGACGACGTCAAATCAT

CATGCCCCTTATGTCCTGGGCTACACACGTAATACAATGGCGGTCAACA

GAGGGATGCAAAGCCGTGAGG

TGGAGCGAACCCCTAAAAGCCGTCTCAGTTCGGATCGCAGGCTGCAACT

CGCCTGCGTGAAGTCGGAATC

GCTAGTAATCGCGGATCAGAATGCCGCGGTGAATACGTTCCCGGGCCTT

GTACACACCGCCCGTCACACC

ATGAGAGTCGGGAACACCCGAAGTCCGTAGCCTAACAGCAATGAGGGCG

CGGCCGAAGGTGGGTTTGATA

ATTGGGGTGAAGTCGTAACAAGGTAGCCGTATCGGAAGGTGCGGCTGGA

TCACCTCCTTT

Representative strain and its 16S ribosomal RNA sequence for the predetermined microbe *Cuneatibacter* (other strains/species belonging to the same genus are also considered within scope of this disclosure)

>NR_144608.1 *Cuneatibacter caecimuris* strain
BARN-424-CC-10 16S ribosomal RNA, partial
sequence
AGAGTTTGATCCTGGCTCAGGATGAACGCTGGCGGCGTGCTTAACACAT

GCAAGTCGAACGAAGCAGTTG

CGAGGAAGTTTTCGGATGGAATTGCGATTGACTGAGTGGCGGACGGGTG

AGTAACGCGTGGGTAACCTGC

CTCACACAGGGGGATAACAGTTAGAAATGACTGCTAATACCGCATAACC

CGCTAGGGCCGCATGGCCCGG

ACGGAAAAGAAATATCGGTGTGAGATGGACCCGCGTCTGATTAGCTGGT

TGGTAGGGTAACGGCCTACCA

AGGCGACGATCAGTAGCCGACTTGAGAGAGTGATCGGCCACATTGGGAC

TGAGACACGGCCCAAACTCCT

ACGGGAGGCAGCAGTGGGGAATATTGCACAATGGGGGAAACCCTGATGC

AGCGACGCCGCGTGACTGAAG

AAGTACTTCGGTATGTAAAGGTCTATCAGCAGGGAAGAAGAAAGACGGT

ACCTGACTAAGAAGCCCCGGC

-continued
TAACTACGTGCCAGCAGCCGCGGTAATACGTAGGGGGCAAGCGTTATCC

GGATTTACTGGGTGTAAAGGG

AGCGTAGGCGGTAGCGCAAGTCAGAAGTGAAAGCCCGGGGCTCAACCCC

GCGGACTGCTTTTGAAACTGC

GTAACTGGAGTGCAGGAGAGGTAAGTGGAATTCCTAGTGTAGCGGTGAA

ATGCGTAGATATTAGGAGGAA

CACCAGTGGCGAAGGCGGCTTACTGGACTGTAACTGACGCTGAGGCTCG

AAAGCGTGGGGAGCAAACAGG

ATTAGATACCCTGGTAGTCCACGCTGTAAACGATGAATACTAGGTGTCG

GGGAGCAAAGCTCTTCGGTGC

CGTCGCAAACGCAGTAAGTATTCCACCTGGGGAGTACGTTCGCAAGAAT

GAAACTCAAAGGAATTGACGG

GGACCCGCACAAGCGGTGGAGCATGTGGTTTAATTCGAAGCAACGCGAA

GAACCTTACCTGCTCTTGACA

TCCCCCTGACGCAGAGGTAATGCTCTGTTTCTTTCGAGACAGGGGAGAC

AGGTGGTGCATGGTTGTCGTC

AGCTCGTGTCGTGAGATGTTGGGTTAAGTCCCGCAACGAGCGCAACCCT

TATCCTTAGTAGCCAGCAGGT

AGAGCTGGGCACTCTGGGGAGACTGCCGGGGATAACCCGGAGGAAGGTG

GGGATGACGTCAAATCATCAT

GCCCCTTATGAGCAGGGCTACACACGTGCTACAATGGCGTAAACAGAGG

GAAGCGAAGGGGTGACCTGAA

GCGAATCTCAAAAATAACGTCTCAGTTCGGATTGTAGTCTGCAACTCGA

CTACATGAAGCTGGAATCGCT

AGTAATCGCGAATCAGAATGTCGCGGTGAATACGTTCCCGGGTCTTGTA

CACACCGCCCGTCACACCATG

GGAGTCGGTAACGCCCGAAGCCAGTGACCTAACCTGAAAAGGGAGGAGC

TGTCGAAGGCGGGACTGGTAA

CTGGGGTGAAGTCGT

Representative strain and its 16S ribosomal RNA sequence for the predetermined microbe *Faecalibacterium* (other strains/species belonging to the same genus are also considered within scope of this disclosure)

>NR_028961.1 *Faecalibacterium prausnitzii* strain
ATCC 27768 16S ribosomal RNA, partial sequence
GATCCTGGCTCAGGCGAACGCTGGCGGCGCGCCTAACACATGCAAGTC

GAACGAGCGAGAGAGAGCTTGC

TTTCTCAAGCGAGTGGCGAACGGGTGAGTAACGCGTGAGGAACCTGCC

TCAAAGAGGGGGACAACAGTTG

GAAACGACTGCTAATACCGCATAAGCCCACGACCCGGCATCGGGTAGA

GGGAAAAGGAGCAATCCGCTTT

GAGATGGCCTCGCGTCCGATTAGCTAGTTGGTGAGGTAACGGCCCACC

-continued

```
AAGGCGACGATCGGTAGCCGGA

CTGAGAGGTTGAACGGCCACATTGGGACTGAGACACGGCCCAGACTCC

TACGGGAGGCAGCAGTGGGGAA

TATTGCACAATGGGGGAAACCCTGATGCAGCGACGCCGCGTGGAGGAA

GAAGGTCTTCGGATTGTAAACT

CCTGTTGTTGAGGAAGATAATGACGGTACTCAACAAGGAAGTGACGGC

TAACTACGTGCCAGCAGCCGCG

GTAAAACGTAGGTCACAAGCGTTGTCCGGAATTACTGGGTGTAAAGGG

AGCGCAGGCGGGAAGGCAAGTT

GGAAGTGAAATCCATGGGCTCAACCCATGAACTGCTTTCAAAACTGTT

TTTCTTGAGTAGTGCAGAGGTA

GGCGGAATTCCCGGTGTAGCGGTGGAATGCGTAGATATCGGGAGGAAC

ACCAGTGGCGAAGGCGGCCTAC

TGGGCACCAACTGACGCTGAGGCTCGAAAGTGTGGGTAGCAAACAGGA

TTAGATACCCTGGTAGTCCACA

CTGTGGCCGATGTTTACTAGGTGTTGGAGGATTGACCCCTTCAGTGCC

GCAGTTAACACAATAAGTAATC

CACCTGGGGAGTACGACCGCAAGGTTGAAACTCAAAGGAATTGACGGG

GGCCCGCACAAGCAGTGGAGTA

TGTGGTTTAATTCGACGCAACGCGAAGAACCTTACCAAGTCTTGACAT

CCTGCGACGCACATAGAAATAT

GTGTTTCCTTCGGGACGCAGAGACAGGTGGTGCATGGTTGTCGTCAGC

TCGTGTCGTGAGATGTTGGGTT

AAGTCCCGCAACGAGCGCAACCCTTATGGTCAGTTACTACGCAAGAGG

ACTCTGGCCAGACTGCCGTTGA

CAAAACGGAGGAAGGTGGGGATGACGTCAAATCATCATGCCCTTTATG

ACTTGGGCTACACACGTACTAC

AATGGCGTTAAACAAAGAGAAGCAAGACCGCGAGGTGGAGCAAAACTC

AGAAACAACGTCCCAGTTCGGA

CTGCAGGCTGCAACTCGCCTGCACGAAGTCGGAATTGCTAGTAATCGC

AGATCAGCATGCTGCGGTGAAT

ACGTTCCCGGGCCTTGTACACACCGCCCGTCACACCATGAGAGCCGGG

GGGACCCGAAGTCGGTAGTCTA

ACCGCAAGGAGGACGCCGCCGAAGGTAAAACTGGTGATTGGGGTGAAG

TCGTAACAAGGTAC
```

Representative strain and is 16S ribosomal RNA sequence for the predetermined microbe *Pseudoflavonifractor* (other strains/species belonging to the same genus are also considered within scope of this disclosure)

>NR_147370.1 *Pseudoflavonifractor phocaeensis* strain Marseille-P3064 16S ribosomal RNA, partial sequence

```
AGAGTTTGATCCTGGCTCAGGATGAACGCTGGCGGCGTRCTTAACACAT

GCAAGTCGAACGGAGTGCCTA

TGAAAGAGGATTCGTCCAATTGATTAGGTTACTTAGTGGCGGACGGGTG

AGTAACGCGTGAGGAACCTGC

CTCGGAGTGGGGAATAACAATCCGAAAGGATTGCTAATACCGCATGATG

CAGTTGGGCCGCATGGCTCTG

ACTGCCAAAGATTTATCGCTCTGAGATGGCCTCGCGTCTGATTAGCTAG

TTGGCGGGGTAACGGCCCACC

AAGGCGACGATCAGTAGCCGGACTGAGAGGTTGACCGGCCACATTGGGA

CTGAGACACGGCCCAGACTCC

TACGGGAGGCAGCAGTGGGGAATATTGGGCAATGGGCGCAAGCCTGACC

CAGCAACGCCGCGTGAAGGAA

GAAGGCTTTCGGGTTGTAAACTTCTTTTCTCAGGGACGAAGAAAATGAC

GGTACCTGAGGAATAAGCCAC

GGCTAACTACGTGCCAGCAGCCGCGGTAATACGTAGGTGGCAAGCGTTA

TCCGGATTTACTGGGTGTAAA

GGGCGTGTAGGCGGGATTGCAAGTCAGGCGTGAAAACTATGGGCTTAAC

CCATAGCCTGCGTTTGAAACT

GTAGTTCTTGAGTGCTGGAGAGGCAATCGGAATTCCGTGTGTAGCGGTG

AAATGCGTAGATATACGGAGG

AACACCAGTGGCGAAGGCGGATTGCTGGACAGTAACTGACGCTGAGGCG

CGAAAGCGTGGGGAGCAAACA

GGATTAGATACCCTGGTAGTCCACGCCGTAAACGATGGATACTAGGTGT

GGGGGGTCTGACCCCCTCCGT

GCCGCAGTTAACACAATAAGTATCCCACCTGGGGAGTACGATCGCAAGG

TTGAAACTCAAAGGAATTGAC

GGGGGCCCGCACAAGCGGTGGAGTATGTGGTTTAATTCGAAGCAACGCG

AAGAACCTTACCAGGGCTTGA

CATCCAACTAACGAAGCAGAGATGCATTAGGTGCCCTTCGGGGAAAGTT

GAGACAGGTGGTGCATGGTTG

TCGTCAGCTCGTGTCGTGAGATGTTGGGTTAAGTCCCGCAACGAGCGCA

ACCCTTATTGTTAGTTGCTAC

GCAAGAGCACTCTAGCGAGACTGCCGTTGACAAAACGGAGGAAGGTGGG

GACGACGTCAAATCATCATGC

CCCTTATGTCCTGGGCCACACACGTACTACAATGGTGGTTAACAGAGGG

AGGCAATACCGCGAGGTGGAG

CAAATCCCTAAAAGCCATCCCAGTTCGGATTGCAGGCTGAAACCCGCCT

GTATGAAGTTGGAATCGCTAG

TAATCGCGGATCAGCATGCCGCGGTGAATACGTTCCCGGGCCTTGTACA
```

-continued
CACCGCCCGTCACACCATGAG

AGTCGGGAACACCCGAAGTCCGTAGCCTAACAGCAATGGGGGCGCGGCC

GAAGGTGGGTTCGATAATTGG

GGTGAAGTCGTAACAAGGTAGCCGT

Representative strain and its 16S ribosomal RNA sequence for the predetermined microbe *Gordonibacter* (other strains/species belonging to the same genus are also considered within scope of this disclosure)

>NR_134044.1 *Gordonibacter urolithinfaciens*
strain CEBAS 1/15P 16S ribosomal RNA, partial
sequence
TGCTCAGGATGAACGCTGGCGGCGTGCCTAACACATGCAAGTCGAACG

ATTAAGGCGCCTTCGGGCGCGA

ATAGAGTGGCGAACGGGTGAGTAACACGTGACCAACCTGCCCCCCTCC

CCGGGATAACGCGAGGAAACCC

GCGCTAATACCGGATACTCCGCCCCTCCCGCATGGGAGGGGGGGAAA

GCCCCGACGGAGGGGGATGGGG

TCGCGGCCCATTAGGTAGACGGCGGGGCAACGGCCCACCGTGCCTGCG

ATGGGTAGCCGGGTTGAGAGAC

CGACCGGCCACATTGGGACTGAGATACGGCCCAGACTCCTACGGGAGG

CAGCAGTGGGGAATTTTGCGCA

ATGGGGGGAACCCTGACGCAGCAACGCCGCGTGCGGGACGAAGGCCTT

CGGGTTGTAAACCGCTTTCAGC

AGGGAAGAAGTTGACGGTACCTGCAGAAGAAGCCCCGGCTAACTACGT

GCCAGCAGCCGCGGTAATACGT

AGGGGGCGAGCGTTATCCGGATTCATTGGGCGTAAAGCGCGCGTAGGC

GGCCCGTCAAGCGGAACCTCTA

ACCCGAGGGCTCAACCCCCGGCCGGGTTCCGAACTGGCAGGCTCGAGT

CTGGTAGAGGAAGATGGAATTC

CCGGTGTAGCGGTGGAATGCGCAGATATCGGGAAGAACACCGATGGCG

AAGGCAGTCTTCTGGGCCGCGA

CTGACGCTGAGGCGCGAAAGCTGGGGGAGCGAACAGGATTAGATACCC

TGGTAGTCCCAGCCGTAAACGA

TGGGCGCTAGGTGTGGGGGGATCATCCCTCCGTGCCGCAGCCAACGCA

TTAAGCGCCCCGCCTGGGGAGT

ACGGCCGCAAGGCTAAAACTCAAAGGAATTGACGGGGGCCCGCACAAG

CAGCGGAGCATGTGGCTTAATT

CGAAGCAACGCGAAGAACCTTACCAGGGCTTGACATGCTGGTGAAGCC

GGGGAAACCCGGTGGCCGAGAG

GAGCCAGCGCAGGTGGTGCATGGCTGTCGTCAGCTCGTGTCGTGAGAT

GTTGGGTTAAGTCCCGCAACGA

GCGCAACCCCTGCCATATGTTGCCAGCATTCAGTTGGGGACTCATATG

GGACTGCCGGCGTCAAGCCGGA

-continued
GGAAGGTGGGGACGACGTCAAGTCATCATGCCCTTTATGCCCTGGGCT

GCACACGTGCTACAATGGCCGG

TACAACGGGCCGCGACCTGGCGACAGGAAGCGAATCCCTCAAAGCCGG

CCCCAGTTCGGATCGGAGGCTG

CAACCCGCCTCCGTGAAGTCGGAGTTGCTAGTAATCGCGGATCAGCAT

GCCGCGGTGAATACGTTCCCGG

GCCTTGTACACACCGCCCGTCACACCACCCGAGTCGTCTGCACCCGAA

GCCGCCGGCCGAACCCGCAAGG

GGCGGAGGCGTCGAAGGTGTGGAGGGTAAGGGGGGTGAAGTCGTAACA

AGGTAGCCGTACCGGAAGGTGC

GGCTGGA

Representative strain and its 16S ribosomal RNA sequence for the predetermined microbe *Neisseria* (other strains/species belonging to the same genus are also considered within scope of this disclosure)

>NR_116766.1 *Neisseria wadsworthii* 9715 strain
WC 05-9715 16S ribosomal RNA, partial sequence
ATTGAACGCTGGCGGCATGCTTTACACATGCAAGTCGAACGGCAGCGG

GGGAGAGCTTGCTTTCCTGCCG

GCGAGTGGCGAACGGGTGAGTAATGCATCGGAACGTACCGAGTAGTGG

GGGATAACTGTCCGAAAGGATG

GCTAATACCGCATACGCTTTGCGAAGGAAAGCGGGGGCTCTTAGGACC

TCGCGCTATTCGAGCGGCCGAT

GTCTGATTAGCTAGTTGGTGGGGTAAAGGCCTACCAAGGCGACGATCA

GTAGCGGGTCTGAGAGGATGAT

CCGCCACACTGGGACTGAGACACGGCCCAGACTCCTACGGGAGGCAGC

AGTGGGGAATTTTGGACAATGG

GGGGAACCCTGATCCAGCCATGCCGCGTGTCTGAAGAAGGCCTTCGGG

TTGTAAAGGACTTTTGTCAGGG

AAGAAAAGCTTCGGGTTAATACCCTGGAGTGATGACGGTACCTGAAGA

ATAAGCACCGGCTAACTACGTG

CCAGCAGCCGCGGTAATACGTAGGGTGCGAGCGTTAATCGGAATTACT

GGGCGTAAAGCGAGCGCAGACG

GTTACTTAAGCAGGATGTGAAATCCCCGGGCTCAACCTGGGAACTGCG

TTCTGAACTGGGTGACTAGAGT

ATGTCAGAGGGGGGTAGAATTCCACGTGTAGCAGTGAAATGCGTAGAG

ATGTGGAGGAATACCGATGGCG

AAGGCAGCCCCCTGGGATAATACTGACGTTCATGCTCGAAAGCGTGGG

TAGCAAACAGGATTAGATACCC

TGGTAGTCCACGCCCTAAACGATGTCAATTAGCTGTTGGGGCACTTGA

TGCTTTAGTAGCGTAGCTAACG

CGTGAAATTGACCGCCTGGGGAGTACGGTCGCAAGATTAAAACTCAAA

-continued

GGAATTGACGGGGACCCGCACA

AGCGGTGGATGATGTGGATTAATTCGATGCAACGCGAAGAACCTTACC

TGGTCTTGACATGTACGGAATC

CTCCGGAGACGGAGGAGTGCCTTCGGGAGCCGTAACACAGGTGCTGCA

TGGCTGTCGTCAGCTCGTGTCG

TGAGATGTTGGGTTAAGTCCCGCAACGAGCGCAACCCTTGTCATTAGT

TGCCATCATTTAGTTGGGCACT

CTAATGAGACTGCCGGTGACAAACCGGAGGAAGGTGGGGATGACGTCA

AGTCCTCATGGCCCTTATGACC

AGGGCTTCACACGTCATACAATGGTCGGTACAGAGGGTAGCCAAGCCG

CGAGGTGGAGCCAATCCCACAA

AACCGATCGTAGTCCGGATTGCACTCTGCAACTCGAGTGCATGAAGTC

GGAATCGCTAGTAATCGCAGGT

CAGCATACTGCGGTGAATACGTTCCCGGGTCTTGTACACACCGCCCGT

CACACCATGGGAGTGGGGGATA

CCAGAAGTAGGTAGGGTAACCGCAAGGAGCCCGCTTACCACGGTATGC

TTCATGACTGGGGTG

Representative strain and its 16S ribosomal RNA sequence for the predetermined microbe *Fusobacterium* (other strains/species belonging to the same genus are also considered within scope of this disclosure)

>NR_146837.2 *Fusobacterium gastrosuis* strain
CDW1 16S ribosomal RNA, complete sequence
TGAACGAAGAGTTTGATCCTGGCTCAGGATGAACGCTGACAGAATGCTT

AACACATGCAAGTCTACTTGA

ACTTCGGTTTGGGTGGCGGACGGGTGAGTAACGCGTAAAGAACTTGCCT

CACAGACTGGGACAACATTTG

GAAACGAATGCTAATACCGGATATTATGAGATATGCGCATGCATAACTT

ATGAAAGCTATATGCGCTGTG

AGAGAGCTTTGCGTCCCATTAGCTAGTTGGAGAGGTAACGGCTCACCAA

GGCGATGATGGGTAGCCGGCC

TGAGAGGGTGAACGGCCACAAGGGGACTGAGACACGGCCCTTACTCCTA

CGGGAGGCAGCAGTGGGGAAT

ATTGGACAATGGACCAAGAGTCTGATCCAGCAATTCTGTGTGCACGATG

AAGTTTTTCGGAATGTAAAGT

GCTTTCAGTTGGGAAGAAGAAAGTGACGGTACCAACAGAAGAAGCGACG

GCTAAATACGTGCCAGCAGCC

GCGGTAATACGTATGTCGCAAGCGTTATCCGGATTTATTGGGCGTAAAG

CGCGTCTAGGCGGCATAGTAA

GTCTGATGTGAAAATGCGGGGCTCAACTCCGTATTGCGTTGGAAACTGC

TATGCTAGAGTACTGGAGAGG

TAAGCGGAACTACAAGTGTAGAGGTGAAATTCGTAGATATTTGTAGGAA

-continued

TGCCGATGGGGAAGCCAGCTT

ACTGGACAGATACTGACGCTAAAGCGCGAAAGCGTGGGTAGCAAACAGG

ATTAGATACCCTGGTAGTCCA

CGCCGTAAACGATGATTACTAGGTGTTGGGGGTCGAACCTCAGCGCCCA

AGCTAACGCGATAAGTAATCC

GCCTGGGGAGTACGTACGCAAGTATGAAACTCAAAGGAATTGACGGGGA

CCCGCACAAGCGGTGGAGCAT

GTGGTTTAATTCGACGCAACGCGAGGAACCTTACCAGCGTTTGACATCC

TAAGAAGTCTATAGAGATATG

GATGTGCTCCTTCGGGAGAACTTAGTGACAGGTGGTGCATGGCTGTCGT

CAGCTCGTGTCGTGAGATGTT

GGGTTAAGTCCCGCAACGAGCGCAACCCCTTTCGTATGTTACCATCATT

AAGTTGGGGACTCATGCGATA

CTGCCTGCGATGAGCAGGAGGAAGGTGGGGATGACGTCAAGTCATCATG

CCCCTTATACGCTGGGCTACA

CACGTGCTACAATGGGTAGTACAGAGAGAAGCGAAACTGCGAGGTGGAG

CAAATCTCAGAAAACTATTCT

TAGTTCGGATTGTACTCTGCAACTCGAGTACATGAAGTTGGAATCGCTA

GTAATCGCAAATCAGCTATGT

TGCGGTGAATACGTTCTCGGGTCTTGTACACACCGCCCGTCACACCACG

AGAGTTGGTTGCACCTGAAGT

AACAGGCCTAACCGTAAGGAGGGATGTTCCGAGGGTGTGATTAGCGATT

GGGGTGAAGTCGTAACAAGGT

ATCCGTACGGGAACGTGCGGATGGATCACCTCCTTT

Representative strain and its 16S ribosomal RNA sequence for the predetermined microbe *Lactococcus* (other strains/species belonging to the same genus are also considered within scope of this disclosure)

>NR_174267.1 *Lactococcus allomyrinae* strain
1JSPR-7 16S ribosomal RNA, complete sequence
TTATTTGAGAGTTTGATCCTGGCTCAGGACGAACGCTGGCGGCGTGCCT

AATACATGCAAGTTGAGCGCT

GAAGGAAGGTACTTGTACCGACTGGAAGAGCAGCGAACGGGTGAGTAAC

GCGTGGGGAATCTGCCTTTGA

GCGGGGGACAACATTTGGAAACGAATGCTAATACCGCATAACAACTTTA

AACACAAGTTAAAAGTTTGAA

AGATGCAAAAGCATCACTCAGAGATGATCCCGCGTTGTATTAGCTAGTT

GGTGAGGTAAAGGCTCACCAA

GGCGATGATACATAGCCGACCTGAGAGGGTGATCGGCCACATTGGGACT

GAGACACGGCCCAAACTCCTA

CGGGAGGCAGCAGTAGGGAATCTTCGGCAATGGACGAAAGTCTGACCGA

GCAACGCCGCGTGAGTGAAGA

-continued

AGGTTTTCGGATCGTAAAACTCTGTTGTTAGAGAAGAACGTGTGTGGGA

GTGGAAAATCCATGCAGTGAC

GGTATCTAACCAGAAAGGGACGGCTAACTACGTGCCAGCAGCCGCGGTA

ATACGTAGGTCCCGAGCGTTG

TCCGGATTTATTGGGCGTAAAGCGAGCGCAGGTGGTTTATTAAGTCTGG

TGTAAAAGGCAGTGGCTCAAC

CATTGTATGCATTGGAAACTGGTAGACTTGAGTGCAGGAGAGGAGAGTG

GAATTCCATGTGTAGCGGTGA

AATGCGTAGATATATGGAGGAACACCGGTGGCGAAAGCGGCTCTCTGGC

CTGTAACTGACACTGAGGCTC

GAAAGCGTGGGGAGCAAACAGGATTAGATACCCTGGTAGTCCACGCCGT

AAACGATGAGTGCTAGATGTA

GGAAGCTATAAGTTTTCTGTATCGCAGCTAACGCAATAAGCACTCCGCC

TGGGGAGTACGACCGCAAGGT

TGAAACTCAAAGGAATTGACGGGGGCCCGCACAAGCGGTGGAGCATGTG

GTTTAATTCGAAGCAACGCGA

AGAACCTTACCAGGTCTTGACATCCCGATGCTATCCTTAGAGATAAGGA

GTTACTTCGGTACATCGGTGA

CAGGTGGTGCATGGTTGTCGTCAGCTCGTGTCGTGAGATGTTGGGTTAA

GTCCCGCAACGAGCGCAACCC

CTATTACTAGTTGCCATCATTAAGTTGGGCACTCTAGTGAGACTGCCGG

TGATAAACCGGAGGAAGGTGG

GGATGACGTCAAATCATCATGCCCCTTATGACCTGGGCTACACACGTGC

TACAATGGATGGTACAACGAG

TCGCGAGACAGTGATGTTTAGCTAATCTCTTAAAACCATTCTCAGTTCG

GATTGTAGGCTGCAACTCGCC

TACATGAAGTCGGAATCGCTAGTAATCGCGGATCAGCACGCCGCGGTGA

ATACGTTCCCGGGCCTTGTAC

ACACCGCCCGTCACACCACGGGAGTTGGGAGTACCCGAAGTAGGTTGCC

TAACCGCAAGGAGGGCGCTTC

CTAAGGTAAGACCGATGACTGGGGTGAAGTCGTAACAAGGTAGCCGTAT

CGGAAGGTGCGGCTGGATCAC

CTCCTTT

Representative strain and its 16S ribosomal RNA sequence for the predetermined microbe *Lactobacillus* (other strains/species belonging to the same genus are also considered within scope of this disclosure)

>NR_180521.1 *Lactobacillus mulieris* strain
c10Ua161M 16S ribosomal RNA, complete
sequence
CAAAATGAGAGTTTGATCCTGGCTCAGGACGAACGCTGGCGGCGT

GCCTAATACATGCAAGTCGAGCGAG

-continued

CTTGCCTATTGAAATTCTTCGGAATGGACATAGATACAAGCTAGC

GGCGGATGGGTGAGTAACGCGTGGG

TAACCTGCCCTTAAGTCTGGGATACCATTTGGAAACAGATGCTAA

TACCGGATAAAAGCTACTTTCGCAT

GAAAGAAGTTTAAAAGGCGGCGTAAGCTGTCGCTAAAGGATGGAC

CTGCGATGCATTAGCTAGTTGGTAA

GGTAACGGCTTACCAAGGCGATGATGCATAGCCGAGTTGAGAGAC

TGATCGGCCACATTGGGACTGAGAC

ACGGCCCAAACTCCTACGGGAGGCAGCAGTAGGGAATCTTCCACA

ATGGACGCAAGTCTGATGGAGCAAC

GCCGCGTGAGTGAAGAAGGTTTTCGGATCGTAAAGCTCTGTTGTT

GGTGAAGAAGGATAGAGGTAGTAAC

TGGCCTTTATTTGACGGTAATCAACCAGAAAGTCACGGCTAACTA

CGTGCCAGCAGCCGCGGTAATACGT

AGGTGGCAAGCGTTGTCCGGATTTATTGGGCGTAAAGCGAGCGCA

GGCGGATTGATAAGTCTGATGTGAA

AGCCTTCGGCTCAACCGAAGAACTGCATCAGAAACTGTCAATCTT

GAGTGCAGAAGAGGAGAGTGGAACT

CCATGTGTAGCGGTGGAATGCGTAGATATATGGAAGAACACCAGT

GGCGAAGGCGGCTCTCTGGTCTGTA

ACTGACGCTGAGGCTCGAAAGCATGGGTAGCGAACAGGATTAGAT

ACCCTGGTAGTCCATGCCGTAAACG

ATGAGTGCTAAGTGTTGGGAGGTTTCCGCCTCTCAGTGCTGCAGC

TAACGCATTAAGCACTCCGCCTGGG

GAGTACGACCGCAAGGTTGAAACTCAAAGGAATTGACGGGGGCCC

GCACAAGCGGTGGAGCATGTGGTTT

AATTCGAAGCAACGCGAAGAACCTTACCAGGTCTTGACATCCTTT

GACCACCTAAGAGATTAGGTTTTCC

CTTCGGGGACAAAGAGACAGGTGGTGCATGGCTGTCGTCAGCTCG

TGTCGTGAGATGTTGGGTTAAGTCC

CGCAACGAGCGCAACCCTTGTTAATAGTTGCCAGCATTAAGTTGG

GCACTCTATTGAGACTGCCGGTGAC

AAACCGGAGGAAGGTGGGGATGACGTCAAGTCATCATGCCCCTTA

TGACCTGGGCTACACACGTGCTACA

ATGGGCAGTACAACGAGAAGCGAACCTGTGAAGGCAAGCGGATCT

CTTAAAGCTGTTCTCAGTTCGGACT

GTAGGCTGCAACTCGCCTACACGAAGCTGGAATCGCTAGTAATCG

CGGATCAGCACGCCGCGGTGAATAC

GTTCCCGGGCCTTGTACACACCGCCCGTCACACCATGAGAGTTTG

TAACACCCAAAGTCGGTGAGGTAAC

CTTTGGAGCCAGCCGCCTAAGGTGGGACAGATGATTAGGGTGAAG

-continued

TCGTAACAAGGTAGCCGTAGGAGAA

CCTGCGGCTGGATCACCTCCTTT

At step 208 of the method 200, the quantitative abundance is collated at the abundance determining module 112. The quantitative abundance of (i) each of the plurality of predetermined microbes associated with the saliva sample and (ii) each of the plurality of predetermined microbes associated with the stool sample, is collated to obtain a hybrid abundance matrix. Collation refers to concatenating (or appending) the data corresponding to the abundances of quantitative abundance of each of the plurality of predetermined microbes associated with the saliva sample to the data corresponding to the abundances of each of the plurality of predetermined microbes associated with the stool sample to obtain a hybrid abundance matrix suitable for input to downstream analysis steps.

In an embodiment, the data corresponding to the abundances of quantitative abundance of each of the plurality of predetermined microbes associated with the saliva sample and the data corresponding to the abundances of each of the plurality of predetermined microbes associated with the stool sample are provided as individual (independent) inputs to subsequent downstream analysis steps.

In an example scenario, the abundances of each of the plurality of predetermined microbes associated with the saliva sample and with the stool sample are collated to form a hybrid abundance table.

At step 210 of the method 200, a model score is determined in the ML module 114. The model score is determined based on the hybrid abundance matrix, using a pre-determined machine learning (ML) model.

The pre-determined machine learning (ML) model is an ensemble ML model that is built using a microbial abundance data corresponding to a plurality of training saliva samples and a plurality of training stool samples.

The plurality of predetermined microbes associated with the saliva sample and the plurality of predetermined microbes associated with the stool sample are features of the pre-determined machine learning (ML) model.

The quantitative abundance is determined individually, from respective extracted DNA sequences, using a first set of probes and a second set of probes specific to each of the plurality of predetermined microbes associated with the saliva sample and the stool sample respectively. The first set of probes includes a plurality of probes where each probe is utilized for each of the plurality of predetermined microbes (one probe for one predetermined microbe) associated with the saliva sample. Similarly, the second set of probes includes the plurality of probes where each probe is utilized for each of the plurality of predetermined microbes (one probe for one predetermined microbe) associated with the stool sample.

In an embodiment, a multiplex quantitative Polymerase Chain Reaction (qPCR) technique is employed for determining the quantitative abundance. More specifically, the multiplex quantitative Polymerase Chain Reaction (qPCR) technique define a design of the plurality of probes that are of the first set of probes for detecting and determining the quantitative abundance for each of the plurality of predetermined microbes associated with the saliva sample. Similarly, the multiplex quantitative Polymerase Chain Reaction (qPCR) technique define a design of the plurality of probes that are of the second set of probes in the form of sequential runs for detecting and determining the quantitative abundance for each of the plurality of predetermined microbes associated with the stool sample.

More specifically, the first set of probes specific to each of the plurality of predetermined microbes associated with the saliva sample are utilized in two sequential multiplex qPCR runs (defined by the multiplex quantitative Polymerase Chain Reaction (qPCR) technique), to determine the quantitative abundance of each of the plurality of predetermined microbes associated with the saliva sample. Further, the second set of probes specific to each of the plurality of predetermined microbes associated with the stool sample are utilized in three sequential multiplex qPCR runs (defined by the multiplex quantitative Polymerase Chain Reaction (qPCR) technique), to determine the quantitative abundance of each of the plurality of predetermined microbes associated with the stool sample.

In an embodiment, the plurality of predetermined microbes associated with the saliva sample and the plurality of predetermined microbes associated with the stool sample are captured from features of the respective pre-determined machine learning (ML) model. In an embodiment, the pre-determined machine learning (ML) model associated to the saliva and stool sample is an ensemble machine learning (ML) model that is built using a microbial abundance data corresponding to a plurality of training saliva and stool samples and the plurality of training saliva and stool samples are the saliva and stool samples used for training a machine learning model to obtain the corresponding pre-determined machine learning (ML) model for both saliva and stool samples. In an embodiment, the microbial abundance data corresponding to the plurality of training saliva and stool samples is the quantitative abundance of all the microbes present in each of the plurality of training saliva and stool samples.

The ensemble ML model is built using the plurality of training saliva samples and the plurality of training stool samples, individually, to obtain the corresponding pre-determined machine learning model. FIGS. 4A, 4B and 4C are flowcharts illustrating steps involved in building a pre-determined machine learning model according to some embodiments of the present disclosure. The technique for building the ensemble ML model accepts data in form of a feature table for multiple observations (the plurality of training samples) wherein each observation/sample is defined by 'N' features (F) which are continuous or/and variables and (N>=1). In case of training data (TR), each of the samples/observations further have a preassigned class/category which is binary in nature, i.e., the healthy class (A) and the diseased class (B). In case of test data (TS) or data received during actual deployment of the method, the model(s) built based on training data predicts the class/category of the samples/observations. During training process, the following steps are followed:

Initially at step 402, a healthy class tag or a diseased class tag is assigned to each of the samples in the collected plurality of training biological samples (either saliva samples and/or stool samples). The healthy class tag indicates absence of PCOS disease, and the diseased class tag indicates presence of PCOS disease.

At step 404, the training data comprises of a plurality of microbial abundance profiles corresponding to each of the collected plurality of training biological samples, wherein each microbial abundance profile corresponding to a training biological sample comprises of one or a plurality of feature (s) and respective abundance value (s) of the feature (s), wherein each feature in the microbial abundance profile corresponds to one of a plurality of microbial taxonomic groups present in the plurality of training biological samples.

In the next step 406, the training data (TR) is randomly partitioned into two sets—namely, an internal-train (ITR) and an internal-test (ITS), based on a parameter 'L1', wherein L1% samples from the total training data constitute the ITR set and (100-L1) % of the samples constitute the ITS set. Furthermore, the random partitioning into ITR and ITS sets is performed using a stratified sampling approach with the intent of preserving the relative proportion of samples belonging to the healthy class (A) or the diseased class (B) in the total training data in these newly drawn subsets.

In the next step 408, a predefined number of subsets are randomly selected out of the internal training set based on a second parameter (L2). Each of the subset comprises a randomly selected plurality of microbial abundance profiles corresponding to the plurality of training biological samples in the randomly selected subset, and wherein each of the subset comprises a proportionate part of samples belonging to the healthy class (A) and the remaining samples belonging to the diseased class (B). Thus, from ITR, 'M' randomly drawn subsets $ITRS_i$ (e.g., $ITRS_1$, $ITRS_2$, $ITRS_3$ ... $ITRS_M$), each containing S samples are further generated, wherein S=L2% of the samples present in ITR. In the current implementation, the values L2=80% and M=100 is used. Other values are within the scope of this invention.

In the next step 410, for each selected subset, a distribution of the abundance values of each of the features across the plurality of samples in the selected subset, and the distribution of the abundance values of each of the features across the samples belonging to the healthy class (A) in the selected subset and the samples belonging to the diseased class (B) in the selected subset are noted. Thus, from each subset $ITRS_i$ (where i=1, 2, 3, . . . , M), wherein there are total S samples, each of which are described by N features $(F_j)$ (where j=1, 2, 3, . . . , N), the distributions of each of the features $(ITRS_iDF_j)$ across S samples are noted. Similarly, from each subset $ITRS_i$ wherein there are $S_A$ samples belonging to the healthy class (A) and $S_B$ samples belonging to the diseased class (B), each of the samples being described by N features $(F_j, =, j=1, 2, 3, . . . , N)$, the distributions of each of the features $(ITRS_iD_AF_j)$ across $S_A$ samples, and the distributions of each of the features $(ITRS_iD_BF_j)$ across $S_B$ samples are noted.

In the next step 412, from the noted distributions of each selected subset, a first quartile value (Q1) and a third quartile value (Q3) of the distribution of each of the features is calculated across each of the plurality of samples in the selected subset. In an example, the respective first quartile value (Q1) and the third quartile value (Q3) of $ITRS_iDF_j$ may also be referred as $Q_1ITRS_iDF_j$ and $Q_3ITRS_iDF_j$.

Furthermore, in the next step 414, for each selected subset, a second quartile value of the distribution of each of the features across the samples belonging to the healthy class ($Q2_1$) in the selected subset and the samples belonging to the diseased class ($Q2_2$) in the selected subset is calculated. Thus, in an example, the median value (in other words, the second quartile value) of $(ITRS_iD_AF_j)$ is referred as $Q_2ITRS_iD_AF_j$, and the median value of $(ITRS_iD_BF_j)$ is referred as $Q_2ITRS_iD_BF_j$.

In the next step 416, for the M subsets of $ITRS_j$, a total of M values for each of $Q_2ITRS_iDF_j$, $Q_3ITRS_iDF_j$, $Q_2ITRS_iD_AF_j$, and $Q_2ITRS_iD_BF_j$, are calculated. Further at step 418, median value ( $\widetilde{Q1}_j$ ) is calculated for all calculated Q1, median value ($Q3_j$) is calculated for all calculated Q3, median value ($Q2_j$) is calculated for all calculated $Q2_1$ and median value ($Q4_j$) is calculated for all calculated $Q2_2$. Thus, $$\widetilde{Q1}_j = \text{median of } \{Q_1ITRS_1DF_j, \quad Q_1ITRS_2DF_j, \quad Q_1ITRS_3DF_j, \dots Q_1ITRS_MDF_j\}$$

$$\widetilde{Q3}_j, = \text{median of } \{Q_3ITRS_1DF_j, \quad Q_3ITRS_2DF_j, \quad Q_3ITRS_3DJF, \dots Q_3ITRS_MDF_j\}$$

$$\widetilde{Q2_A}_j = \text{median } \{Q_2ITRS_1D_AF_j, \quad Q_2ITRS_2D_AF_j, \quad Q_2ITRS_3D_AF_j, \dots Q_2ITRS_MD_AF_j\}$$

$$\widetilde{Q2_B}_j \text{ median } \{Q_1ITRS_1D_BF_j, \quad Q_1ITRS_2D_BF_j, \quad Q_1ITRS_3D_BF_j, \dots, Q_1ITRS_MD_BF_j\}$$

(where i=1, 2, 3, . . . , M; and j=1, 2, 3, . . . , N)

In the next step 420, a Mann-Whitney test is performed to test if a value of the feature $(F_j)$ is significantly (p<0.1) different between the samples belonging to the healthy class $(S_A)$ and the samples belonging to the diseased class $(S_B)$ in each of the M randomly drawn subsets $ITRS_j$. Other statistical tests based on the nature of distribution (e.g. t-test for normal distribution), nature of sampling (e.g. Wilcoxon signed rank test for paired case and control samples) or other methods of statistical comparison relevant for microbiome datasets (e.g. ALDEx2) can also be adopted.

In the next step 422, the features are shortlisted based on a first predefined criteria utilizing calculated median values and the Mann-Whitney test. The first predefined criteria comprises if a feature $F_j$ is observed to have significantly (p<0.1) different values in $S_A$ compared to $S_B$ in more than 70% of M subsets, and if $\widetilde{Q2_A}_j >= Q2_{min}$ OR $\widetilde{Q2_A}_j >= Q2$ min (a feature 'abundance' $\widetilde{Q2_A}_j$ threshold; $Q2_{min}=0$ in current implementation). $F_j$ is added to a set of shortlisted features (SF).

In the next step 424, a set of features is generated using the shortlisted features (SF) using a second predefined criteria, wherein the set of features are less than or equal to 15. If the number of shortlisted features (SF) obtained in previous step satisfies the criteria 1<=SF<=15, then the training process proceeds to model building with all the features in SF. If no shortlisted features (SF) are obtained in previous (i.e., SF<1) then following step is performed with all the features $F_j$ for evaluating the ability of the features, when considered independently, to distinguish between samples belonging to the healthy class (A) and the diseased class (B). Similarly, if the number of shortlisted features (SF) obtained in previous step exceeds fifteen (SF>15) then following step is performed with all the shortlisted features (SF) for evaluating the ability of the features, when considered independently, to distinguish between samples belonging to the healthy class (A) and the diseased class (B).

Steps for shortlisting the features in case of SF<1 or SF>15: For each of the features (obtained previously) taken individually, different threshold values are used to classify the samples belonging to the set ITR, and the results are cumulated to construct a receiver operating characteristic curve (ROC curve) for each of the features. The area under the curve (AUC) of the ROC curve of any feature ($AUC^F$) is indicative of the utility of the feature to distinguish between samples belonging to the healthy class (A) and the diseased class (B), and the same is computed for every feature. The shortlisted features (SF) set is modified to include only the top fifteen features from a list of features arranged in a descending order of the $AUC^F$ values.

In the next step 426, a plurality of combinations of the features present in the set of features is created to generate corresponding plurality of candidate feature sets (CF), wherein the plurality of combinations of features comprises a minimum of one and a maximum of 15 features. By definition the maximum possible candidate feature sets that can be created in this process is $K=2^{15}-1=32767$ (i.e., maximum value of K=32767).

In the next step 428, a plurality of candidate models is built corresponding to each of the plurality of candidate feature sets. At step 430, a model evaluation score (MES) is calculated corresponding to each of the plurality of candidate models. For each candidate feature set $CF_K$, a corresponding candidate model $CM_K$ is built and evaluated as mentioned in the steps mentioned below.

Steps for evaluating the candidate model:

Step 1: The values of the features $F_j$ constituting a candidate feature set defining the samples in ITR are transformed to $F_j'$ such that $\widetilde{Q1}_j$, $\widetilde{Q3}_j$, $\widetilde{Q2}_{Aj}$ and $\widetilde{Q2}_{Bj}$ $$F_j' = 0 \dots\dots\dots\dots \text{if } F_j < \tilde{Q}1_j$$

$$F_j' = 1 \dots\dots\dots\dots \text{if } F_j > \tilde{Q}3_j$$

$$F_j' = 0.5 \dots\dots\dots\dots \text{if } \tilde{Q}1_j = \tilde{Q}3_j$$

$$F_j' = \frac{F_j - \tilde{Q}1_j}{\tilde{Q}3_j - \tilde{Q}1_j} \dots\dots\dots\dots \text{if } \tilde{Q}1_j < F_j < \tilde{Q}3_j$$

Step 2: If for a feature $F_j$, it is observed that $\widetilde{Q2}_{Bj} > \widetilde{Q2}_{Aj}$ then the feature $F_j$ is tagged as a 'numerator' feature and added to a set of numerator features $F_{numerator}$. Else, feature $F_j$ is tagged as a 'denominator' feature and added to a set of denominator features $F_{denominator}$.

Step 3: Each candidate model ($CM_K$) is constituted as a simple ratio function given below—

$$CM_K = \frac{\sum F_{numerator}}{\sum F_{denominator}} \dots \text{when } F_{numerator} > 0$$

and $$F_{denominator} > 0 \text{ or,}$$

$$CM_K = \frac{\sum F_{numerator} + 1}{\sum F_{denominator} + 1} \dots \text{when either}$$

$$F_{numerator} \text{ or } F_{denominator} = 0$$

wherein, $\Sigma F_{numerator}$ represents the sum of values of all numerator features for a particular sample, and, wherein, $\Sigma F_{denominator}$ represents the sum of values of all denominator features for a particular sample.

For each of the features, a transformed value F' as obtained above is used in the candidate model equation.

Step 4: A candidate model $CM_K$ is used to generate candidate model scores ($CMS_K$) for each of the samples in the set ITR. From the set of scores $CMS_K$, the top 10 percentile and bottom 10 percentile scores are removed as outliers and thereafter the maximum and minimum scores from the set $CMS_K$ are noted as $CMS_{Kmax}$ and $CMS_{Kmin}$ respectively.

Step 5: Considering each of the scores in the set $CMS_K$ as a threshold (T), the model $CM_K$ is used to (re)classify the samples in the training set (ITR) such that— a sample is classified into the first-class if CMS>=T or a sample is classified into the second-class if CMS<T and based on a comparison of these classifications and the true/original classes of the samples, Matthew's correlation coefficients (MCC) for each of the thresholds are calculated, to evaluate how well each of the thresholds are able to distinguish between samples between the healthy class (A) and the diseased class (B).

Step 6: The threshold ($T_{max}$) which provides the maximum absolute MCC value ($|MCC_{max}|$) is noted. If $|MCC_{max}|<0.4$ for a candidate model $CM_K$, then the candidate model is discarded from further evaluation. Else, the $|MCC_{max}|$ value is considered as the 'train-MCC' value ($MCC_{train}$) for the model $CM_K$ and the model and its corresponding $T_{max}$ threshold is used to classify the samples in the internal-test set (ITS). In another implementation of the process, the $MCC_{max}$ threshold may not be applied for retaining the candidate model for subsequent evaluation. Before classifying the samples in the ITS set, the values of features characterizing the samples of the ITS set are transformed using the method mentioned in step 17 while using the earlier obtained values of $\widetilde{Q1}_j$, $\widetilde{Q3}_j$, $\widetilde{Q2}_{Aj}$, and $\widetilde{Q2}_{Bj}$ from the ITR set.

Step 7: The classification results on the samples from the ITS set are compared against the true/original classes of the samples (with pre-assigned labels), and the MCC for the model $CM_K$ and its corresponding $T_{max}$ threshold on the ITS samples is calculated ($MCC_{test}$).

Step 8: A model evaluation score (MES) for candidate model $CM_K$ is calculated as $MES=|(MCC_{train}+MCC_{test})|-|(MCC_{train}-MCC_{test})|$ In the next step 432, a model is selected out of the plurality of candidate models as the best model using the highest model evaluation score wherein the selected model is tagged as a forward model The model $CM_K$ is tagged as a "strong model" if all the features in the corresponding candidate feature set satisfies the Mann-Whitney test based shortlisting criteria described above. Otherwise, if any of the features in the corresponding feature set fails to satisfy the Mann-Whitney test, the model $CM_K$ is tagged as a "weak model".

In the next step, the above process is repeated for candidate models and respective MES scores are used to rank all the models. The best model is subsequently chosen based on the MES score. In case there are more than one model with the best MES score, the best model is chosen based on the following criteria (in order of preference):

(a) the model with fewer number of features (i.e., based on a smaller candidate feature set) is chosen.

(b) the model with lower $T_{max}$ (threshold value) is chosen.

In the next step, the best model obtained through above steps is tagged as a forward model ($MD_{fwd}$). The model $MD_{fwd}$ additionally constitutes its corresponding $T_{max}$ threshold, the $CMS_{Kmax}$ and $CMS_{Kmin}$ values, and the $\widetilde{Q1}_j$, $\widetilde{Q3}_j$, $\widetilde{Q2}_{Aj}$ and $\widetilde{Q2}_{Bj}$ values corresponding to the ITR set.

In the next step 434, the tags assigned to the healthy class (A) and the diseased class (B) of the plurality of samples present in the training data are swapped. At step 436, all of the above steps 404 to 432 to determine the best model are repeated after swapping the class labels (A<->B) for the entire training set (TR) to obtain a best model tagged as the reverse model ($MD_{rev}$). The model $MD_{rev}$ additionally constitutes its corresponding $T_{max}$ threshold, the $CMS_{Kmax}$ and $CMS_{Kmin}$ values, and the $\widetilde{Q1}_J$, $\widetilde{Q3}_J$, $\widetilde{Q2_{AJ}}$, and $\widetilde{Q2_{BJ}}$ values corresponding to the ITR set.

Further above steps are iterated 'R' times using multiple randomly partitioned ITR and ITS sets generated initially. After each iteration, the features constituting the models $MD_{fwd}$ obtained in the current iteration (r) are compared against, and if necessary, appended to, a set of unique features $F_{unq}a$ that consists of features constituting the $MD_{fwd}$ obtained in earlier iterations (i.e., up to iteration r−1). Similar procedure is also adopted for $MD_{rev}$ too. The iterations proceed while the value of R satisfies the following criteria—

$$R <= R_{max} \tag{i}$$

$$(|F_{unq}| \text{ after iteration } R) > (|F_{unq}| \text{ after iteration } R - R_{unq}) \tag{ii}$$

$$|F_{unq}| \text{ after iteration } no. \ R <= Fet_{max} \tag{iii}$$

Wherein, $R_{max}$ is a parameter indicating the maximum number of iterations allowed;

$R_{unq}$ is a parameter indicating the maximum number of iterations allowed without any cumulative increase in the number of unique features $|F_{unq}|$ in the models being generated in consecutive iterations; and $Fet_{max}$ is a parameter indicating the maximum allowed value of $|F_{unq}|$ (i.e., the no. of unique features cumulated through the iterative process).

In the current implementation, the values $R_{max}$=100 and $R_{unq}$=10 and $Fet_{max}$=100 are used. Other values of these and other parameters disclosed here, for fine tuning and suitability for other datasets are, within the scope of this invention In the next step 438, a plurality of forward models and a plurality of reverse models are generated for a predefined number of times using randomly partitioned internal training set and the internal test set. In the next step 440, an ensemble of forward models is generated using the plurality of forward models and an ensemble of reverse models is generated using the plurality of reverse models. This is referred as an ensemble of forward models (ENS-MD_{fwd}) and an ensemble of reverse models (ENS-MD_{rev}).

At step 442, the best models from each of these ensembles, i.e. the best of the forward models (BMD_{fwd}) and the best of the reverse models (BMD_{rev}) respectively, are identified.

If all models in an ensemble are "weak models", the best model from the ensemble (BMD) is chosen by ranking the models based on their model evaluation scores and associated criteria. Also, if an ensemble contains more than one "strong models", then only those strong models are considered for ranking based on their model evaluation scores and associated criteria as mentioned above, and the best model from the ensemble (BMD) is thereby chosen.

In the next step 444, a final single model (FMs) is chosen as the ensemble classification model from amongst the best forward model and the best reverse model based on how they classify the individual samples from the training data. Once the best models from each of the ensemble of forward models and the ensemble of reverse models, i.e., the best of the forward models (BMD_{fwd}) and the best of the reverse models (BMD_{rev}) are identified, the final single model (FM_{single}) is chosen from amongst BMD_{fwd} and BMD_{rev} based on how well they can classify the individual samples from the entire training set (TR). The AUC value for ROC curves for each of these two models are computed based on the predicted model scores for the training set (TR) samples and their pre-assigned classes. The model having the best AUC for ROC value is selected as the final single model (FM_{single}). If both BMD_{fwd} and BMD_{rev} have the same AUC value, BMD_{fwd} is chosen as FM_{single}.

In an alternate implementation FM_{single} can be chosen based whether BMD_{fwd} or BMD_{rev} obtains a higher MCC value while classifying the TR samples. Once the FM_{single} model has been chosen, for classification of any samples from a test set (TS) or any sample data received during actual deployment of the method, the FM_{single} model is used after:

(a) appropriately transforming the features corresponding to the sample being classified using the $\widetilde{Q1}_J$, $\widetilde{Q3}_J$, $\widetilde{Q2_{AJ}}$ and $\widetilde{Q2_{BJ}}$ values corresponding to the FM_{single} model, $\widetilde{Q1}_J$, $\widetilde{Q3}_J$, $\widetilde{Q2_{AJ}}$ (b) limiting the model score between a maximum of $CMS_{Kmax}$ and a minimum of $CMS_{Kmin}$ values corresponding to the FM_{single} model, and (c) classification based on the model score using its corresponding threshold $T_{max}$.

According to an embodiment of the disclosure, the ensemble of forward models (ENS-MD_{fwd}) and the ensemble of reverse models (ENS-MD_{rev}) are also evaluated for their collective classification efficiencies using an ensemble model scoring. In the ensemble scoring method, each of the models (MD) constituting an ensemble (ENS) are used to generate a model score (MS) for each of the samples from the entire TR set. For any specific sample the values of the features corresponding to the sample are appropriately $\widetilde{Q1}_J$, $\widetilde{Q3}_J$, $\widetilde{Q2_{AJ}}$ transformed using the $\widetilde{Q1}_J$, $\widetilde{Q3}_J$, $\widetilde{Q2_{AJ}}$ and $\widetilde{Q2_{BJ}}$ values corresponding to the model MD. The model scores (MS) are then transformed into scaled model scores (SMS) having values between −1 and +1, using the following procedure:

$$SMS = (MS - T_{max}) / (CMS_{Kmax} - T_{max}), \ldots\ldots \text{when } MS \geq T_{max},$$

and $$SMS = (MS - T_{max}) / (T_{max} - CMS_{Kmin}), \ldots\ldots \text{when } MS < T_{max},$$

Wherein, $T_{max}$, $CMS_{Kmax}$, and $CMS_{Kmin}$ values corresponding to the respective model is used.

Let $SMS_{avg}$ be the average of all SMS obtained using all models in ENS for a particular sample.

When using Forward model [ENS–MD_{fwd}], $$SMS_{avg} = SMS_{avg} * (+1)$$

If $SMS_{avg}$>=0, sample is classified as 'B'
If $SMS_{avg}$<0, sample is classified as 'A'
When using Reverse model [ENS–MD_{rev}]:

$$SMS_{avg} = SMS_{avg} * (-1)$$

If $SMS_{avg}>0$, sample is classified as 'B'

If $SMS_{avg}<=0$, sample is classified as 'A'

If all models in one of the ensembles are weak models, then the other one having (one or more) strong models is selected as a final ensemble model ($FM_{ens}$), and subsequently used for classification of any samples from a test set (TS) or any sample data received during actual deployment of the method, using the scoring and classification process mentioned in above paragraph. If both ensembles have constituent strong models, then both the ensembles are evaluated for their efficiency by scoring them on all individual samples in TR. The AUC value for ROC curves for each of these two ensembles are computed based on the predicted $SMS_{avg}$ for all the training set (TR) samples and their pre-assigned classes. The ensemble of models having the best AUC for ROC value is selected as the final ensemble model ($FM_{ens}$). In case both ENS-MD$_{fwd}$ and ENS-MD$_{rev}$ exhibit equal AUC values then ENS-MD$_{fwd}$ is chosen as the final ensemble model ($FM_{ens}$). In an alternate implementation, $FM_{ens}$ can be chosen based whether ENS-MD$_{fwd}$ and ENS-MD$_{rev}$ obtains a higher average MCC value for their respective constituent models while classifying the TR samples.

Thus, either the $FM_{single}$ model or $FM_{ens}$ ensemble of models can be used for classification of any samples from a test set (TS) or any sample data received during actual deployment of the method.

In an embodiment, the one or more predetermined microbes out of the plurality of predetermined microbes associated with the saliva sample, are common to the first multiplex qPCR run (Run 1), the second multiplex qPCR run (Run 2) for determining the associated quantitative abundance. In an embodiment, the one or more predetermined microbes that are common to the first multiplex qPCR run (Run 1) and the second multiplex qPCR run (Run 2) are determined based on (i) the median abundance (obtained from microbial abundance data) of each of the plurality of predetermined microbes obtained from the plurality of training saliva samples, (ii) the frequency of occurrence of each of the plurality of predetermined microbes constituting the ensemble ML model associated with the saliva sample. More specifically, the one or more predetermined microbes (from amongst the set of predetermined microbes) has/have the highest (or relatively higher) median abundance or frequency of occurrence (as compared to the median abundance(s) or the frequency of occurrence of each microbe in the remaining set of predetermined microbes) across the plurality of training saliva samples is/are common to the first multiplex qPCR run (Run 1) and the second multiplex qPCR run (Run 2).

For example, a predetermined microbe having a high median abundance or a high frequency of occurrence from the microbial abundance data is determined and utilized in more than one Run. As shown in FIG. 3A the plurality of predetermined microbes, the quantitative abundance of which are being determined through the first multiplex qPCR run are: *Phocaeicola, Simonsiella, Massiliprevotella* and *Streptobacillus*; and the plurality of predetermined microbes, the quantitative abundance of which are being determined through the second multiplex qPCR run are: *Phocaeicola, Simonsiella, Rothia*, and *Slackia*.

In an embodiment, the one or more predetermined microbes out of the plurality of predetermined microbes associated with the stool sample, are common to the third multiplex qPCR run (Run 3), the fourth multiplex qPCR run (Run 4) and the fifth multiplex qPCR run (Run 5) are determined based on (i) the median abundance (obtained from microbial abundance data) of each of the plurality of predetermined microbes obtained from the plurality of training stool samples, (ii) the frequency of occurrence of each of the plurality of predetermined microbes constituting the ensemble ML model associated with the stool sample. More specifically, the one or more predetermined microbes (from amongst the set of predetermined microbes) has/have the highest (or relatively higher) median abundance or frequency of occurrence (as compared to the median abundance(s) or the frequency of occurrence of each microbe in the remaining set of predetermined microbes) across the plurality of training stool samples is/are common to the third multiplex qPCR run (Run 3), the fourth multiplex qPCR run (Run 4) and the fifth multiplex qPCR run (Run 5)

For example, a predetermined microbe having a high median abundance or a high frequency of occurrence from the microbial abundance data is determined and utilized in more than one Run. As shown in FIG. 3B the plurality of predetermined microbes, the quantitative abundance of which are being determined through the plurality of predetermined microbes, the quantitative abundance of which are being determined through the third multiplex qPCR run are: *Oscillibacter, Cuneatibacter, Pseudoflavonifractor*, and *Gordonibacter*; the plurality of predetermined microbes, the quantitative abundance of which are being determined through the fourth multiplex qPCR run are: *Oscillibacter, Cuneatibacter, Faecalibacterium* and *Neisseria*; and the plurality of predetermined microbes, the quantitative abundance of which are being determined through the fifth multiplex qPCR run are: *Fusobacterium, Lactococcus, Faecalibacterium*, and *Lactobacilus*

For example, a predetermined microbe having a high median abundance or a high frequency of occurrence from the microbial abundance data is determined and utilized in more than one Run. As shown in FIG. 3A, the predetermined microbe *Simonsiella* and *Phocaeicola* is common for both the first multiplex qPCR run (Run 1) and the second multiplex qPCR run (Run 2). Similarly, as shown in FIG. 3B the predetermined microbe *Oscillibacter, Cuneatibacteris* common for both the third multiplex qPCR run (Run 3) and the fourth multiplex qPCR run (Run 4) and the predetermined microbe *Faecalibacterium* is common for both the fourth multiplex qPCR run (Run 4) and the fifth multiplex qPCR run (Run 5)

In an embodiment, the quantitative abundance determination involves creating abundance or feature table and generation of the percent normalized abundance or feature table having percent normalized abundance values of the predetermined microbes or OTUs or taxa in each sample. In another embodiment, Multicolour Combinatorial Probe Coding (MCPC) qPCR or real-time PCR based measurement of abundance of the microbial OTUs or taxa can also be considered for quantification of a predefined set of taxa. Alternatively, any other pre-processing techniques or data normalization techniques known in the state of art can be used for normalization and feature selection from the main feature table.

Design configuration & number of qPCR runs required for quantifying the abundance of target microbial taxa/features: Let us assume that a maximum of five unique DNA fragments, each representing a microbial taxa or spike DNA, can be quantified in a one multiplexed qPCR run. Therefore, to analyze a disease signature (captured in an ML model) comprising of 'n' microbial taxa/features, a minimum of $(1+[(n-4)/4])$ multiplexed qPCR runs would be required wherein 'n' is the unique number of microbial taxonomic groups constituting the frugal set of markers, and wherein each multiplexed qPCR run is configured to determine, in the test biological sample, the relative abundance of a predetermined subset of the microbial taxonomic groups constituting the disease signature. This minimum number is based on assumptions that:

(a) the spike DNA should be analyzed at least once in one of the '(1+[(n−4)/4])' multiplexed qPCR runs; and (b) an overlap of at least one microbial taxa/features was done between two corresponding runs.

For example, if a disease signature comprises of 8 microbial taxa (A, B, C, D, E, F, G, and H), then at least TWO multiplexed qPCR runs would be required, where Z is the spike DNA of known concentration and taxa 'D' is analyzed in both multiplexed qPCR runs. Here, [(n−4)/4] indicates a ceiling value of the expression. Thus, the minimum no. of required qPCR runs would be:

for 1-4 signatures/features for 5-8 signatures/features for 9-12 signatures/features for 13-16 signatures/features, and so on . . . .

Example A: Run 1: Z A B C $\underline{D}$; Run2: $\underline{D}$ E F G H

Similarly, for a feature size of 12 (A, B, C, D, E, F, G, H, I, J, K, and L), at least THREE multiplexed qPCR runs would be required, where Z is the spike DNA of known concentration and taxa 'D' and 'H' are analyzed in twice.

Example B: Run1: Z A B C $\underline{D}$; Run2: $\underline{D}$ E F G $\underline{H}$; Run3: $\underline{H}$ I J K L If the number of features constituting the signature is not optimal for the above condition, i.e., for e.g., the number of features is 10, then more than one microbial taxon can be analyzed twice. The same is exemplified below, wherein taxa C and D are analyzed twice (in Runs 1 and 2). Similarly, taxa F and G are also analyzed twice (in Runs 2 and 3)

Example C: Run1: Z A B $\underline{C}$ $\underline{D}$; Run2: $\underline{C}$ $\underline{D}$ E $\underline{F}$ $\underline{G}$; Run3: $\underline{F}$ $\underline{G}$ H I J In alternate implementations, the spike DNA (Z) can be analyzed in each of the runs. In that scenario, the first multiplexed qPCR will be able to accommodate up to FOUR features. Each additional multiplexed qPCR run will accommodate up to THREE new/additional features as shown by underlining in the example below. Thus, two multiplexed qPCR runs would be required for a feature set of up to seven; three qPCR runs for a feature set of up to ten and so on. Run1: Z A B C $\underline{D}$; Run2: Z D $\underline{E}$ $\underline{F}$ $\underline{G}$; Run3: Z G $\underline{H}$ $\underline{I}$ $\underline{J}$ Furthermore, if the number of features is not optimal for the above condition, then two or more taxa/features can be analyzed multiple times as shown in example C.

Methodology to interpret/quantify the abundance of a microbial taxon from data obtained from above qPCR configurations: Given that the concentration of the spike DNA (Z) is previously known—say $x_1$. If the measured concentration of Z in the multiplexed qPCR is $x_2$, then all the measured concentration in a single multiplexed qPCR run can be normalized multiplying by a normalizing factor $(NF_{run})$ of $x_1/x_2$.

In cases where the spike DNA is only analyzed in only one of the multiplexed qPCR runs (as shown in examples A, B and C), then the normalized values of the taxa/feature in the first run which is/are re-analyzed in the Run 2, can be used for adjusting the concentrations inferred from the Run 2 of the multiplexed qPCR. Following Example—A (described previously), Actual conc of Z: $x_1$ Measured conc of Z: $x_2$ Normalizing factor $NF_{run1}$: $x_1/x_2$ Inferred conc. of A (from Run 1): $A'_{run1}*NF_{run1}$ Inferred conc. of B (from Run 1): $B'_{run1}*NF_{run1}$ Inferred conc. of C (from Run 1): $C'_{run1}*NF_{run1}$ Inferred conc. of D (from Run 1): $D'_{run1}*NF_{run1}$ Where $A'_{run1}$, $B'_{run1}$, $C'_{run1}$, and $D'_{run1}$ are the measured/analyzed concentrations of taxa/feature A, B, C and D respectively.

Normalizing factor $NF_{run2}$: Inferred conc. of D from Run 1/Measured concentrations of feature D in Run 2

Inferred conc. of E: $E'_{run2}*NF_{run2}$

Inferred conc. of F: $F'_{run2}*NF_{run2}$

Inferred conc. of G: $G'_{run2}*NF_{run2}$

Inferred conc. of H: $H'_{run2}*NF_{run2}$

The same protocol may be repeated for normalizing/adjusting the concentrations measured from all subsequent runs (as in example B). In case wherein more than once feature is analyzed in subsequent runs (as in example C), a median Normalizing factor (NF)—derived from the NFs for each of the replication features may be used for computing the inferred concentrations from that run.

In alternate implementations, wherein the spike DNA (Z) is analyzed in each of the runs (as in example D), Normalizing factor (NF) corresponding to each of the runs may be computed and used for inferring the concentrations of the constituent features. In cases, where the measured spike DNA (Z) concentration varies by more than 25% from the actual concentration, it is suggested that the observations from the said multiplexed qPCR run be discarded, and a fresh multiplexed qPCR run for the sub-set of features be performed.

At step 212 of the method 200, a risk assessment of the subject is performed at the assessment module 116. The risk assessment is performed based on the model score and a predefined threshold value.

At step 214 of the method 200, a personalized recommendation is provided, via the one or more hardware processors, wherein the personalized recommendation comprises a designed personalized microbial concoction to enable amelioration of PCOS based on risk assessment. The personalized recommendation for the subject assessed as having the risk of PCOS at step 212 of the method 200 is performed through the Personalized design and recommendation module 118. Wherein, the personalized recommendation includes mapping the model organisms contributing to generation of model score at step 210 to predefined sets of antibiotic and probiotic candidates (or antibiotic and probiotic candidates suitable in respect to the model organisms as known in scientific literature) as according to their comparatively higher abundances (normalized/raw/ratio etc.) in the diseased or healthy groups in the training model respectively, and suggesting appropriate personalized targets for application of compositions to ameliorate PCOS.

More specifically, one or a combination of probiotic and antibiotic (microbial) candidates or targets designed via or based on features (i.e., taxa or microbes) constituting the ML model. The designing of the one or the combination of probiotic and antibiotic candidates' targets may be performed by mapping the features (i.e., organisms/taxa/microbes) constituting the ML model to the complete set of microbes (or a pre-defined subset of the same) using the following steps The microbial markers constituting the ML model can be further used in designing (one or a combination of) antibiotic/probiotic (microbial) targets (or antibiotic and probiotic candidates suitable in respect to the model organisms as known in scientific literature) as according to their comparatively higher abundances (normalized/raw/ratio etc.) in the diseased or healthy groups in the training model respectively, and suggesting appropriate personalized targets for treatment and personalized recommendation. The designing of the one (or a combination of) antibiotic or probiotic candidates/targets may be performed by mapping the features (i.e., organisms/taxa/microbes) constituting the ML model to the complete set of microbes (or a pre-defined subset of the same) using the following steps.

At step 1, Compute pair-wise correlations (using the Pearson's and/or Spearman's correlation index) between abundances of features (i.e., organisms/taxa/microbes) constituting the ML model and the abundances corresponding to the complete set of microbial taxa (represented by microbial markers) computed individually from (a) the subset of biological samples corresponding to the healthy class (A) i.e. the class of samples that were taken from patients diagnosed to be free of PCOS, and (b) the diseased class i.e. the class of samples that were taken from PCOS affected subjects, wherein both the samples belonging to the healthy class (A) and diseased classes (B) were used as training data for generating the ML model.

At step 2-positive and negative interactions between features (i.e., organisms/taxa/microbes) constituting the ML model and all other taxa in the healthy and the diseased class of training samples (individually) are deduced using critical correlation (r) value as the cut-off (as taught in Batushansky et al., 2016), such that inter-taxa correlation index values greater than +r value are affiliated as 'positive interactions', while those less than −r value are affiliated as 'negative interactions'.

At step 3. Steps 1 and 2 are repeated 1000 times and only those interactions are considered relevant that appear in at least 70% of iterations with a Benjamini-Hochberg (BH) corrected p-value cut-off of 0.1 are retained (hereafter referred to as model taxa interactions corresponding to health and diseased class of samples).

At step 4, thereafter, following set of rules (indicated in Table 1 below) are used to arrive at the relevant candidate for recommendation using the retained model taxa interactions:

TABLE 1

| Probiotic Candidates | Antibiotic Candidates |
|---|---|
| $(M_H - C_T)_{HP}$ && $(M_H - C_T)_{DP}$ | $(M_H - C_A)_{HN}$ ‖ $(M_H - C_A)_{DN}$ |
| $(M_H - C_T)_{DP}$ | $(M_D - C_A)_{HP}$ ‖ $(M_D - C_A)_{DP}$ |
| $(M_D - C_T)_{HN}$ && $(M_D - C_T)_{DN}$ | |

From Table 1, $M_H$ represents a model taxon having significantly higher abundance in healthy class (A);

$M_D$ represents a model taxon having significantly higher abundance in PCOS (diseased (B)/unhealthy (A)) class;

$C_T$ represents a potential candidate for recommendation;

$C_A$ represents a potential antibiotic target candidate;

$M_H$-$C_T$ represents an interaction between a model taxon (abundant in healthy class (A)) with a potential candidate for recommendation;

$M_D$-$C_T$ represents an interaction between a model taxon (abundant in diseased class (A)) with a potential candidate for recommendation;

$M_D$-$C_A$ represents an interaction between a model taxon (abundant in diseased class) with a potential antibiotic target candidate;

$M_H$-$C_A$ represents an interaction between a model taxon (abundant in healthy class (A)) with a potential antibiotic target candidate;

HP represents a positive interaction in a healthy environment population;

HN represents a negative interaction in a healthy environment population;

DP represents a positive interaction in a diseased environment population; and

DN represents a negative interaction in a diseased environment population.

Markers in the model which are higher in diseased state are suitable antibiotic targets for which existing antibiotics can be known in the scientific literature or designed from the taxa which are having negative interactions with the target marker microbe. Similarly, probiotics can be targeted at the microbial markers found to be abundant in case of healthy, subjects in training model, where known existing probiotics can be present in scientific literature or can be designed from the microbes that are positively interacting with the target marker microbe. One or more of the set of microbes constituting the identified antibiotic target microbial taxa candidates may be targeted (individually or in combination) via antibiotics or any other treatment methodologies that can reduce the abundance of the identified antibiotic target microbial taxa and result in ameliorating the risk of PCOS. Furthermore, such antibiotic personalized recommendation (as detailed above) may also help in promoting development of a healthy microbiome, which (may) ameliorate the risk of PCOS. Additionally, one or more of the set of microbes constituting the identified probiotic target microbial taxa candidates may be targeted (individually or in combination) via probiotics or any other treatment methodologies that can increase the abundance of the identified probiotic target microbial taxa and result in ameliorating the risk of PCOS.

One or more of the set of microbes constituting the identified probiotic candidates for recommendation may be administered/used (individually or in combination) as probiotic formulations for treating (or ameliorating the symptoms of or the disease severity of) individuals identified as having PCOS. Furthermore, the mentioned probiotic formulations may help in promoting development of a healthy oral microbiome (in the individuals administered with the probiotic) which (may) ameliorate the symptoms of, or the disease severity of individuals identified as having PCOS.

Figure 5:
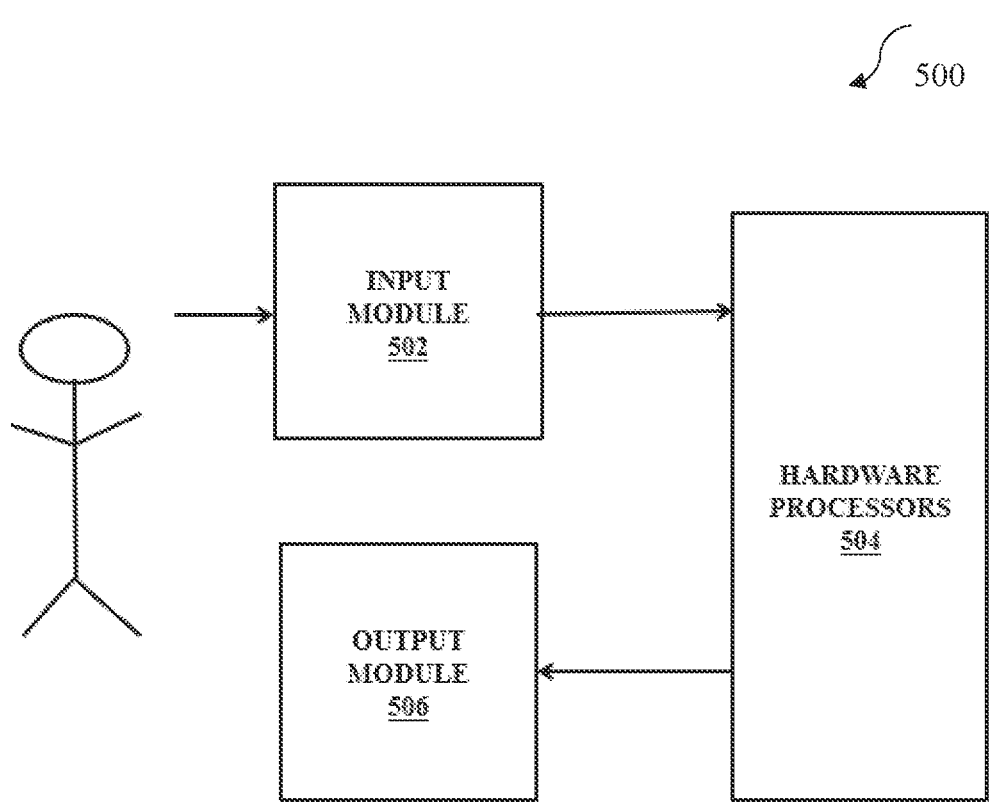
FIG. 5 illustrates an exemplary block diagram of a kit for risk assessment of PCOS present in the subject, according to some embodiments of the present disclosure.

A kit for risk assessment of PCOS disorder in the subject, is disclosed in FIG. 5, wherein the FIG. 5 illustrates an exemplary block diagram of a kit 500 for risk assessment of PCOS disorder present in the subject, according to some embodiments of the present disclosure.

As shown in FIG. 5, the kit 500 includes an input module 502, one or more hardware processors 504 and an output module 506.

The input module 502 is used for receiving the saliva sample and the stool sample of the subject whose risk of PCOS disorder is to be assessed.

In an embodiment, the input module 502 may be a medium, a carrier, a set of mediums, or a set of carries that can hold the saliva sample and the stool sample individually.

The one or more hardware processors 504 are configured to analyze the saliva sample and the stool sample present in the input module 502, using the one or more steps of the method 200.

The present disclosure determines minimum number of microbes, or OTUs or taxonomies for determining the microbial quantitative abundance using which the risk assessment of the subject for the PCOS is identified. More specifically, the plurality of predetermined microbes associated with the saliva sample are: *Phocaeicola, Simonsiella, Massiliprevotella, Streptobacillus, Rothia*, and *Slackia*; and the plurality of predetermined microbes associated with the stool sample are: *Oscillibacter, Cuneatibacter, Faecalibacterium, Pseudoflavonifractor, Gordonibacter, Neisseria, Fusobacterium, Lactococcus*, and *Lactobacillus*—taxonomies that are more influenced are identified for determining the microbial quantitative abundance. Hence, the present disclosure requires less resources, simple and yet effective.

The present disclosure is a systematically designed, exhaustively tested and repeatedly validated quantitative methodology for PCOS risk assessment and guided development of personalized recommendation for amelioration of PCOS.

In an embodiment, the one or more hardware processors 504 are equivalent or same that of the one or more hardware processors 106 of the system 100.

The output module 506 is used for displaying the risk assessment of PCOS disorder of the subject, based on the analysis of the one or more hardware processors 504. In other words, the output module 506 is used for indicating on the presence or non-presence of the PCOS of the subject.

In an embodiment, the output module 506 includes but are not limited to a display device, an indicator, a color indicator, or any other equipment that can show the result representation on the PCOS to the subject.

EXPERIMENTS

Experimented have been conducted to understand the performance of the disclosed technique.

The present disclosure focuses on stool/saliva microbiome of PCOS subjects, an avenue which is sparsely touched upon. Dependence on a large number of microbial features for developing the assessment procedure is neither easily translatable nor economical. Moreover, it is difficult to arrive at a relevant and relatable therapeutic solution based on such a large number of microbes in a diagnostic marker. The present disclosure relies on creation of co-related hybrid features (genera) for each subject through paired sampling. And the disclosed biomarker model is constituted by as less as 15 genera taken together from both the saliva sample (6 genera) and the stool sample (9 genera) microbiome samples with an average AUC of 0.79 with a standard deviation of 0.17, with the ensemble model giving a AUC as high as 0.93 for ensemble model developed using hybrid feature set. In hybrid feature based models, the genera/OTU/taxa are not independently considered (unlike the competitive literature) but combined together to create hybrid biomarkers constituted by site-specific microbes. Even site-specific biomarkers are consistently efficient as well as sparse/frugal through the present disclosure. The data splits employed are different which are expected to yield differences in performance, however the smaller number of features with good average cross validated performance is a clear differentiator.

By focusing on frugal combination of disease biomarkers, the present disclosure enables accurate and easy diagnosis of a disease. Importantly, selection of a small set of genera (total 15 genera taken together from both the saliva sample and the stool sites in a single hybrid ensemble model) as biomarker component. The present disclosure further enables an easy trace-back towards causality and guides in focused recommendation design to ameliorate the disease. A systematic diagnostic and recommendation design, with a small set of features, makes it convenient and economical to deploy for mass adoption.

The disclosure provides an exemplary workflow using the described methods in this disclosure applied on the public dataset provided in NCBI SRA database study ID SRP077213. The described methodology can be adopted for other datasets to arrive at additional region/age or other metadata specific models and recommendations.

Example Scenario

Model training: The ML model along with the set of ensemble models were obtained using the data associated with the respective samples. i.e., saliva samples, or stool samples, or both. The data associated with the respective samples is divided into training data and the test data. The present disclosure accepts data in form of a feature table for multiple observations (or samples) wherein each observation/sample is defined by 'N' features (F) which are continuous variables and (N>=1). In case of training data (TR), each of the samples/observations further have a preassigned class/category which is binary in nature (e.g., A or B). In case of test data (TS) or data received during actual deployment of the method, the model(s) built based on training data predicts the class/category of the samples/observations.

B. Model training results: The features (microbes) of the single best model and the ensemble model are analyzed and the features that are most frequently occurred are identified, which are then used as the plurality of predetermined microbes to determine the quantitative abundance in real test cases, as explained at step 206 of the method 200.

Table 2 shows the list of features (microbes) of the ensemble model for the hybrid samples (both saliva and stool samples) along with their occurrences. In table 2, SA indicates the microbe is associated saliva sample and ST indicate the microbe is associated with the stool sample.

TABLE 2

List of features (microbes) of the ensemble model for the hybrid samples (both saliva and stool samples)

| Unique Features in Ensemble Model | Occurrence |
|---|---|
| sa_Phocaeicola | 10 |
| sa_Simonsiella | 8 |
| st_Oscillibacter | 4 |
| sa_Massiliprevotella | 4 |
| st_Cuneatibacter | 2 |
| st_Faecalibacterium | 2 |
| st_Pseudoflavonifractor | 1 |
| sa_Rothia | 1 |
| sa_Streptobacillus | 1 |
| st_Gordonibacter | 1 |
| sa_Slackia | 1 |
| st_Neisseria | 1 |
| st_Fusobacterium | 1 |
| st_Lactococcus | 1 |
| st_Lactobacillus | 1 |

Table 3 shows an exemplary model metrics data of the single best ML model and the ensemble model that has performed the best for the hybrid saliva and stool sample along with their occurrences.

TABLE 3

| Model Metrics | Single | Ensemble |
|---|---|---|
| Exemplary model metrics data of the single best ML model and the ensemble model | | |
| CV (100 iterations) Mean AUC | 0.766667 | 0.79 |
| AUC Min-Max | 0.500000-1.000000 | 0.500000-1.000000 |
| AUC Std. Dev | 0.186527 | 0.168542 |
| CV (100 iterations) Mean MCC | 0.434966 | 0.495677 |
| MCC Min-Max | 0.000000-1.000000 | 0.000000-1.000000 |
| MCC Std. Dev | 0.300531 | 0.30011 |
| Training AUC | 0.916667 | 0.934211 |
| Training MCC | 0.637878 | 0.651235 |

Case Study: A case study is conducted on a subject for whom the risk of PCOS to be ascertained and the steps 1 to 8 are mentioned to explain the case study and the steps are in line with the steps of the method of the present disclosure.

At step 1, both the saliva sample and stool samples are collected at the same, as test samples from the subject for whom the risk of PCOS to be ascertained.

At step 2, the raw abundances of various microbial taxonomic groups or a subset corresponding to the set of predetermined microbes as in Table 2, present in the collected samples are quantified and a unified table is created. Methodology used in this step involves extraction of microbial DNA contents from the collected samples followed by amplification and sequencing of either full-length or specific variable regions of the bacterial 16S rRNA marker genes using the next-generation sequencing platform or by using the multiplexed qPCR-based quantification methodology. Table 4 shows the raw abundance of various microbial taxonomic groups present in the collected samples. In Table 4, SA indicates the microbe is associated with the saliva sample and ST indicates the microbe is associated with the stool sample.

TABLE 4

| Features | Raw Abundance |
|---|---|
| sa_Porphyromonas | 6044 |
| sa_Tannerella | 2 |
| sa_Parabacteroides | 1 |
| sa_Macellibacteroides | 0 |
| sa_Prevotella | 29070 |
| sa_Prevotellamassilia | 4424 |
| sa_Alloprevotella | 1051 |
| sa_Massiliprevotella | 3 |
| . . . | . . . |
| . . . | . . . |
| . . . | . . . |
| st_Fretibacterium | 0 |
| st_Deinococcus | 0 |

At step 3, the percent normalized abundances values of various microbial taxonomic groups are calculated individually for each of the saliva sample and the stool sample, using the corresponding raw abundances mentioned in Table 4. The Table 5 shows the percent normalized abundances values of various microbial taxonomic groups present in the collected samples.

TABLE 5

| Features | Normalized Abundance |
|---|---|
| sa_Porphyromonas | 5.3228 |
| sa_Tannerella | 0.0018 |
| sa_Parabacteroides | 0.0009 |
| sa_Macellibacteroides | 0.0000 |
| sa_Prevotella | 25.6011 |
| sa_Prevotellamassilia | 3.8961 |
| sa_Alloprevotella | 0.9256 |
| sa_Massiliprevotella | 0.0026 |
| . . . | . . . |
| . . . | . . . |
| . . . | . . . |
| st_Fretibacterium | 0 |
| st_Deinococcus | 0 |

At step 4, From the normalized abundance table, abundances of only the subset of microbial taxonomic groups which overlap with the list of microbial taxonomic groups that are provided against the models in the ensemble of models are retained. Table 6 shows the model characteristics of features in the first model of the ensemble of models.

TABLE 6

| Features | st_Oscillibacter | sa_Simonsiella | st_Cuneatibacter | sa_Phocaeicola | st_Pseudoflavonifractor |
|---|---|---|---|---|---|
| Q1 | 0.02 | 0 | 0.01 | 0 | 0 |
| Q3 | 0.13 | 0.02 | 0.09 | 0.01 | 0.01 |
| Q2a | 0.02 | 0 | 0.02 | 0.01 | 0 |
| Q2b | 0.14 | 0.01 | 0.1 | 0 | 0.01 |
| Min Model Score | | | 0.1 | | |
| Max Model Score | | | 3.99 | | |
| Threshold | | | 1.09 | | |
| Numerator/ Denominator Feature | Numerator | Numerator | Numerator | Denominator | Numerator |
| Model Type | | | Reverse | | |

As an example, assume that the five taxa in the taxonomic abundance profile obtained by processing the hybrid (saliva, stool) sample combination (in the manner mentioned in Steps 1 and 2) had the following normalised abundances:

Abundance of st_*Oscillibacter* (i.e., feature 1 in training model) in collected stool sample: 0.002080

Abundance of sa_*Simonsiella* (i.e., feature 2 in training model) in collected stool sample: 0.000881

Abundance of st_*Cuneatibacter* (i.e., feature 3 in training model) in collected stool sample: 0.008321

Abundance of sa_*Phocaeicola* (i.e., feature 4 in training model) in collected stool sample: 0.004403

Abundance of st_*Pseudoflavonifractor* (i.e., feature 5 in training model) in collected stool sample: 0.000000

At step 5, Using Q1 and Q3 values corresponding to each training model feature in ensemble model, and the transformation is applied to the above normalised abundances. Following are the exemplary calculated transformed abundances:

Transformed abundance ($F_{st\_Oscillibacter}$): 0.000000
Transformed abundance ($F_{sa\_Simonsiella}$): 0.049407
Transformed abundance ($F_{st\_Cuneatibacter}$): 0.000000
Transformed abundance ($F_{sa\_Phocaeicola}$): 0.208317
Transformed abundance ($F_{st\_Pseudoflavonifractor}$): 0.000000

The transformed abundance of individual features as obtained above are then used appropriately in the candidate model equation ($CM_K$) (as replicated below), and numerator and denominator sums are computed as per the rules:

$$CM_K = \frac{\sum F_{numerator}}{\sum F_{denominator}} \dots \text{when } F_{numerator} > 0$$

and $$F_{denominator} > 0$$

or, $$CM_K = \frac{\sum F_{numerator} + 1}{\sum F_{denominator} + 1} \dots \text{when either}$$

$$F_{numerator}$$

or $$F_{denominator} = 0$$

In this case, the values obtained are as follows—
Numerator sum: 0.049407
Denominator sum: 0.208317

At step 6, the sample model score (MS) is computed using above Numerator sum and Denominator sum. The sample model score (MS) is then transformed into scaled model score (SMS) (having values between −1 and +1, using following rules—

$$SMS = (MS - T_{max}) / (CMS_{K_{max}} - T_{max}), \dots \dots \text{when } MS >= T_{max},$$

and $$SMS = (MS - T_{max}) / (T_{max} - CMS_{K_{min}}), \dots \dots \text{when } MS < T_{max},$$

Wherein, $T_{max}$, $CMS_{K_{max}}$, and $CMS_{K_{min}}$ values corresponding to the respective model is used.

For this purpose, the values of threshold: 1.094114, a maximum model score: 3.985944, a minimum model score:

0.102631 for Model 1 provided against 'Ensemble Training Model' (as mentioned in Table 6) are employed.

Model score (MS): 0.237172

Scaled model score (SMS): −0.864303

At step 7, the SMS is then used for predicting the risk of PCOS of the individual from whom the saliva sample and the stool samples are obtained. The steps from step 4 to 6 are repeated for all the ten single models in the final ensemble model and finally mean of all the Final prediction scores of the ten single models in ensemble is calculated and the class prediction is done based on final mean prediction score (FMPS) obtained.

$$FMPS = -0.546785$$

Since both forward model and reverse model are evaluated wherein the final selected model is then used for classification or prediction—the final selected ensemble model in current example is a reverse model. Hence the final mean prediction score value is calculated as (FMPS*−1)

Final pred_score is 0.546785

Since the value is >0, the prediction class is "B" i.e. Risk Category is "PCOS".

At step 8, similarly, for the single best model, all the steps are repeated for the single model and the final prediction score is calculated using sample model scores (SMS) and the class prediction is done based on final prediction score obtained for that sample.

The above listed features are subject to changes based on the site of extraction of sample. In an example scenario, if only saliva or only stool sample is considered then the selected features set would be different and would be under scope of the disclosure. Also, the names of one or more of the microbes mentioned above, because of reasons like change in the version of the classification database, change in name of the microbe and any alternate names of the same set of microbes are well within the scope of the invention.

The described methodology can be adopted for other datasets to arrive at additional region/age or other metadata specific models and recommendations.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

This disclosure relates generally a method and system for assessment of PCOS. The polycystic ovarian syndrome (PCOS) is a hormonal disorder common among women of reproductive age that causes infertility and affects overall health of the woman. As PCOS is common and curable cause of infertility, an efficient early screening to assess a potential risk of PCOS can ensure early treatment. The current state-of-the-art techniques include diagnostic, screening solutions, imaging techniques which are invasive, complex, expensive. The disclosure is a supervised machine learning algorithm on the samples of individuals to arrive at a panel of biological features/indicators/markers/signatures that can accurately stratify/classify/group individuals into 'PCOS' and 'healthy' based upon the differences in the composition of the gut/oral microbial communities.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method for risk assessment of poly-cystic ovarian syndrome (PCOS) disorder of a subject, comprising the steps of:

collecting a saliva sample and a stool sample of the subject whose risk of PCOS disorder is to be assessed;

extracting microbial deoxyribonucleic acid (DNA) sequences from each of the saliva sample and the stool sample, individually;

determining a quantitative abundance of: (i) each of a plurality of predetermined microbes associated with the saliva sample and (ii) each of a plurality of predetermined microbes associated with the stool sample, individually, from respective extracted DNA sequences, using a first set of probes and a second set of probes specific to each of the plurality of predetermined microbes associated with the saliva sample and the stool sample respectively, through a multiplex quantitative Polymerase Chain Reaction (qPCR) technique;

collating, via one or more hardware processors, the quantitative abundance of: (i) each of the plurality of predetermined microbes associated with the saliva sample and (ii) each of the plurality of predetermined microbes associated with the stool sample, to obtain a hybrid abundance matrix;

determining, via the one or more hardware processors, a model score based on the hybrid abundance matrix, using a pre-determined machine learning (ML) model;

performing, via the one or more hardware processors, risk assessment of the subject, based on the model score and a predefined threshold value; and providing a designed personalized microbial concoction to the subject to enable amelioration of PCOS based on the risk assessment of the subject, wherein the designed personalized microbial concoction for the subject consisting of a specific composition of microbes employable for the subject assessed as having poly-cystic ovarian syndrome (PCOS) disorder for ameliorating the PCOS disorder.

2. The method of claim 1, wherein:

(i) the plurality of predetermined microbes associated with the saliva sample comprises: *Phocaeicola, Simonsiella, Massiliprevotella, Streptobacillus, Rothia*, and *Slackia*; and (ii) the plurality of predetermined microbes associated with the stool sample comprises: *Oscillibacter, Cuneatibacter, Faecalibacterium, Pseudoflavonifractor, Gordonibacter, Neisseria, Fusobacterium, Lactococcus*, and *Lactobacillus*.

3. The method of claim 1, wherein the first set of probes specific to each of the plurality of predetermined microbes associated with the saliva sample are utilized in a first multiplex qPCR run, and a second multiplex qPCR run, to determine the quantitative abundance of each of the plurality of predetermined microbes associated with the saliva sample, and wherein:

(i) the plurality of predetermined microbes, the quantitative abundance of which are being determined through the first multiplex qPCR run are: *Phocaeicola, Simonsiella, Massiliprevotella* and *Streptobacillus*; and (ii) the plurality of predetermined microbes, the quantitative abundance of which are being determined through the second multiplex qPCR run are: *Phocaeicola, Simonsiella, Rothia*, and *Slackia*.

4. The method of claim 1, wherein the second set of probes specific to each of the plurality of predetermined microbes associated with the stool sample are utilized in a third multiplex qPCR run, fourth multiplex qPCR run, and a fifth multiplex qPCR run, to determine the quantitative abundance of each of the plurality of predetermined microbes associated with the stool sample, and wherein:

(i) the plurality of predetermined microbes, the quantitative abundance of which are being determined through the third multiplex qPCR run are: *Oscillibacter, Cuneatibacter, Pseudoflavonifractor*, and *Gordonibacter*, and (ii) the plurality of predetermined microbes, the quantitative abundance of which are being determined through the fourth multiplex qPCR run are: *Oscillibacter, Cuneatibacter, Faecalibacterium* and *Neisseria*; and (iii) the plurality of predetermined microbes, the quantitative abundance of which are being determined through the fifth multiplex qPCR run are: *Fusobacterium, Lactococcus, Faecalibacterium*, and *Lactobacillus*.

5. The method of claim 1, wherein the pre-determined machine learning (ML) model is an ensemble ML model that is built using a microbial abundance data corresponding to a plurality of training saliva samples and a plurality of training stool samples.

6. The method of claim 1, wherein the plurality of predetermined microbes associated with the saliva sample and the plurality of predetermined microbes associated with the stool sample are features of the pre-determined machine learning (ML) model.

7. The method of claim 3, wherein one or more predetermined microbes out of the plurality of predetermined microbes associated with the saliva sample, are common to the first multiplex qPCR run and the second multiplex qPCR run for determining the quantitative abundance, and wherein the one or more predetermined microbes that are common to the first multiplex qPCR run and the second multiplex qPCR run are determined based on (i) a median abundance of each of the plurality of predetermined microbes obtained from the plurality of training saliva samples, (ii) a frequency of occurrence of each of the plurality of predetermined microbes constituting the ensemble ML model.

8. The method of claim 4, wherein one or more predetermined microbes out of the plurality of predetermined microbes associated with the stool sample are common to the third multiplex qPCR run and the fourth multiplex qPCR run for determining the quantitative abundance, and wherein the one or more predetermined microbes that are common to the third multiplex qPCR run and the fourth multiplex qPCR run are determined based on (i) a median abundance of each of the plurality of predetermined microbes obtained from the plurality of training stool samples, (ii) a frequency of occurrence of each of the plurality of predetermined microbes constituting the ensemble ML model.

9. The method of claim 4, wherein one or more predetermined microbes out of the plurality of predetermined microbes associated with the stool sample are common to the fourth multiplex qPCR run and the fifth multiplex qPCR run for determining the quantitative abundance, and wherein the one or more predetermined microbes that are common to the fourth multiplex qPCR run and the fifth multiplex qPCR run are determined based on (i) a median abundance of each of the plurality of predetermined microbes obtained from the plurality of training stool samples, (ii) a frequency of occurrence of each of the plurality of predetermined microbes constituting the ensemble ML model.

10. The method of claim 6, wherein designing the personalized microbial concoction comprises designing one or a combination of probiotic and antibiotic microbial candidates based on the features constituting the ML model, and wherein designing of the one or the combination of probiotic and antibiotic candidates is performed by mapping the features constituting the ML model to complete set of microbes or a pre-defined subset of the microbes, wherein the features comprise microbial taxa.

11. The method of claim 10, wherein designing of the one or the combination of probiotic and antibiotic microbial candidates comprises:

1) Computing pair-wise correlations between abundances of the microbial taxa constituting the ML model and the abundances corresponding to the complete set of microbial taxa represented by microbial markers computed individually from (a) the subset of training samples corresponding to a healthy class (A) that is a class of samples that were taken from patients diagnosed to be free of PCOS, and (b) a diseased class (B) that is a class of samples that were taken from PCOS affected subjects, wherein both the samples belonging to the healthy class (A) and the diseased class (B) are used as training data for generating the ML model;

2) positive and negative interactions between the microbial taxa constituting the ML model and all other taxa in the healthy class and the diseased class of the training samples are deduced using critical correlation

64

(r) value as the cut-off such that inter-taxa correlation index values greater than +r value are affiliated as 'positive interactions', while those less than-r value are affiliated as 'negative interactions';

3) repeating steps 1 and 2 for a predefined numbers of times and considering only those interactions as relevant that appear in at least 70% of iterations with the critical correlation (r) value cut-off and retained the relevant interactions;

4) using a set of predefined rules to select relevant microbial candidates for designing the probiotic and/or antibiotic microbial candidates based on the retained model taxa interactions.

12. The method of claim 11, wherein the microbial markers in the ML model which are higher in the diseased class are suitable antibiotic targets for which existing antibiotics to be used or designed from the microbial taxa which are having the negative interactions with target marker microbe, and the probiotics are targeted at the microbial markers found to be abundant in case of healthy class subjects in the training model, where existing probiotics to be used or designed from the microbes that are positively interacting with the target marker microbe.

* * * * *

SEQUENCE LISTING

```
Sequence total quantity: 15
SEQ ID NO: 1              moltype = RNA  length = 1528
FEATURE                  Location/Qualifiers
source                   1..1528
                         mol_type = rRNA
                         organism = Phocaeicola faecicola
                         strain = AGMB03916
SEQUENCE: 1
acaatgaaga gtttgatcct ggctcaggat gaacgctagc tacaggctta acacatgcaa   60
gtcgaggggc agcgggattg aagcttgctt caattgccgg cgaccggcgc acgggtgagt  120
aacacgtatc caaccttccg tttactcggg gatagccttt cgaaagaaag attaataccc  180
gatagtatgg tgagattgca tgatagcacc attaaagatt catcggtaaa cgatggggat  240
gcgttccatt aggtagtagg cggggtaacg gcccacctag cctgcgatgg atagggttc   300
tgagaggaag gtcccccaca ttggaactga gacacggtcc aaactcctac gggaggcagc  360
agtgaggaat attggtcaat gggcgagagc ctgaaccagc caagtagcgt gaaggatgaa  420
ggtcctacgg attgtaaact tcttttataa gggaataaaa cgctccacgt gtggagcctt  480
gtatgtacct tatgaataag catcggctaa ctccgtgcca gcagccgcgg taatacggag  540
gatgcgagcg ttatccggat ttattgggtt taaagggagc gcagacggga tgttaagtca  600
gctgtgaaag tttgcggctc aaccgtaaaa ttgcagttga tactggcgtt cttgagtgca  660
gttgaggtgt gcggaattcg tggtgtagcg gtgaaatgct tagatatcac gaagaactcc  720
gattgcgaag gcagctcact aaactgtaac tgacgttcat gctcgaaagt gtgggtatca  780
aacaggatta gataccctgg tagtccacac ggtaaacgat ggatactcgc tgttggcgat  840
atacggtcag cggccaagcg aaagcgttaa gtatcccacc tggggagtac gccggcaacg  900
gtgaaactca aaggaattga cggggggccg cacaagcgga ggaacatgtg gtttaattcg  960
atgatacgcg aggaacctta cccgggctta aattgcagag gaatgatctg gaaacaggtc 1020
agtcttcgga cttctgtgaa ggtgctgcat ggttgtcgtc agctcgtgcc gtgaggtgtc 1080
ggcttaagtg ccataacgag cgcaacccct gtggtcagtt actaacaggt aatgctgagg 1140
actctggcca gactgccatc gtaagatgtg aggaaggcgg ggatgacgtc aaatcagcac 1200
ggcccttacg tccggggcta cacacgtgtt acaatgggag gtacagaagg ctgcgacccg 1260
gcgacgggca gctaatccca aaagcctctc tcagttcgga ctggagtctg caacccgact 1320
```

```
ccacgaagct ggattcgcta gtaatcgcgc atcagccacg gcgcggtgaa tacgttcccg    1380
ggccttgtac acaccgcccg tcaagccatg aaagccgggg gtacctgaag tgcgtaaccg    1440
caaggagcgt cctagggtaa aaccggtaat tggggctaag tcgtaacaag gtagccgtac    1500
cggaaggtgc ggctggaaca cctccttt                                       1528

SEQ ID NO: 2          moltype = RNA   length = 1465
FEATURE               Location/Qualifiers
source                1..1465
                      mol_type = rRNA
                      organism = Simonsiella muelleri
                      strain = ATCC 29453
SEQUENCE: 2
attgaacgct ggcggcatgc tttacacatg caagtcggac ggcagcgggg tagtgcttgc    60
attactgccg gcgagtggcg aacgggtgag tataatattg gaacgtaccg agtaatgggg    120
gataactatc cgaaaggatg gctaataccg catacgtcct gagggagaaa gcggggggaca   180
ggcaactgcc tcgcgttatt tgagcggcca atatcggatt agctagttgg tggggtaaag    240
gcttaccaag gcgacgatcc gtagcgggtc tgagaggatg atccgccaca ctgggactga    300
gacacggccc agactcctac gggaggcagc agtggggaat tttggacaat gggggggaacc   360
ctgatccagc catgtcgcgt gtatgaagaa ggccttaggg ttgtaaagta cttttgttag    420
ggaagaaaag gcatttgcta atatcagatg ctgatgacgg tacctaaaga ataagcaccg    480
gctaactacg tgccagcagc cgcggtaata cgtagggtgc gagcgttaat cggaattact    540
gggcgtaaag cgagcgcaga cggttactta agcaagatgt gaaatccccg agctcaactt    600
gggaactgcg ttttgaactg ggtagctaga gtgtgtcaga ggggggtaga attccacgtg    660
tagcagtgaa atgcgtagag atgtggagga ataccgatgg cgaaggcagc ccctcgggat    720
agcactgacg ttcatgctcg aaagcgtggg tagcaaacag gattagatac cctggtagtc    780
cacgccctaa acgatgtcaa ttagctgttg gggcactaga tgccttagta gcgaagctaa    840
cgcgtgaaat tgaccgcctg gggagtacgg tcgcaagatt aaaactcaaa ggaattgacg    900
gggacccgca caagcggtgg atgatgtgga ttaattcgat gcaacgcgaa gaaccttacc    960
tggtcttgac atgtacggaa tctctcagag acggagagt gccttcggga gccgtaacac      1020
aggtgctgca tggctgtcgt cagctcgtgt cgtgagagt tgggttaagt cccgcaacga      1080
gcgcaaccct tgtcattagt tgccatcatt tggttgggca ctctaatgag actgccggtg    1140
acaaaccgga ggaaggtggg gatgacgtca agtcctcatg gcccttatga ccagggcttc    1200
acacgtcata caatggtcgg tacagagggt agccaagccg cgaggtggag ccaatcccaa    1260
aaaaccgatc gtagtccgga ttgcactctg caactcgagt gcatgaagtc ggaatcgcta    1320
gtaatcgcag gtcagcatac tgcggtgaat acgttcccgg gtcttgtaca caccgcccgt    1380
cacaccatgg gagtgggggga taccagaagt aggtagaata accgcgagga gttcgcttac   1440
cacggtatgc ttcatgactg gggtg                                          1465

SEQ ID NO: 3          moltype = RNA   length = 1493
FEATURE               Location/Qualifiers
source                1..1493
                      mol_type = rRNA
                      organism = Massiliprevotella massiliensis
                      strain = Marseille P2439
SEQUENCE: 3
agagtttgat cctggctcag gatgaacgct agctacaggc ttaacacatg caagtcgagg    60
ggaaacgata gggaaagctt gctttycyta ggcgtcgacc ggcgcacggg tgagtaacgc    120
gtatccaacc tgcccatgtc tggggaataa cccgtcgaaa ggcggactaa ctccccatgg    180
tctccgatga ggacatctga attggagtaa agcttcgcgg acatggatgg ggatgcgtct    240
gattaggtag taggcggggt aacggcccac ctagcctacg atcagtaggg gttctgagag    300
gaaggtcccc cacattggaa ctgagacacg gtccaaactc ctacggggag gcagcagtgag   360
gaatattggt caatggacga gagtctgaac cagccaagta gcgtgcagga tgacggccct    420
atgggttgta aactgctttt gcgcggggat aacaccctcc acgtgctgga ggtctgcagg    480
taccgcgcga ataaggaccg gctaattccg tgccagcagc cgcggtaata cggaaggtcc    540
gggcgttatc cggatttatt gggtttaaag ggagcgtagg ccgtgaggca agcgtgttgt    600
gaaatgtagg cgcccaacgt ctgcactgca gcgcgaactg ccccacttga gtgcgcgcaa    660
cgccggcgga actcgtcgtg tagcggtgaa atgcttagat atgacgaaga accccgattg    720
cgaaggcagc tggcgggagc gtaactgacg ctgaagctcg aaagcgcggg tatcgaacag    780
gattagatac cctggtagtc cgcgcggtaa acgatggatg cccgctgtgg cgcgcctggc    840
gtgccgcggc taagcgaaag cattaagcat cccacctggg gagtacgccg gcaacggtga    900
aactcaaagg aattgacggg ggcccgcaca agcggaggaa catgtggttt aattcgatga    960
tacgcgagga accttacccg gcttgaact gcaggagaac gattcagaga tgatgaggtc      1020
cttcgggact cctgtggagg tgctgcatgg ttgtcgtcag ctcgtgccgt gaggtgtcgg    1080
cttaagtgcc ataacgagcg caacccctct ccgtagttgc catcgggtaa tgccggtga     1140
tctgcgcgaca ctgccaccgt aaggtgtgag gaaggtgggg atgacgtcaa atcagcacgg   1200
cccttacgtc cggggccaca cacgtgttac aatggccgtc acagagggga gccgggcgac    1260
cggctcatga tccttaaaaa cggtctcagt cggactgggg gtctgcaacc cgaccccacg    1320
aagctggatt cgctagtaat cgcgcatcag ccatggcgcg gtgaatacgt tcccgggcct    1380
tgtacacacc gcccgtcaag ccatgaaagc cggggggcgcc tgaagtccgt gaccgcaagg    1440
atcggcctag ggcgaaactg gtgattgggg ctaagtcgta acaaggtagc cgt            1493

SEQ ID NO: 4          moltype = RNA   length = 1475
FEATURE               Location/Qualifiers
source                1..1475
                      mol_type = rRNA
                      organism = Streptobacillus notomytis
                      strain = AHL 370-1
SEQUENCE: 4
agagtttgat cctggctcag gatgaacgct gacagaatgc ttaacacatg caaatctatg    60
```

```
ttaattatgt aagcttgctt agataagaga catggtggac tggtgagtaa cgtgtaaaga  120
acttacctct tagactggga taaccattag aaatgatgga taatactaga tattattaga  180
agtgggcatc tactttttaat gaaaggagag attgctaaga gagagctttg catcctatta  240
gctagttggt ggggtaaagg cctaccaagg cgatgatagg tagccggccc gagagggtga  300
acggccacaa ggggactgag atacggccct tactcctacg ggaggcagca gtggggaata  360
ttggacaatg gaggaaactc tgatccagca attctgtgtg cacgaagaag gttttcggat  420
tgtaaagtgc tttcagtagg gaagaagaaa gtgacggtac ctacagaaga agcgacggct  480
aaatacgtgc cagcagccgc ggtaaatacg atgtcgcaag cgttatccgg aattattggg  540
cttaaagggc atctaggcgg tctaacaagt tgaaggtgaa agctgtggc tcaaccatag  600
tcttgcctac aaaactgtca gactagagta ctgggaaggt gggtggaact acacgagtag  660
aggtgaaatt cgtagatatg tgtaggaatg ccgatgatga agataactca ctggacagaa  720
actgacgctg aagtgcgaaa gctaggggag caaacaggat tagataccct ggtagtccta  780
gctgtaaacg atgatcactg ggtgtggggg tataagcctc tgtgccgaag caaaagcgat  840
aagtgatccg cctggggagt acgtacgcaa gtatgaaact caaaggaatt gacgggggacc  900
cgcacaagtg gtggagcatg tggtttaatt cgacgcaacg cgaggaacct taccagatct  960
tgacatactc ggaataagat ggaagcatct tagtgccttc gggaaccgag atacaggtgt  1020
tgcatggctg tcgacagctc gtgtcgtgag atgttgggtt aagtcccgca acgagcgaaa  1080
cccctatcat tagttgccat cattaagttg gggactctaa tgaaactgcc cgcgacgagc  1140
gggaggaagg tggggatgac gtcaagtcat catgcccctt atgatctggg ctacacacgt  1200
gctacaatgg gtagtacaaa gaggagctaa gcagtgatgt ggagcaaatc ttaaaagcta  1260
ctctcagttc ggattgaagt ctgcaactcg acttcatgaa gttggaatca ctagtaatcg  1320
caaatcagca atgttgcggt gaatacgttc tcgggtcttg tacacaccgc ccgtcacacc  1380
acgagagtta gttgcacctg aagttactgg cctaaccgta aggaggggaag tacctaaggt  1440
gtgattagtg attggggtga agtcgtaaca aggta                              1475
```

```
SEQ ID NO: 5             moltype = RNA  length = 1533
FEATURE                  Location/Qualifiers
source                   1..1533
                         mol_type = rRNA
                         organism = Rothia halotolerans
                         strain = YIM 90716
SEQUENCE: 5
agagattaga gtttgatcct ggctcaggac gaacgctggc ggcgtgctta acacatgcaa  60
gtcgaacgct gaagcaccca gcttgctggg tgtggatgag tggcgaacgg gtgagtaata  120
cgtgagtgac cttcccttga ctctgggata agcccgggaa actgggtcta ataccggata  180
tgcactatca cctgcctggg tggtggtgga aagggttttg tactggtctt ggatgggctc  240
acggcctatc agctagttgg tgaggtaatg gcttaccaag cgacgacgg gtagccggcc  300
tgagagggtg accggccaca ctgggactga cacacggccc agactcctac gggaggcagc  360
agtggggaat attgcacaat gggcgcaagc ctgatgcagc gacgccgcgt gagggatgac  420
ggccttcggg ttgtaaacct ctttcagcag ggaagaagcg aaagtgacgg tacctgcaga  480
agaagcgccg gctaactacg tgccagcagc cgcggtaata cgtagggcgc aagcgttgtc  540
cggaattatt gggcgtaaag agctcgtagg cggcttgtcg cgtctgctgt gaaagcccgg  600
ggcttaaccc cgtggtgtgc agtgggtacg ggcaggctag ggtgcagtag ggagagactgg  660
aattcctggt gtagcggtga aatgcgcaga tatcaggagg aacaccgatg gcgaaggcag  720
gtctctgggc tgttactgac gctgaggagc gaaagcatgg ggagcggaca ggattagata  780
ccctggtagt ccatgccgta aacgttgggc actaggtgtg ggggacattc cacgtttttcc  840
gcgccgtagc taacgcatta agtgccccgc ctggggagtg acggccgcaag gctaaaactc  900
aaaggaattg acgggggccc gcacaagcgg cggagcatgt ggattaattc gatgcaacgc  960
gaagaacctt accaaggctt gacatacact ggatcgcagc agagatgttg tttcctcttt  1020
gaggctggt tacaggtggt gcatggttgt cgtcagctcg tgtcgtgaga tgttgggtta  1080
agtcccgcaa cgagcgcaac cctcgttcta tgttgccagc acgtgatggt ggggactcat  1140
aggagactgc cggggtcaac tcggaggaag gtggggatga cgtcaaatca tcatgcccct  1200
tatgtcttgg gcttcacgca tgctacaatg gccggtacaa tgggttgcga tactgtgagg  1260
tggagctaat cccaaaaagc cggtctcagt tcggattggg gtctgcaact cgacccatg  1320
aagtcggagt cgctagtaat cgcagatcag caacgctgat aacgt tcccgggcct  1380
tgtacacacc gcccgtcaag tcacgaaagt tggtaacacc cgaagccgat ggcctaaccc  1440
ttgtggaggg agtcgtcgaa ggtgggactg cgattgggga ctaagtcgta acaaggtagc  1500
cgtaccggaa ggtgcggctg gatcacctcc taa                              1533
```

```
SEQ ID NO: 6             moltype = RNA  length = 1463
FEATURE                  Location/Qualifiers
source                   1..1463
                         mol_type = rRNA
                         organism = Slackia piriformis
                         strain = YIT 12062
SEQUENCE: 6
gatgaacgct ggcggcgtgc ctaacacatg caagtcgaac ggttaaggcg ccttcgggcg  60
cgcatagagt ggcgaacggg tgagtaacac gtgaccaacc tgcccctcc tccgggacaa  120
cctcgggaaa ccgaggctaa taccggatgg tcccgccggg gggcatggcc gggcgggaaa  180
agcccaggcg ggaggggatg gggtcgcggc ccatcaggta gtaggcgggg tgacggccca  240
cctagctgac gacgggtagc cgcgctgaga ggcggaccgg ccacattggg actgagacac  300
ggcccagact cctacgggag gcagcagtgg ggaattttgc gcaatggggg aaaccctgac  360
gcagcaacgc cgcgtgcggg acgaaggcct tcgggtcgta aaccgctttc agcagggaag  420
aagaatgacg gtacctgcag aagaagcccc ggctaactac ggcgcggtaat  480
acgtaggggg cgagcgttat ccggattcat tgggcgtaaa gcgcgcgtag cgtccttc  540
aagcggcacc gtcgaagccg ggggctcaac cccggaagc gggccgaact ggggggatcg  600
agtgcggtag gggaaggcgg aattcccggt gtagcggtga aatgcgcaga tatcgggaag  660
aacaccgacg cgaaggcag ccttctgggc gccactgac gctgaggcgc gaaagctggg  720
ggagcgaaca ggattagata ccctggtagt cccagccgta aacgatgggc gctaggtgtg  780
```

-continued

```
gggggagatg tccctccgtg ccgcagccaa cgcattaagc gccccgcctg gggagtacgg   840
ccgcaaggct aaaactcaaa ggaattgacg ggggcccgca caagcagcgg agcatgtggc   900
ttaattcgaa gcaacgcgaa gaaccttacc agggcttgac atcaccgtga gccgccggag   960
acggcggggc cgaaaggagc ggtgacaggt ggtgcatggc tgtcgtcagc tcgtgtcgtg  1020
agatgttggg ttaagtcccg caacgagcgc aacccccgcc gcgtgttgcc agcattgagt  1080
tgggcactcg cgcgggactg ccggcgtcaa gccggaggaa ggtgggggacg acgtcaagtc  1140
atcatgcccc tcatgccctg ggctgcacac gtgctacaat ggccggtaca gcgggctgcg  1200
acgccgcgag gcggagcgaa tcccacaaag ccggcccccag ttcggaccgc aggctgcaac  1260
ccgcctgcgc gaagccggag ttgctagtaa tcgcggatca gcatgccgcg gtgaatacgt  1320
tcccgggcct tgtacacacc gcccgtcaca ccacccgagt cgtctgcacc cgaagccgcc  1380
ggccgaaccc gcaaggggcg gaggcgtcga aggtgtggag ggtgaggggg gtgaagtcgt  1440
aacaaggtag ccgtaccgga agg                                          1463
```

SEQ ID NO: 7          moltype = RNA   length = 1530
FEATURE               Location/Qualifiers
source                1..1530
                      mol_type = rRNA
                      organism = Oscillibacter valericigenes
                      strain = Sjm18-20
SEQUENCE: 7

```
tttatagaga gtttgatcct ggctcaggac gaacgctggc ggcgtgctta acacatgcaa   60
gtcgaacgga gcacccttga ttgaggtttc ggccaaatga gaggaatgct tagtggcgga  120
ctggtgagta acgcgtgagg aacctgcctt tcagagggggg acaacagttg gaaacgactg  180
ctaataccgc atgatacatt tgggcgcacat cgcttgaatg tcaaagatttt atcgctgaaa  240
gatggcctcg cgtctgatta gatagttggt gaggtaacgg cccaccaagt cgacgatcag  300
tagccggact gagaggttga ccggccacat tgggactgag atacggccca gactcctacg  360
ggaggcagca gtggggaata ttgggcaatg gacgcaagtc tgacccagca acgccgcgtg  420
aaggaagaag gctttcgggt tgtaaacttc ttttaagggg gaagagtaga agacggtacc  480
ccttgaataa gccacggcta actacgtgcc agcagccgcg gtaatacgta ggtggcaagc  540
gttgtccgga tttactgggt gtaaagggcg tgtagccggg aaggtaagtc agatgtgaaa  600
tctgggggct caacctccaa actgcatttg aaactacttt tcttgagtat cggagaggta  660
atcggaattc cttgtgtagc ggtgaaatgc gtagatataa ggaagaacac cagtggcgaa  720
ggcggattac tggacgacaa ctgacggtga ggcgcgaaag cgtggggagc aaacaggatt  780
agataccctg gtagtccacg ctgtaaacga tcaatactag gtgtgcgggg actgacccc   840
tgcgtgccgc agttaacaca ataagtattg cacctgggga gtacgatcgc aaggttgaaa  900
ctcaaaggaa ttgacggggg cccgcacaag cggtggatta tgtggtttaa ttcgaagcaa  960
cgcgaagaac cttaccagga cttgacatcc tactaacgag gtagagatac gtcaggtgcc  1020
cttcggggaa agtagagaca ggtggtgcat ggttgtcgtc agctcgtgtc gtgagatgtt  1080
gggttaagtc ccgcaacgag cgcaaccct attgttagtt gctacgcaag agcactctag  1140
cgagactgcc gttgacaaaa cggaggaagg tggggacgac gtcaaatcat catgcccctt  1200
atgtcctggg ctacacacgt aatacaatgg cggtcaacag agggatgcaa agccgtgagg  1260
tggagcgaac ccctaaaagc cgtctcagtt cggatcgcag gctgcaactc gcctgcgtga  1320
agtcggaatc gctagtaatc gcggatcaga atgccgcggt gaatacgttc ccgggccttg  1380
tacacaccgc ccgtcacacc atgagagtcg ggaacacccg aagtccgtag cctaacagca  1440
atgagggcgc ggccgaaggt gggtttgata attggggtga agtcgtaaca aggtagccgt  1500
atcggaaggt gcggctggat cacctccttt                                   1530
```

SEQ ID NO: 8          moltype = RNA   length = 1485
FEATURE               Location/Qualifiers
source                1..1485
                      mol_type = rRNA
                      organism = Cuneatibacter caecimuris
                      strain = BARN-424-CC-10
SEQUENCE: 8

```
agagtttgat cctggctcag gatgaacgct ggcggcgtgc ttaacacatg caagtcgaac   60
gaagcagttg cgaggaagtt ttcggatgga attgcgattg actgagtggc ggacgggtga  120
gtaacgcgtg ggtaacctgc ctcacacagg gggataacag ttagaaatga ctgctaatac  180
cgcataaccc gctagggccg catggcccgg acggaaaaga aatatcggtg tgagatggac  240
ccgcgtctga ttagctggtt ggtagggtaa cggcctacca aggcgacgat cagtagccga  300
cttgagagag tgatcggcca cattgggact gagacacgg ccaaactcct acgggaggca  360
gcagtgggga atattgcaca atgggggaaa ccctgatgca gcgacgccgc gtgactgaag  420
aagtacttcg gtatgtaaag gtctatcagc agggaagaag aaagacggta cctgactaag  480
aagccccggc taactacgtg ccagcagccg cggtaatacg taggggggcaa gcgttatccg  540
gatttactgg gtgtaaaggg agcgtaggcg gtagcgcaag tcagaagtga agcccgggct  600
ctcaaccccg cggactgctt ttgaaactgc gtaactggag tgcaggagag gtaagtggaa  660
ttcctagtgt agcggtgaaa tgcgtagata ttaggaggaa caccagtggc gaaggcggct  720
tactggactg taactgacgc tgaggctcga aagcgtgggg agcaaacagg attagatacc  780
ctggtagtcc acgctgtaaa cgatgaatac taggtgtcgg ggagcaaagc tcttcggtgc  840
cgtcgcaaac gcagtaagta ttccacctgg ggagtacgtt cgcaagaatg aaactcaaag  900
gaattgacgg ggacccgcac aagcggtgga gcatgtggtt taattcgaag caacgcgaag  960
aaccttacct gctcttgaca tcccctgac gcagaggtaa tgctctgttt ctttcgagac  1020
aggggagaca ggtggtgcat ggttgtcgtc agctcgtgtc gtgagatgtt gggttaagtc  1080
ccgcaacgag cgcaacccctt atccttagta gccagcaggt agagctgggc actctgggga  1140
gactgccggg gataacccgg aggaaggtgg ggatgacgtc aaatcatcat gccccttatg  1200
agcagggcta cacacgtgct acaatgggcgt aaacagaggg aagcgaaggg gtgacctgaa  1260
gcgaatctca aaaataacgt ctcagttcgg attgtagtct gcaactcgac tacatgaagc  1320
tggaatcgct agtaatcgcg aatcagaatg tcgcggtgaa tacgttcccg ggtcttgtac  1380
acaccgcccg tcacaccatg ggagtcggta acgcccgaag ccagtgacct aacctgaaaa  1440
gggaggagct gtcgaaggcg ggactggtaa ctggggtgaa gtcgt                  1485
```

-continued

```
SEQ ID NO: 9          moltype = RNA  length = 1462
FEATURE               Location/Qualifiers
source                1..1462
                      mol_type = rRNA
                      organism = Faecalibacterium prausnitzii
                      strain = ATCC 27768
SEQUENCE: 9
gatcctggct caggcgaacg ctggcgcgc gcctaacaca tgcaagtcga acgagcgaga   60
gagagcttgc tttctcaagc gagtggcgaa cgggtgagta acgcgtgagg aacctgcctc  120
aaagagggggg acaacagttg gaaacgactg ctaataccgc ataagcccac gacccggcat  180
cgggtagagg gaaaaggagc aatccgcttt gagatggcct cgcgtccgat tagctagttg  240
gtgaggtaac ggcccaccaa ggcgacgatc ggtagccgga ctgagaggtt gaacggccac  300
attgggactg agacacggcc cagactccta cgggaggcag cagtggggaa tattgcacaa  360
tgggggaaac cctgatgcag cgacgccgcg tggaggaaga aggtcttcgg attgtaaact  420
cctgttgttg aggaagataa tgacggtact caacaaggaa gtgacggcta actacgtgcc  480
agcagccgcg gtaaaacgta ggtcacaagc gttgtccgga attactgggt gtaaagggag  540
cgcaggcggg aaggcaagtt ggaagtgaaa tccatgggct caacccatga actgctttca  600
aaactgtttt tcttgagtag tgcagaggta ggcggaattc ccggtgtagc ggtggaatgc  660
gtagatatcg ggaggaacac cagtggcgaa ggcggcctac tgggcaccaa ctgacgctga  720
ggctcgaaag tgtgggtagc aaacaggatt agataccctg gtagtccaca ctgtggccga  780
tgtttactag gtgttggagg attgacccct tcagtgccgc agttaacaca ataagtaatc  840
cacctgggga gtacgaccgc aaggttgaaa ctcaaaggaa ttgacggggg cccgcacaag  900
cagtggagta tgtggtttaa ttcgacgcaa cgcgaagaac cttaccaagt cttgacatcc  960
tgcgacgcac atagaaatat gtgtttcctt cgggacgcag agacaggtgg tgcatggttg 1020
tcgtcagctc gtgtcgtgag atgttgggtt aagtcccgca acgagcgcaa cccttatgtg 1080
cagttactac gcaagaggac tctggccaga ctgccgttga caaaacggag gaaggtgggg 1140
atgacgtcaa atcatcatgc cctttatgac ttgggctaca cacgtactac aatggcgtta 1200
aacaaagaga agcaagaccg cgaggtggag caaaaactcag aaacaacgtc ccagttcgga 1260
ctgcaggctg caactcgcct gcacgaagtc ggaattgcta gtaatcgcag atcagcatgc 1320
tgcggtgaat acgttcccgg gccttgtaca caccgcccgt cacaccatga gagccggggg 1380
gacccgaagt cggtagtcta accgcaagga ggacgccgcc gaaggtaaaa ctggtgattg 1440
gggtgaagtc gtaacaaggt ac                                          1462

SEQ ID NO: 10         moltype = RNA  length = 1495
FEATURE               Location/Qualifiers
source                1..1495
                      mol_type = rRNA
                      organism = Pseudoflavonifractor phocaeensis
                      strain = Marseille-P3064
SEQUENCE: 10
agagtttgat cctggctcag gatgaacgct ggcggcgtrc ttaacacatg caagtcgaac   60
ggagtgccta tgaaagagga ttcgtccaat tgattaggtt acttagtggc ggacgggtga  120
gtaacgcgtg aggaacctgc ctcggagtgg ggaataacaa tccgaaagga ttgctaaatac  180
cgcatgatgc agttgggccg catggctctg actgccaaag atttatcgct ctgagatggc  240
ctcgcgtctg attagctagt tggcggggta acggcccacc aaggcgacga tcagtagccg  300
gactgagagg ttgaccggcc acattgggac tgagacaccc cccagactcc tacgggaggc  360
agcagtgggg aatattgggc aatgggcgca agcctgaccc agcaacgccg cgtgaaggaa  420
gaaggctttc gggttgtaaa cttcttttct cagggacgaa gaaaatgacg gtacctgagg  480
aataagccag ggctaactac gtgccagcag ccgcggtaat acgtaggtgg caagcgttat  540
ccggatttac tgggtgtaaa gggcgtgtag gcgggattgc aagtcaggcg tgaaaactat  600
gggcttaacc catagcctgc gtttgaaact gtagttcttg agtgctggag aggcaatcgg  660
aattccgtgt gtagcggtga aatgcgtaga tatacggagg aacaccagtg gcgaaggcgg  720
attgctggac agtaactgac gctgaggcgc gaaagcgtgg ggagcaaaca ggattagata  780
ccctggtagt ccacgccgta aacgatggat actaggtgtg gggggtctga cccccctccgt  840
gccgcagtta acacaataag tatcccacct ggggagtacg atcgcaaggt tgaaactcaa  900
aggaattgac gggggcccgc acaagcggtg gagtatgtgg tttaattcga gcaacgcga  960
agaaccttac cagggcttga catccaacta acgaagcaga gatgcattag gtgcccttcg 1020
gggaaagttg agacaggtgg tgcatggttg tcgtcagctc gtgtcgtgag atgttgggtt 1080
aagtcccgca acgagcgcaa cccttattgt tagttgctac gcaagagcac tctagcgaga 1140
ctgccgttga caaaacggag gaaggtgggg acgacgtcaa atcatcatgc cccttatgtc 1200
ctgggccaca cacgtactac aatggtggtt aacagaggga ggcaataccg cgaggtggag 1260
caaatcccta aaagccatcc cagttcggat tgcaggctga aacccgcctg tatgaagttg 1320
gaatcgctag taatcgcgga tcagcatgcc gcggtgaata cgttcccggg ccttgtacac 1380
accgcccgtc acaccatgag agtcgggaac acccgaagtc cgtagcctaa cagcaatggg 1440
ggcgcggccg aaggtgggtt cgataattgg ggtgaagtcg taacaaggta gccgt        1495

SEQ ID NO: 11         moltype = RNA  length = 1477
FEATURE               Location/Qualifiers
source                1..1477
                      mol_type = rRNA
                      organism = Gordonibacter urolithinfaciens
                      strain = CEBAS 1/15P
SEQUENCE: 11
tgctcaggat gaacgctggc ggcgtgccta acacatgcaa gtcgaacgat taaggcgcct   60
tcgggcgcga atagagtggc gaacgggtga gtaacacgtg accaacctgc cccctccccc  120
gggataacgc gaggaaaccc gcgctaatac cggatactcc gccctcccg catgggaggg  180
gcgggaaagc cccgacggag ggggatgggg tcgcggccca ttaggtagac ggcggggcaa  240
cggcccaccg tgcctgcgat gggtagccgg gttgagagac cgaccggcca cattgggact  300
```

-continued

```
gagatacggc ccagactcct acgggaggca gcagtgggga attttgcgca atggggggaa    360
ccctgacgca gcaacgccgc gtgcgggacg aaggccttcg ggttgtaaac cgctttcagc    420
agggaagaag ttgacggtac ctgcagaaga agccccggct aactacgtgc cagcagccgc    480
ggtaatacgt aggggcgag cgttatccgg attcattggg cgtaaagcgc gcgtaggcgg    540
cccgtcaagc ggaacctcta acccgagggc tcaaccccc gccgggttcc gaactggcag    600
gctcgagtct ggtagaggaa gatggaattc ccggtgtagc ggtggaatgc gcagatatcg    660
ggaagaacac cgatgcgaa ggcagtcttc tgggccgcga ctgacgctga ggcgcgaaag    720
ctgggggagc gaacaggatt agataccctg gtagtcccag ccgtaaacga tgggcgctag    780
gtgtgggggg atcatccctc cgtgccgcag ccaacgcatt aagcgccccg cctggggagt    840
acggccgcaa ggctaaaact caaaggaatt gacggggggcc cgcacaagca gcggagcatg    900
tggcttaatt cgaagcaacg cgaagaacct taccagggct tgacatgctg gtgaagccgg    960
ggaaacccgg tggccgagag gagccagcgc aggtggtgca tggctgtcgt cagctcgtgt    1020
cgtgagatgt tgggttaagt cccgcaacga gcgcaacccc tgccatatgt tgccagcatt    1080
cagttgggga ctcatatggg actgccggcg tcaagccgga ggaaggtggg gacgacgtca    1140
agtcatcatg cctttatgc cctgggctgc acacgtgcta caatggccgg tacaacgggc    1200
cgcgacctgg cgacaggaag cgaatccctc aaagccggcc ccagttcgga tcggaggctg    1260
caacccgcct ccgtgaagtc ggagttgcta gtaatcgcgg atcagcatgc cgcggtgaat    1320
acgttcccgg gccttgtaca caccgcccgt cacaccacc gagtcgtctg cacccgaagc    1380
cgccggccga acccgcaagg ggcggaggcg tcgaaggtgt ggagggtaag gggggtgaag    1440
tcgtaacaag gtagccgtac cggaaggtgc ggctgga                            1477
```

```
SEQ ID NO: 12            moltype = RNA   length = 1463
FEATURE                  Location/Qualifiers
source                   1..1463
                         mol_type = rRNA
                         organism = Neisseria wadsworthii
                         strain = WC 05-9715
SEQUENCE: 12
attgaacgct ggcggcatgc tttacacatg caagtcgaac ggcagcgggg gagagcttgc    60
tttcctgccg gcgagtggcg aacgggtgag taatgcatcg gaacgtaccg agtagtgggg    120
gataactgtc cgaaaggatg gctaataccg catacgcttt gcgaaggaaa gcggggggctc    180
ttaggacctc gcgctattcg agcggccgat gtctgattag ctagttggtg gggtaaaggc    240
ctaccaaggc gacgatcagt agcgggtctg agaggatgat ccgccacact gggactgaga    300
cacggcccag actcctacgg gaggcagcag tggggaattt tggacaatgg ggggaaccct    360
gatccagcca tgccgcgtgt ctgaagaagg ccttcgggtt gtaaaggact tttgtcaggg    420
aagaaaagct tcgggttaat accctggagt gatgacggta cctgaagaat aagcaccggc    480
taactacgtg ccagcagccg cggtaatacg tagggtgcga gcgttaatcg gaattactgg    540
gcgtaaagcg agcgcagacg gttacttaag caggatgtga aatccccggg ctcaacctgg    600
gaactgcgtt ctgaactggg tgactagagt atgtcagagg ggaggataat tccacgtgta    660
gcagtgaaat gcgtagagat gtggaggaat accgatggcg aaggcagccc cctgggataa    720
tactgacgtt catgctcgaa agcgtgggta gcaaacagga ttagatacc tggtagtcca    780
cgccctaaac gatgtcaatt agctgttggg gcacttgatg ctttagtagc gtagctaacg    840
cgtgaaattg accgcctggg gagtacggtc gcaagattaa aactcaaagg aattgacggg    900
gacccgcaca agcggtggat gatgtggatt aattcgatgc aacgcgaaga accttacctg    960
gtcttgacat gtacggaatc ctccggagac ggaggagtgc cttcgggagc cgtaacacag    1020
gtgctgcatg gctgtcgtca gctcgtgtcg tgagatgttg ggttaagtcc cgcaacgagc    1080
gcaaccccttg tcattagttg ccatcattta gttgggcact ctaatgagac tgccggtgac    1140
aaaccggagg aaggtgggga tgacgtcaag tcctcatggc ccttatgacc agggcttcac    1200
acgtcataca atggtcggta cagagggtag ccaagccgcg aggtggagcc aatcccacaa    1260
aaccgatcgt agtccggatt gcactctgca actcgagtgc atgaagtcgg aatcgctagt    1320
aatcgcaggt cagcatactg cggtgaatac gttcccgggt cttgtacaca ccgcccgtca    1380
caccatggga gtggggggata ccagaagtag gtagggtaac cgcaaggagc cgcttacca    1440
cggtatgctt catgactggg gtg                                          1463
```

```
SEQ ID NO: 13            moltype = RNA   length = 1506
FEATURE                  Location/Qualifiers
source                   1..1506
                         mol_type = rRNA
                         organism = Fusobacterium gastrosuis
                         strain = CDW1
SEQUENCE: 13
tgaacgaaga gtttgatcct ggctcaggat gaacgctgac agaatgctta acacatgcaa    60
gtctacttga acttcggttt gggtggcgga cgggtgagta acgcgtaaag aacttgcctc    120
acagactggg acaacatttg gaaacgaatg ctaataccgc atattatgag atatgcgcat    180
gcataactta tgaaagctat atgcgctgtg agagagcttt gcgtcccatt agctagttgg    240
agaggtaacg gctcaccaag gcgatgatgg gtagccggcc tgagagggtg aacggccaca    300
aggggactga gacacggccc ttactcctac gggaggcagc agtggggaat attggacaat    360
ggaccaagag tctgatccag caattctgtg tgcacgatga gttttcgg aatgtaaagt    420
gctttcagtt gggaagaaga aagtgacggt accaacagaa gaagcgacgg ctaaatacgt    480
gccagcagcc gcggtaatac gtatgtcgca agcgttatcc ggatttattg ggcgtaaagc    540
gcgtctaggc ggcatagtaa gtctgatgtg aaaatgcggg gctcaactcc gtattgcgtt    600
ggaaactgct atgctagagt actggagagg taagcggaac tacaagtgta gaggtgaaat    660
tcgtagatat ttgtaggaat gccgatgggg aagccagctt actggacaga tactgacgct    720
aaagcgcgaa aacgtgggta gcaaacagga ttagatacc tggtagtcca cgccgtaaac    780
gatgattact aggtgttggg ggtcgaacct cagcgcccaa gctaacgcga taagtaatcc    840
gcctgggggag tacgtacgca agtatgaaac tcaaaggaat tgacgggggac ccgcacaagc    900
ggtgagcat gtggtttaat tcgacgcaac gcgaggaacc ttaccagcgt ttgacatcct    960
aagaagtcta tagagatatg gatgtgctcc ttcgggagaa cttagtgaca ggtggtgcat    1020
ggctgtcgtc agctcgtgtc gtgagatgtt gggttaagtc ccgcaacgag cgcaacccct    1080
```

-continued

```
ttcgtatgtt accatcatta agttggggac tcatgcgata ctgcctgcga tgagcaggag   1140
gaaggtgggg atgacgtcaa gtcatcatgc cccttatacg ctgggctaca cacgtgctac   1200
aatgggtagt acagagagaa gcgaaactgc gaggtggagc aaatctcaga aaactattct   1260
tagttcggat tgtactctgc aactcgagta catgaagttg gaatcgctag taatcgcaaa   1320
tcagctatgt tgcggtgaat acgttctcgg gtcttgtaca caccgcccgt cacaccacga   1380
gagttggttg cacctgaagt aacaggccta accgtaagga gggatgttcc gagggtgtga   1440
ttagcgattg gggtgaagtc gtaacaaggt atccgtacgg gaacgtgcgg atggatcacc   1500
tccttt                                                             1506

SEQ ID NO: 14              moltype = RNA   length = 1547
FEATURE                    Location/Qualifiers
source                     1..1547
                           mol_type = rRNA
                           organism = Lactococcus allomyrinae
                           strain = 1JSPR-7
SEQUENCE: 14
ttatttgaga gtttgatcct ggctcaggac gaacgctggc ggcgtgccta atacatgcaa   60
gttgagcgct gaaggaaggt acttgtaccg actggaagag cagcgaacgg gtgagtaacg   120
cgtggggaat ctgcctttga gcgggggaca acatttggaa acgaatgcta ataccgcata   180
acaactttaa acacaagtta aaagtttgaa agatgcaaaa gcatcactca gagatgatcc   240
cgcgttgtat tagctagttg gtgaggtaaa ggctcaccaa ggcgatgata catagccgac   300
ctgagagggt gatcggccac attgggactg agacacggcc caaactccta cgggaggcag   360
cagtagggaa tcttcggcaa tggacgaaag tctgaccgag caacgccgcg tgagtgaaga   420
aggttttcgg atcgtaaaac tctgttgtta gagaagaacg tgtgtgggag tggaaaatcc   480
atgcagtgac ggtatctaac cagaaaggga cggctaacta cgtgccagca gccgcggtaa   540
tacgtaggtc ccgagcgttg tccggattta ttgggcgtaa agcgagcgca ggtggtttat   600
taagtctggt gtaaaaggca gtggctcaac cattgtatgc attggaaact ggtagacttg   660
agtgcaggag aggagagtgg aattccatgt gtagcggtga aatgcgtaga tatatggagg   720
aacaccggtg gcgaaagcgg ctctctggcc tgtaactgac actgaggctc gaaagcgtgg   780
ggagcaaaca ggattagata ccctggtagt ccacgccgta aacgatgagt gctagatgta   840
ggaagctata agttttctgt atcgcagcta acgcaataag cactccgcct ggggagtacg   900
accgcaaggt tgaaactcaa aggaattgac ggggcccgc acaagcggtg gagcatgtgg   960
tttaattcga gcaacgcga agaaccttac caggtcttga catcccgatg ctatccttag   1020
agataaggag ttacttcggt acatcggtga caggtggtgc atggttgtcg tcagctcgtg   1080
tcgtgagatg ttgggttaag tcccgcaacg agcgcaaccc ctattactag ttgccatcat   1140
taagttgggc actctagtga gactgccggt gataaaccgg aggaaggtgg ggatgacgtc   1200
aaaatcatcat gcccccttatg acctgggcta cacacgtgct acaatggatg gtacaacgag   1260
tcgcgagaca gtgatgttta gctaatctct taaaaccatt ctcagttcgg attgtaggct   1320
gcaactcgcc tacatgaagt cggaatcgct agtaatcgcg gatcagcacg ccgcggtgaa   1380
tacgttcccg ggccttgtac acaccgcccg tcacaccacg ggagttggga gtacccgaag   1440
taggttgcct aaccgcaagg agggcgcttc ctaaggtaag accgatgact ggggtgaagt   1500
cgtaacaagg tagccgtatc ggaaggtgcg gctggatcac ctcctttt              1547

SEQ ID NO: 15              moltype = RNA   length = 1563
FEATURE                    Location/Qualifiers
source                     1..1563
                           mol_type = rRNA
                           organism = Lactobacillus mulieris
                           strain = c10Ua161M
SEQUENCE: 15
caaaatgaga gtttgatcct ggctcaggac gaacgctggc ggcgtgccta atacatgcaa   60
gtcgagcgag cttgcctatt gaaattcttc ggaatggaca tagatacaag ctagcggcgg   120
atgggtgagt aacgcgtggg taacctgccc ttaagtctgg gataccattt ggaaacagat   180
gctaataccg gataaaagct actttcgcat gaaagaagtt taaaaggcgg cgtaagctgt   240
cgctaaagga tggacctgcg atgcattagc tagttggtaa ggtaacggct taccaaggcg   300
atgatgcata gccgagttga gagactgatc ggccacattg ggactgagac acggcccaaa   360
ctcctacggg aggcagcagt agggaatctt ccacaatgga cgcaagtctg atggagcaac   420
gccgcgtgag tgaagaaggt tttcggatcg taaagctctg ttgttggtga agaaggatag   480
aggtagtaac tggccttttat ttgacggtaa tcaaccagaa agtcacggct aactacgtgc   540
cagcagccgc ggtaatacgt aggtggcaag cgttgtccgg atttattggg cgtaaagcga   600
gcgcaggcgg attgataagt ctgatgtgaa agccttcggc tcaaccgaag aactgcatca   660
gaaactgtca atcttgagtg cagaagagga gagtggaact ccatgtgtag cggtggaatg   720
cgtagatata tggaagaaca ccagtggcga aggcggctct ctggtctgta actgacgctg   780
aggctcgaaa gcatgggtag cgaacaggat tagatacct ggtagtccat gccgtaaacg   840
atgagtgcta agtgttggga ggtttccgcc tctcagtgct gcagctaacg cattaagcac   900
tccgcctggg gagtacgacc gcaaggttga aactcaaagg aattgacggg ggcccgcaca   960
agcggtggag catgtggttt aattcgaagc aacgcgaaga accttaccag gtcttgacat   1020
cctttgacca cctaagagat taggttttcc cttcggggac aaagacag gtggtgcatg   1080
gctgtcgtca gctcgtgtcg tgagatgttg ggttaagtcc cgcaacgagc caacccttg   1140
ttaatagttg ccagcattaa gttgggcact ctattgacga tgccggtgac aaaccggagg   1200
aaggtgggga tgacgtcaag tcatcatgcc ccttatgacc tgggctacac acgtgctaca   1260
atgggcagta caacgagaag cgaacctgtg aaggcaagcg gatctcttaa agctgttctc   1320
agttcggact gtaggctgca actcgcctac acgaagctgg aatcgctagt aatcgcggat   1380
cagcacgccg cggtgaatac gttcccgggc cttgtacaca ccgcccgtca ccatgagag   1440
gtttgtaaca cccaaagtcg gtgaggtaac cttttggagcc agccgcctaa ggtgggacag   1500
atgattaggg tgaagtcgta acaaggtagc cgtaggagaa cctgcggctg gatcacctcc   1560
ttt                                                               1563
```